United States Patent
Graziani et al.

(10) Patent No.: US 11,591,337 B2
(45) Date of Patent: Feb. 28, 2023

(54) SUBSTITUTED [1,2,4]TRIAZOLO[4,3-A]PYRAZINES AS MODULATORS OF MGLU5 RECEPTORS

(71) Applicant: Recordati Industria Chimica e Farmaceutica S.p.A., Milan (IT)

(72) Inventors: Davide Graziani, Milan (IT); Carlo Riva, Milan (IT); Sergio Menegon, Milan (IT); Valerio Tazzari, Milan (IT)

(73) Assignee: Recordati Industria Chimica e Farmaceutica S.p.A., Milan (IT)

( * ) Notice: Subject to any disclaimer, the term of this patent is extended or adjusted under 35 U.S.C. 154(b) by 0 days.

(21) Appl. No.: 16/964,337

(22) PCT Filed: Jan. 17, 2019

(86) PCT No.: PCT/EP2019/051134
§ 371 (c)(1),
(2) Date: Jul. 23, 2020

(87) PCT Pub. No.: WO2019/145214
PCT Pub. Date: Aug. 1, 2019

(65) Prior Publication Data
US 2021/0047331 A1    Feb. 18, 2021

Related U.S. Application Data

(60) Provisional application No. 62/622,379, filed on Jan. 26, 2018.

(51) Int. Cl.
*A61K 31/4985*    (2006.01)
*C07D 487/04*    (2006.01)

(52) U.S. Cl.
CPC .................. *C07D 487/04* (2013.01)

(58) Field of Classification Search
CPC .................. A61K 31/4985; C07D 487/04
USPC .......................... 514/249; 544/350
See application file for complete search history.

(56) References Cited

FOREIGN PATENT DOCUMENTS

| EP | 2085398 | 5/2009 |
| EP | 2090576 | 8/2009 |
| EP | 2604610 | 6/2013 |
| WO | WO2010017047 | 2/2010 |
| WO | WO2011121137 | 10/2011 |
| WO | WO2012172093 | 12/2012 |
| WO | WO-2019145214 A1 * | 8/2019 ......... A61K 31/4985 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report for PCT/EP2019/051134 dated Mar. 6, 2019.

* cited by examiner

*Primary Examiner* — Douglas M Willis
(74) *Attorney, Agent, or Firm* — Hueschen and Sage

(57) ABSTRACT

Disclosed are triazole, imidazole and pyrrole condensed piperazine derivatives and their use as allosteric modulators of mGlus receptor activity, pharmaceutical compositions comprising such compounds, and methods of treatment therewith. Compounds of the invention can be used for the treatment and/or prevention of neurological and psychiatric disorders associated with glutamate dysfunction such as schizophrenia or cognitive decline, dementia or cognitive impairment, or other pathologies that can be related either directly or indirectly to glutamate dysfunction, i.e., disorders treatable by positive allosteric modulation (PAM) or by negative allosteric modulation (NAM) of mGluR$_5$.

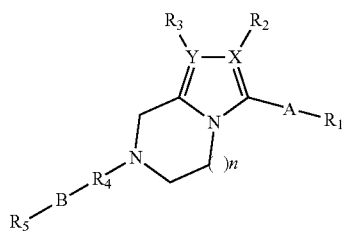

11 Claims, No Drawings

SUBSTITUTED [1,2,4]TRIAZOLO[4,3-A]PYRAZINES AS MODULATORS OF MGLU5 RECEPTORS

FIELD OF THE INVENTION

This invention relates to triazole, imidazole and pyrrole condensed piperazine derivatives and their use as allosteric modulators of mGlu$_5$ receptor activity, pharmaceutical compositions comprising such compounds, and methods of treatment therewith. Compounds of the invention can be used for the treatment and/or prevention of neurological and psychiatric disorders associated with glutamate dysfunction such as schizophrenia or cognitive decline, dementia or cognitive impairment, or other pathologies that can be related either directly or indirectly to glutamate dysfunction, i.e., disorders treatable by positive allosteric modulation (PAM) or by negative allosteric modulation (NAM) of mGluR$_5$.

Glutamate is the primary excitatory amino acid in the mammalian central nervous system, exerting its effects through both ionotropic and metabotropic glutamate receptors. Neurotransmission mediated by glutamate has been demonstrated to be critical in many physiological processes, such as synaptic plasticity, long-term potentiation involved in both learning and memory as well as sensory perception (Riedel et al., *Behav. Brain Res.* (2003), Vol. 140, pp. 1-47, Rose et al. *J. Neurosci.*, Nov. 8, 2006 • 26(45):11582-11587).

Furthermore, it has been demonstrated that an imbalance of glutamate neurotransmission plays a critical role in the pathophysiology of various neurological and psychiatric diseases.

The excitatory neurotransmission of glutamate is mediated through at least two different classes of receptors: ionotropic glutamate receptors such as the N-methyl-D-aspartate receptor (NMDA), α-amino-3-hydroxy-5-methyl-4-isoxazolepropionic acid receptor (AMPA) or kainite receptor; and the metabotropic glutamate receptors (mGluR) and metabotropic glutamate receptors. The ionotropic receptors are ligand gated ion channels and are thought to be responsible for regulating the rapid neuronal transmission between two neurons. The metabotropic glutamate receptors are G-protein coupled receptors (GPCRs) which appear to mediate not only synaptic transmission, but also to regulate the extent of neurotransmitter release as well as post synaptic receptor activation. The metabotropic glutamate receptors (mGluRs) belong to family C (also known as family 3) of the g-protein-coupled receptors (GPCRs). They are characterized by a seven transmembrane (7TM) a-helical domain connected via a cysteine rich-region to a large bi-lobed extracellular amino-terminal domain where the glutamate ligand binds. The mGluR family comprises eight known mGluRs receptor types (designated as mGluR1 through mGluR8). Several of the receptor types are expressed as specific splice variants, e.g. mGluR5a and mGluR5b or mGluR8a, mGluR8b and mGluR8c.

This superfamily is further divided into three groups (Groups I, II and III) based on amino acid homology as well as the intracellular signaling cascades they regulate (Schoepp et al., *Neuropharma*, (1999), Vol. 38, pp. 1431-1476) and pharmacological profile. Group I receptors (mGluR1 and mGluR5) are coupled to $G_{\alpha q}$, a process that results in stimulation of phospholipase C and an increase in intracellular calcium and inositol phosphate levels. Group II receptors (mGluR2 and mGluR3) and group iii receptors (mGluR4, mGluR6, mGluR7, and mGluR8) are coupled to $G_{\alpha i}$, which leads to decreases in cyclic adenosine monophosphate (cAMP) levels. While the group I receptors are predominately located postsynaptically and typically enhance postsynaptic signaling, the group II and III receptors are located presynaptically and typically have inhibitory effects on neurotransmitter release.

Dysregulation in glutamatergic neurotransmission, for example through altered glutamate release or post-synaptic receptor activation, has been demonstrated in a variety of neurological as well as psychiatric disorders. Hypofunction of the NMDA receptor has not only been demonstrated in Alzheimer's patients, but is increasingly accepted as the putative cause of schizophrenia (Farber et al., *Prog. Brain Res.*, (1998), Vol. 116, pp. 421-437, Coyle et al., *Cell. and Mol. Neurobiol.*, (2006), Vol. 26, pp. 365-384). This is supported by clinical studies showing that antagonists of the NMDA receptor induce symptoms indistinguishable to those suffered by schizophrenia patients (Javitt et al., *Am J. Psychiatry*, (1991), Vol. 148, pp. 1301-1308; Meltzer H Y, *Biol. Psychiatry*, (1999), Vol. 46(10), pp. 1321-1327). Therefore, approaches that could potentiate or normalize NMDA receptor signaling have the potential to treat neurological and psychiatric disorders.

mGluR$_5$, encoded by the GRM5 gene, has been demonstrated to be expressed in the central nervous system (CNS), mainly in the cortex, hippocampus, nucleus accumbens and the caudate-putamen. These brain regions are known to be involved in memory formation and cognitive function as well as emotional response. mGluR5 has been shown to be localized post-synaptically, adjacent to the post-synaptic density (Lujan et al., *Eur. J. Neurosci.* (1996), Vol. 8, pp. 1488-1500). A functional interaction between mGluR5 and the NMDA receptor has also been demonstrated, where activation of mGluR$_5$ potentiates the activation state of the NMDA receptor (Mannaioni et al., *NeuroSci.*, (2001), Vol. 21, pp. 5925-5924, Rosenbrock et al., *Eur. J. Pharma.*, (2010), Vol. 639, pp. 40-46). Furthermore, activation of mGluR5 has been demonstrated in pre-clinical in vivo models to rescue cognitive impairment as well as psychotic disturbance induced by NMDA receptor antagonists (Chan et al., *Psychopharma.* (2008), Vol. 198, pp. 141-148). Therefore, activation of mGluR$_5$, and thereby potentiation or normalization of the NMDA receptor signaling, is a potential mechanism for the treatment of psychiatric and neurological disorders.

Most agonists of mGluR$_5$ bind the orthosteric glutamate binding site. Since the glutamate binding site between the mGluR family members is highly conserved, it has been challenging to develop selective mGlu$_5$ agonists which have acceptable CNS penetration and demonstrate in vivo activity.

An alternative approach to achieve selectivity between the mGluR family members is to develop compounds which bind to an allosteric site, which is not as highly conserved between the family members. These allosteric binding compounds would not interfere with the natural glutamate binding and signaling but modulate the receptor activation state. Allosteric ligands that have agonistic or inverse agonistic activity in the absence of orthosteric ligands are termed allosteric agonists or antagonists, respectively. Allosteric ligands lacking effect in the absence of orthosteric ligands are termed modulators (negative or positive).

Positive allosteric modulators of mGluR$_5$ have recently been identified (O'Brien et al., *Mol. Pharma.* (2003), Vol. 64, pp. 731-740, Lindsley et al., *J. Med. Chem.* (2004), Vol. 47, pp. 5825-5828), where it has been determined that these compounds potentiate mGluR$_5$ activity in the presence of bound glutamate. In the absence of bound glutamate, the mGlu$_5$ positive modulators do not demonstrate any intrinsic activity.

Therefore, these compounds potentiate the natural signaling of mGluR$_5$ as opposed to agonists which activate the receptor in a permanent, unnatural manner. mGluR$_5$ positive allosteric modulators therefore represent an approach to potentiate mGluR$_5$ signaling which in turn potentiates and normalizes the NMDA receptor hypofunction detected in neurological and psychiatric disorders. mGluR$_5$ negative allosteric modulators are useful to depress the mGluR$_5$ signaling which in turn decreases and normalizes the NMDA receptor hyperfunction detected in some neurological, psychiatric disorders and in more general CNS disorders. Without wishing to be bound by a particular theory, metabotropic glutamate receptors, including mglur5, have been implicated in a wide range of biological functions, indicating a potential role for the mGluR$_5$ receptor in a variety of disease processes in mammals. Ligands of metabotropic glutamate receptors can be used for the treatment or prevention of acute and/or chronic neurological and/or psychiatric disorders associated with glutamate dysfunction, such as psychosis, schizophrenia, age-related cognitive decline, and the like. Further, without wishing to be bound by theory, increasing evidence indicates mGlu receptors play an important role in lasting changes in synaptic transmission, and studies of synaptic plasticity in the FMRI knockout mouse have identified a connection between the Fragile X phenotype and mGluR signaling. Both types of allosteric modulator can also be related to some rare disease e.g. without any kind of limitation, Fragile-X syndrome, Rett syndrome, Phelan-McDermid syndrome or tuberous sclerosis.

The identification of small molecule mGluR agonists that bind at the orthosteric site has greatly increased the understanding of the roles played by these receptors and their corresponding relation to disease. Because the majority of these agonists were designed as analogs of glutamate, they typically lack the desired characteristics for drugs targeting mGluR such as oral bioavailability and/or distribution to the central nervous system (CNS). moreover, because of the highly-conserved nature of the glutamate binding site, most orthosteric agonists lack selectivity among the various mGluRs.

Allosteric binding sites are topographically distinct from the endogenous ligand (orthosteric) binding site. The contemporary occupation into the receptor by the endogenous ligand and an allosteric modulator on both sites may results in different outcomes. Allosteric ligands potentiating the effect of the endogenous ligand (positive cooperativity) are defined "positive allosteric modulators" (PAMs), while allosteric ligands decreasing or blocking the effect of the endogenous ligand (negative cooperativity) are defined negative allosteric modulators (NAMs). (Christopoulos A, Advances in G protein-coupled receptor allostery: from function to structure, Mol Pharmacol. 2014; 86 (5):463-78).

Both PAMs and NAMs are thus an attractive mechanism for modulating appropriate physiological receptor responses.

Unfortunately, there is a scarcity of selective positive allosteric modulators for the mGluR$_5$ receptor. Further, conventional mGluR$_5$ receptor modulators typically lack satisfactory aqueous solubility and exhibit poor oral bioavailability. Therefore, there remains a need for methods and compositions that overcome these deficiencies and that effectively provide selective positive but also negative allosteric modulators for the mGluR$_5$ receptor.

SUMMARY OF THE INVENTION

The invention provides a compound having the general formula I:

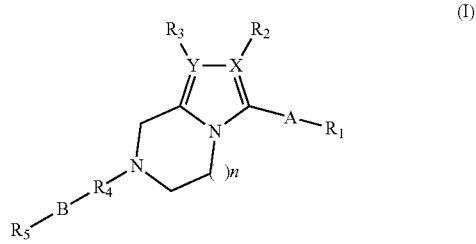

or an enantiomer, diastereomer, N-oxide, or a pharmaceutically acceptable salt thereof, wherein:

$R_1$ is an optionally substituted mono-, bi- or tricyclic $C_6$-$C_{14}$ aryl group, an optionally substituted mono-, bi- or tricyclic $C_1$-$C_{13}$ heterocyclic group containing from 1 to 5 heteroatoms selected from N, O, and S, an optionally substituted $C_3$-$C_6$ cycloalkyl group, or an optionally substituted $C_3$-$C_6$ cycloalkenyl group or an optionally substituted $C_1$ to $C_{20}$ linear or branched alkyl group;

and

A is a triple bond, a double bond, optionally substituted with a halo group or represents a five- or six-atom heterocyclic group containing from 1 to 4 heteroatoms selected from N, S, O, or represents an alkyl chain ($C_{1-4}$), or alkyl chain substituted with one to three heteroatoms selected from N, S, O;

$R_2$, $R_3$ are each independently null, a hydrogen, an alkyl group, or a fluorine atom, or $R_2$ and $R_3$ are linked to each other to form a condensed heterocyclic ring containing one to three heteroatoms selected from N, S, O;

n is an integer between 0 and 2;

$R_4$ is a carbonyl, or a thiocarbonyl, or a sulphonyl group, or a bond or null;

B is oxygen or sulphur or nitrogen wherein the nitrogen is optionally substituted by a $C_{1-5}$ alkyl or alkoxy such as a methoxy or a bond or null;

$R_5$ is an optionally substituted mono-, bi- or tricyclic $C_6$-$C_{14}$ aryl group, an optionally substituted mono-, bi- or tricyclic $C_1$-$C_{13}$ heterocyclic group containing from 1 to 5 heteroatoms selected from N, O, and S, an optionally substituted $C_3$-$C_6$ cycloalkyl group, or an optionally substituted $C_3$-$C_6$ cycloalkenyl group or an optionally substituted linear or branched C1 to C20 alkyl group.

The optional substituents mentioned above are independently selected from halogen atoms and $C_1$-$C_6$ alkyl, $C_1$-$C_6$ alkoxy, hydroxy, mercapto, nitro, cyano, oxo, halo($C_1$-$C_6$) alkyl, halo($C_1$-$C_6$)alkoxy, $C_1$-$C_6$ alkylthio, $C_1$-$C_6$ alkylsulphonyl, $C_1$-$C_6$ alkylcarbonyl, sulphamoyl, $C_1$-$C_6$ alkylsulphamoyl, di($C_1$-$C_6$)alkylsulphamoyl, ($C_1$-$C_6$) alkoxycarbonyl and (C1-$C_6$)alkylcarbonyl($C_1$-$C_6$)alkyl groups, and from groups of the formulae —NR*R*, —C(=O)—NR*R*, -A, —O-A, —C(=O)-A, —(CH$_2$)q-A, —NR-A, —C(=O)—NR-A, —NR**C(=O)-A and —O—C(=O)-A wherein each R* independently represents a hydrogen atom or a $C_1$-$C_6$ alkyl, $C_1$-$C_6$ alkoxy, $C_1$-$C_6$ alkylcarbonyl, phenyl or benzyl group, R** represents a hydrogen atom or a $C_1$-$C_6$ alkyl group, q is an integer from 1 to 6 and A represents a phenyl group or a $C_1$-$C_8$ heterocyclic group containing from 1 to 3 heteroatoms selected from N, O and S; a $C_1$-$C_6$ cycloalkyl group; each group A being optionally substituted with from 1 to 3 groups independently selected from halo, hydroxy, cyano, nitro and $C_1$-$C_6$ alkyl, preferably wherein the optional substituents are selected from the groups consisting of halogen atoms and $C_1$-$C_6$ alkyl groups.

In preferred embodiments, A is a triple or double bond, optionally substituted with a halo group. $R_1$ is preferably an optionally substituted $C_3$-$C_6$ cycloalkyl group, or an optionally substituted $C_3$-$C_6$ cycloalkenyl group or a C3-$C_5$ heterocyclic group containing at least one heteroatom selected from N, O, and S, preferably wherein the heteroatom is N. X and Y are preferably each independently N or C. Most preferably, n=1.

In preferred embodiments, $R_4$ is a carbonyl group or null; B is O, N optionally substituted with $C_{1-5}$ alkyl or alkoxy such as a methoxy or a bond or null; and $R_5$ is as defined above.

In some embodiments, if B is O, $R_5$ is a $C_1$-$C_{13}$ heterocyclic group containing from 1 to 5 heteroatoms selected from N, O, and S, or an optionally substituted linear or branched C1 to C20 alkyl group. If B is null, $R_5$ is preferably an optionally substituted mono-, bi- or tricyclic $C_6$-$C_{14}$ aryl group, an optionally substituted mono-, bi- or tricyclic $C_1$-$C_{13}$ heterocyclic group containing from 1 to 5 heteroatoms selected from N, O, and S, an optionally substituted $C_3$-$C_6$ cycloalkyl group, or an optionally substituted $C_3$-$C_6$ cycloalkenyl group. If B is N optionally substituted by a $C_{1-5}$ alkyl or alkoxy such as a methoxy, $R_5$ is preferably or an optionally substituted linear or branched C1 to C20 alkyl group.

In some embodiments, there is only one possible n (=1), flanking the ring nitrogen atom, yielding the formula IA:

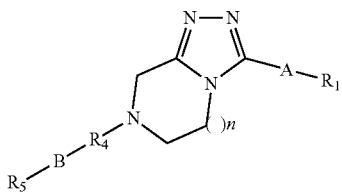

IA

Wherein A, B, and $R_1$, $R_4$ and $R_5$ have the meanings ascribed to them in connection with Formula I above.

In some embodiments, there is only one possible n (=1), flanking the ring nitrogen atom, yielding the formula IB:

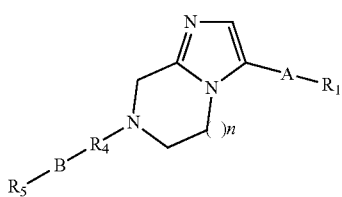

IB

Wherein A, B, and $R_1$, $R_4$ and $R_5$ have the meanings ascribed to them in connection with Formula I above.

In some embodiments, there is only one possible n (=1), adjacent to the ring nitrogen atom, yielding the formula IC:

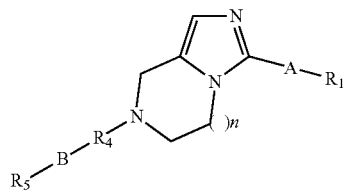

IC

Wherein A, B, and $R_1$, $R_4$ and $R_5$ have the meanings ascribed to them in connection with Formula I above.

Preferred compounds according to the invention are those in which $R_1$ and $R_5$ are an optionally substituted mono-, bi- or tricyclic C6-$C_{14}$ aryl group, an optionally substituted mono-, bi- or tricyclic $C_1$-$C_{13}$ heterocyclic group containing from 1 to 5 heteroatoms selected from N, O, and S, A is a triple bond or an oxymethylene or methylenoxy group, $R_4$ represents a CO group, n is 1, X and Y are nitrogen, $R_2$ and $R_3$ are null and B is null (bond).

In an embodiment of the invention, $R_1$, $R_5$ are preferably independently selected from optionally substituted mono-, bi- or tricyclic $C_6$-$C_{14}$ aryl group or optionally substituted mono-, bi- or tricyclic $C_1$-$C_{13}$ heterocyclic group containing from 1 to 5 heteroatoms selected from N, O, S, A is a triple bond or an oxymethylene or a methylenoxy group, X and Y are nitrogen, $R_2$ and $R_3$ are null, and B is a heteroatom selected from N, O, S.

In another embodiment of the invention, $R_1$, $R_5$ are preferably independently selected from optionally substituted mono-, bi- or tricyclic $C_6$-$C_{14}$ aryl group or optionally substituted mono-, bi- or tricyclic $C_1$-$C_{13}$ heterocyclic group or optionally substituted alkyl or cycloalkyl or cycloalkenyl group containing from 1 to 5 heteroatoms selected from N, O, and S, X is a carbon and Y is a nitrogen, $R_3$ is null and $R_2$ is a hydrogen or a methyl group, A is a triple bond or an oxymethylene or methylenoxy group and B is null (bond).

In a further embodiment of the invention, $R_1$, $R_5$ are preferably independently selected from optionally substituted monocyclic aryl group or optionally substituted monocyclic heterocyclic group containing from 1 to 5 heteroatoms selected from N, O, S or an optionally substituted alkyl or cycloalkyl or cycloalkenyl group, X is a carbon and Y is a nitrogen, $R_3$ is null and $R_2$ is hydrogen or a methyl group, A is a triple bond an oxymethylene or methylenoxy group, where $R_4$ is a CO group and B is a heteroatom selected from N, O, S.

In a further embodiment of the invention, $R_1$, $R_5$ are preferably independently selected from optionally substituted monocyclic aryl group or optionally substituted monocyclic heterocyclic group containing from 1 to 5 heteroatoms selected from N, O, and S or optionally substituted alkyl or cycloalkyl or cycloalkenyl group, X is a nitrogen and Y is a carbon, $R_2$ is null and $R_3$ is a hydrogen or a methyl group, A is a triple bond an oxymethylene or methylenoxy group, where $R_4$ is a CO group and B is null (bond).

In a further embodiment of the invention, $R_1$, $R_5$ are preferably independently selected from optionally substituted monocyclic aryl group or optionally substituted monocyclic heterocyclic group containing from 1 to 5 heteroatoms selected from N, O, S or an optionally substituted alkyl or cycloalkyl or cycloalkenyl group, X is a nitrogen and Y is a carbon, $R_2$ is null and $R_3$ is hydrogen or a methyl group, A is a triple bond an oxymethylene or methylenoxy group, where $R_4$ is a CO group and B is a heteroatom selected from N, O, S.

In a further embodiment of the invention, A is preferably an alkyloxy group.

In a further embodiment of the invention, A is preferably a heterocyclic ring or a double bond.

In a further embodiment of the invention, $R_2$ and $R_3$ are preferably a hydrogen atom.

In a further embodiment of the invention, $R_2$ and $R_3$ are preferably an optionally substituted $C_1$-$C_4$ alkyl group;

For example, when $R_4$ is a CO group and $R_1$ represents an optionally substituted mono- or bicyclic $C_1$-$C_9$ heterocyclic group containing from 1 to 3 heteroatoms selected from nitrogen, oxygen and sulfur, $R_5$ is preferably without any limitation a 2-furyl, 3-methylphenyl, 3-chlorophenyl, 5-methyl-2-furyl, 3-furyl, 2,5-dimethyl-3-furyl, 4-morpholinyl, piperidinyl, pyrrolidinyl group.

For example, when $R_4$ is a CO group, B is Oxygen and $R_1$ represents an optionally substituted mono- or bicyclic $C_1$-$C_9$ heterocyclic group containing from 1 to 3 heteroatoms selected from nitrogen, oxygen and sulfur, n is 1 and $R_5$ is preferably without any limitation an alkyl group, optionally substituted, chosen from methyl, ethyl, isopropyl, propyl, tert-butyl, butyl, isobutyl compounds are preferentially negative allosteric modulators.

For example, when $R_4$ is a CO group, B is nitrogen or N-alkyl chosen from methyl, ethyl, isopropyl, propyl, tert-butyl, butyl, isobutyl or methoxy and $R_1$ represents an optionally substituted mono- or bicyclic $C_1$-$C_9$ heterocyclic group containing from 1 to 3 heteroatoms selected from nitrogen, oxygen and sulfur, n is 1 and $R_5$ is preferably without any limitation an alkyl group optionally substituted chosen from methyl, ethyl, isopropyl, propyl, tert-butyl, butyl, isobutyl optionally substituted compounds are preferentially negative allosteric modulators.

A non-limiting example is 3-[2-(3-chlorophenyl)ethynyl]-N,N-diethyl-6,8-dihydro-5H-[1,2,4]triazolo[4,3-a]pyrazine-7-carboxamide. In this compound, $R_1$ is a 3-chlorophenyl, B is an ethylated nitrogen and $R_5$ is an ethyl group, $R_2$ and $R_3$ are null, $R_4$ is carbonyl, n is 1, and A is a triple bond.

For example, when $R_4$ is a CO group, B is null and $R_1$ represents an optionally substituted mono-, bi- or tricyclic $C_6$-$C_{14}$ aryl group, n is 1 and $R_5$ is preferably without any limitation an optionally substituted monocyclic aryl group or optionally substituted monocyclic heterocyclic group containing from 1 to 5 heteroatoms selected from N, O, and S group, compounds are preferentially positive allosteric modulators.

A non-limiting example is (3-chlorophenyl)-[3-[2-(3-chlorophenyl)ethynyl]-6,8-dihydro-5H-[1,2,4]triazolo[4,3-a]pyrazin-7-yl]methanone. In this compound, $R_1$ and $R_5$ are 3-chlorophenyl, $R_2$ and $R_3$ and B are null, $R_4$ is carbonyl, n is 1, and A is a triple bond. The compound is further described in Example 8.

For example, when X is nitrogen and Y is carbon, $R_4$ is a CO group, B is null and $R_1$ represents an optionally substituted mono-, bi- or tricyclic $C_6$-$C_{14}$ aryl group, $R_5$ is preferably without any limitation optionally substituted monocyclic aryl group or optionally substituted monocyclic heterocyclic group containing from 1 to 5 heteroatoms selected from N, O, and S, compounds are preferentially positive allosteric modulators.

A nonlimiting example is (3-chlorophenyl)-[3-[2-(3-chlorophenyl)ethynyl]-6,8-dihydro-5H-imidazo[1,2-a]pyrazin-7-yl]methanone. In this compound, $R_1$ and $R_5$ are 3-chlorophenyl, A is a triple bond, B is a null, $R_2$ is null and $R_3$ is hydrogen, $R_4$ is carbonyl and n is 1.

In an embodiment of the invention, a compound, or a nenantiomer, diastereomer, N-oxide, or a pharmaceutically acceptable salt, is provided according to general formula I selected from the compounds in Table 1 below:

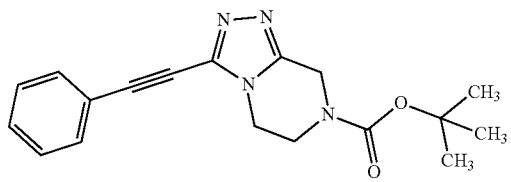

tert-butyl 3-(2-phenylethynyl)-6,8-dihydro-5H-[1,2,4]triazolo[4,3-a]pyrazine-7-carboxylate

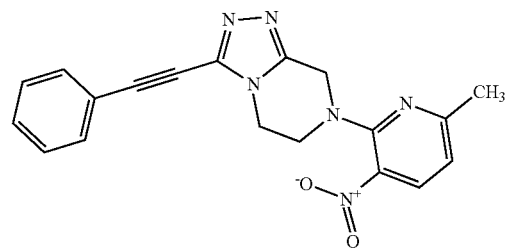

7-(6-methyl-3-nitro-2-pyridyl)-3-(2-phenylethynyl)-6,8-dihydro-5H-[1,2,4]triazolo[4,3-a]pyrazine

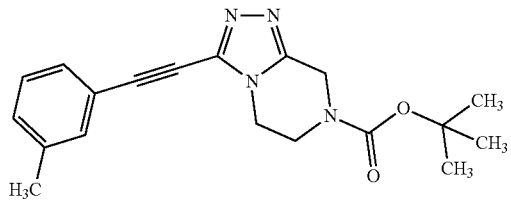 [SMILES: Cc1cccc(C#Cc2nnc3n2CCN(C(=O)OC(C)(C)C)C3)c1]

tert-butyl 3-[2-(m-tolyl)ethynyl]-6,8-dihydro-5H-[1,2,4]triazolo[4,3-a]pyrazine-7-carboxylate

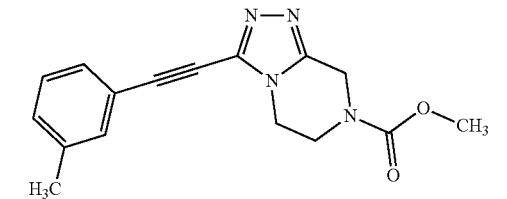 [SMILES: COC(=O)N1CCn2c(C#Cc3cccc(C)c3)nnc2C1]

methyl 3-[2-(m-tolyl)ethynyl]-6,8-dihydro-5H-[1,2,4]triazolo[4,3-a]pyrazine-7-carboxylate

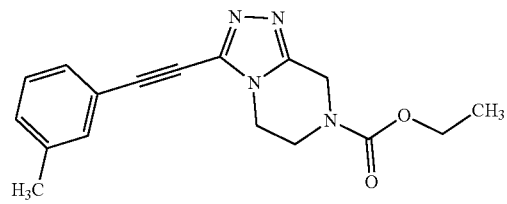 [SMILES: CCOC(=O)N1CCn2c(C#Cc3cccc(C)c3)nnc2C1]

ethyl 3-[2-(m-tolyl)ethynyl]-6,8-dihydro-5H-[1,2,4]triazolo[4,3-a]pyrazine-7-carboxylate

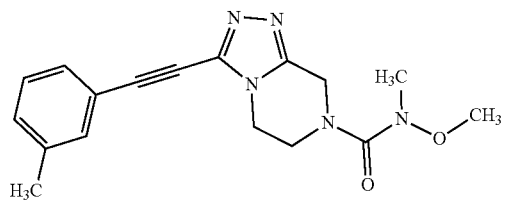 [SMILES: CON(C)C(=O)N1CCn2c(C#Cc3cccc(C)c3)nnc2C1]

N-methoxy-N-methyl-3-[2-(m-tolyl)ethynyl]-6,8-dihydro-5H-[1,2,4]triazolo[4,3-a]pyrazine-7-carboxamide

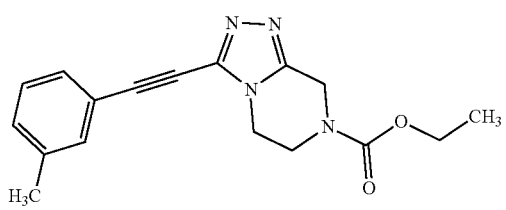 [SMILES: CCOC(=O)N1CCn2c(C#Cc3cccc(C)c3)nnc2C1]

ethyl 3-[2-(m-tolyl)ethynyl]-6,8-dihydro-5H-[1,2,4]triazolo[4,3-a]pyrazine-7-carboxylate

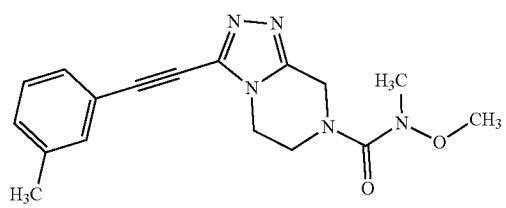 [SMILES: CON(C)C(=O)N1CCn2c(C#Cc3cccc(C)c3)nnc2C1]

N-methoxy-N-methyl-3-[2-(m-tolyl)ethynyl]-6,8-dihydro-5H-[1,2,4]triazolo[4,3-a]pyrazine-7-carboxamide

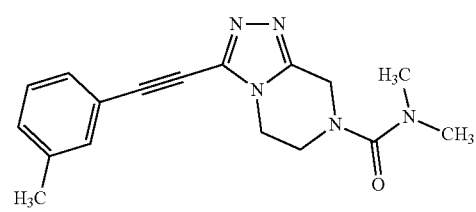 [SMILES: Cc1cccc(C#Cc2nnc3n2CCN(C(=O)N(C)C)C3)c1]

N,N-dimethyl-3-[2-(m-tolyl)ethynyl]-6,8-dihydro-5H-[1,2,4]triazolo[4,3-a]pyrazine-7-carboxamide

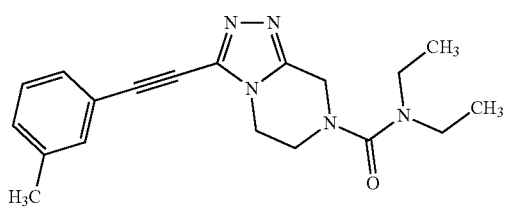 [SMILES: CCN(CC)C(=O)N1CCn2c(C#Cc3cccc(C)c3)nnc2C1]

N,N-diethyl-3-[2-(m-tolyl)ethynyl]-6,8-dihydro-5H-[1,2,4]triazolo[4,3-a]pyrazine-7-carboxamide

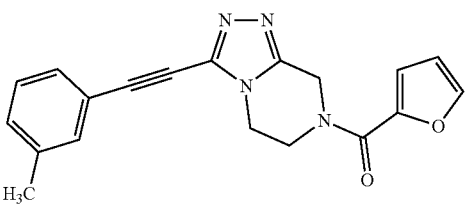 [SMILES: Cc1cccc(C#Cc2nnc3n2CCN(C(=O)c2ccco2)C3)c1]

2-furyl-[3-[2-(m-tolyl)ethynyl]-6,8-dihydro-5H-[1,2,4]triazolo[4,3-a]pyrazine-7-yl]methanone

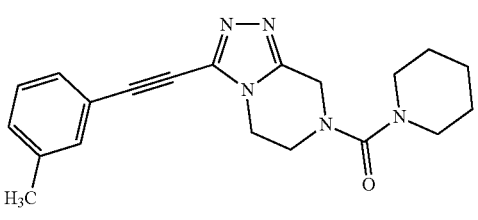

([3-[2-(m-tolyl)ethynyl]-6,8-dihydro-5H-[1,2,4]triazolo[4,3-a]pyrazin-7-yl]-(1-piperidyl)methanone

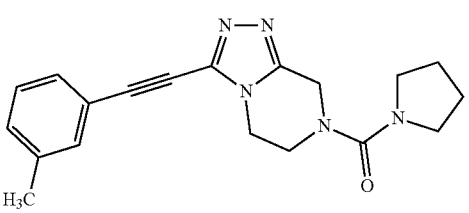 [SMILES: Cc1cccc(C#Cc2nnc3n2CCN(C(=O)N2CCCC2)C3)c1]

[3-[2-(m-tolyl)ethynyl]-6,8-dihydro-5H-[1,2,4]triazolo[4,3-a]pyrazin-7-yl]-pyrrolidin-1-yl-methanone

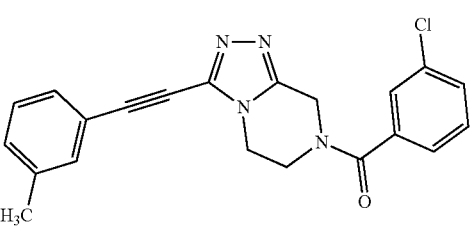 [SMILES: Cc1cccc(C#Cc2nnc3n2CCN(C(=O)c2cccc(Cl)c2)C3)c1]

(3-chlorophenyl)-[3-[2-(m-tolyl)ethynyl]-6,8-dihydro-5H-[1,2,4]triazolo[4,3-a]pyrazin-7-yl]methanone

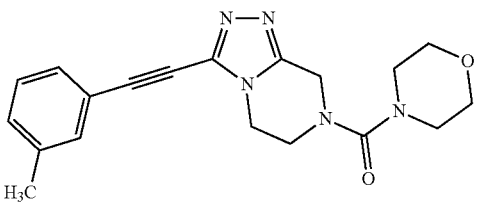

morpholino-[3-[2-(m-tolyl)ethynyl]-6,8-dihydro-5H-[1,2,4]triazolo[4,3-a]pyrazin-7-yl]methanone -continued

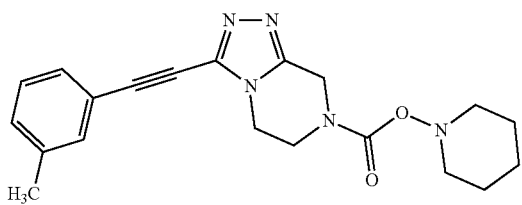 [SMILES: Cc1cccc(C#Cc2nnc3n2CCN(C(=O)ON2CCCCC2)C3)c1]

1-piperidyl 3-[2-(m-tolyl)ethynyl]-6,8-dihydro-5H-[1,2,4]triazolo[4,3-a]pyrazine-7-carboxylate

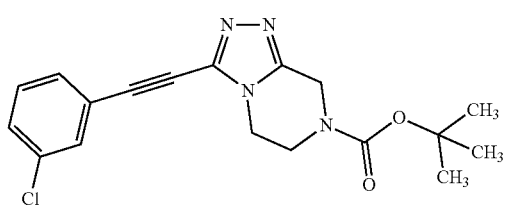 [SMILES: CC(C)(C)OC(=O)N1CCn2c(C#Cc3cccc(Cl)c3)nnc2C1]

tert-butyl 3-[2-(3-chlorophenyl)ethynyl]-6,8-dihydro-5H-[1,2,4]triazolo[4,3-a]pyrazine-7-carboxylate

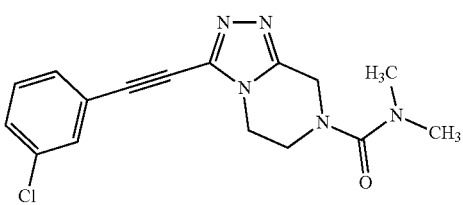 [SMILES: CN(C)C(=O)N1CCn2c(C#Cc3cccc(Cl)c3)nnc2C1]

3-[2-(3-chlorophenyl)ethynyl]-N,N-dimethyl-6,8-dihydro-5H-[1,2,4]triazolo[4,3-a]pyrazine-7-carboxamide

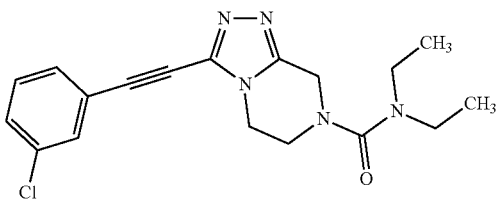 [SMILES: CCN(CC)C(=O)N1CCn2c(C#Cc3cccc(Cl)c3)nnc2C1]

3-[2-(3-chlorophenyl)ethynyl]-N,N-diethyl-6,8-dihydro-5H-[1,2,4]triazolo[4,3-a]pyrazine-7-carboxamide

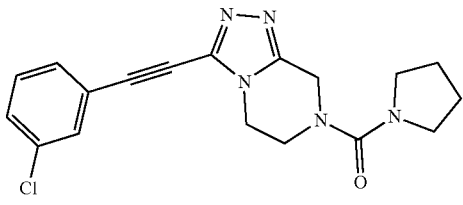 [SMILES: O=C(N1CCCC1)N1CCn2c(C#Cc3cccc(Cl)c3)nnc2C1]

[3-[2-(3-chlorophenyl)ethynyl]-6,8-dihydro-5H-[1,2,4]triazolo[4,3-a]pyrazin-7-yl]-pyrrolidin-1-yl-methanone -continued

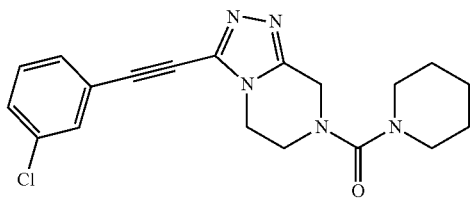 [SMILES: O=C(N1CCCCC1)N1CCn2c(C#Cc3cccc(Cl)c3)nnc2C1]

[3-[2-(3-chlorophenyl)ethynyl]-6,8-dihydro-5H-[1,2,4]triazolo[4,3-a]pyrazin-7-yl]-(1-piperidyl)methanone

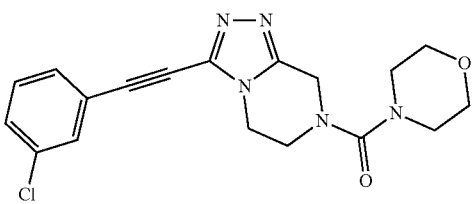 [SMILES: O=C(N1CCOCC1)N1CCn2c(C#Cc3cccc(Cl)c3)nnc2C1]

[3-[2-(3-chlorophenyl)ethynyl]-6,8-dihydro-5H-[1,2,4]triazolo[4,3-a]pyrazin-7-yl]-morpholino-methanone

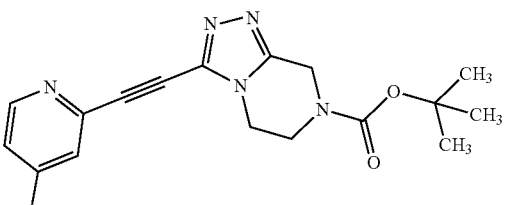

tert-butyl 3-[2-(4-chloro-2-pyridyl)ethynyl]-6,8-dihydro-5H-[1,2,4]triazolo[4,3-a]pyrazine-7-carboxylate

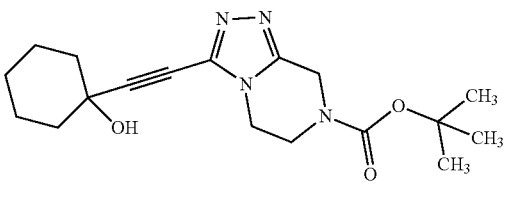 [SMILES: CC(C)(C)OC(=O)N1CCn2c(C#CC3(O)CCCCC3)nnc2C1]

tert-butyl 3-[2-(1-hydroxycyclohexyl)ethynyl]-6,8-dihydro-5H-[1,2,4]triazolo[4,3-a]pyrazine-7-carboxylate

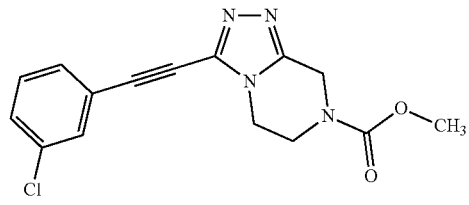 [SMILES: COC(=O)N1CCn2c(C#Cc3cccc(Cl)c3)nnc2C1]

methyl 3-[2-(3-chlorophenyl)ethynyl]-6,8-dihydro-5H-[1,2,4]triazolo[4,3-a]pyrazine-7-carboxylate

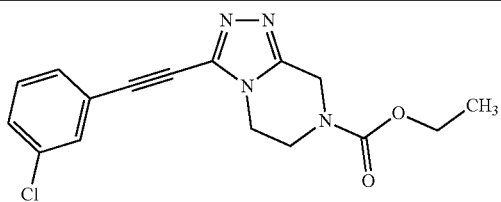

ethyl 3-[2-(3-chlorophenyl)ethynyl]-6,8-
dihydro-5H-[1,2,4]triazolo[4,3-a]pyrazine-
7-carboxylate

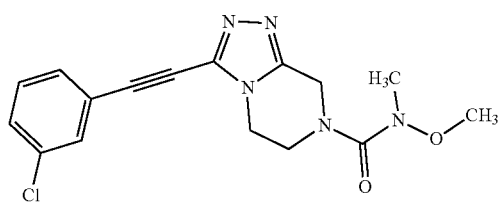 [SMILES: CON(C)C(=O)N1CCn2c(C#Cc3cccc(Cl)c3)nnc2C1]

3-[2-(3-chlorophenyl)ethynyl]-N-methoxy-
N-methyl-6,8-dihydro-5H-
[1,2,4]triazolo[4,3-a]pyrazine-7-
carboxamide

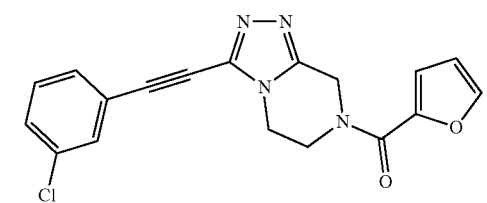 [SMILES: O=C(c1ccco1)N1CCn2c(C#Cc3cccc(Cl)c3)nnc2C1]

[3-[2-(3-chlorophenyl)ethynyl]-6,8-dihydro-
5H-[1,2,4]triazolo[4,3-a]pyrazin-7-yl]-(2-
furyl)methanone

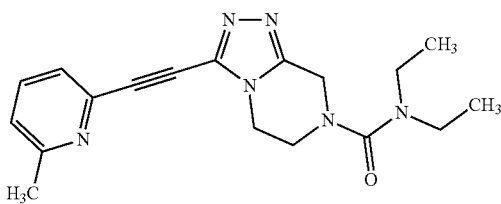 [SMILES: CCN(CC)C(=O)N1CCn2c(C#Cc3cccc(C)n3)nnc2C1]

N,N-diethyl-3-[2-(6-methyl-2-
pyridyl)ethynyl]-6,8-dihydro-5H-
[1,2,4]triazolo[4,3-a]pyrazine-7-
carboxamide

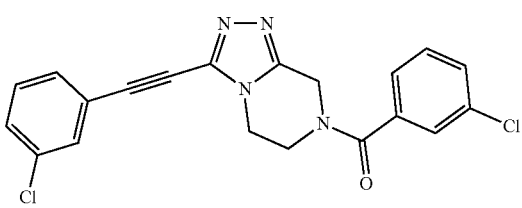 [SMILES: O=C(c1cccc(Cl)c1)N1CCn2c(C#Cc3cccc(Cl)c3)nnc2C1]

(3-chlorophenyl)-[3-[2-(3-
chlorophenyl)ethynyl]-6,8-dihydro-5H-
[1,2,4]triazolo[4,3-a]pyrazin-7-
yl]methanone

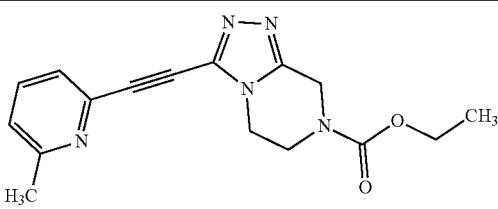

ethyl 3-[2-(6-methyl-2-pyridyl)ethynyl]-6,8-
dihydro-5H-[1,2,4]triazolo[4,3-a]pyrazine-7-
carboxylate

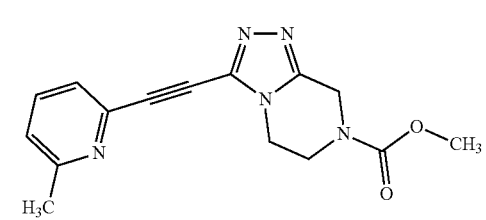 [SMILES: COC(=O)N1CCn2c(C#Cc3cccc(C)n3)nnc2C1]

methyl 3-[2-(6-methyl-2-pyridyl)ethynyl]-
6,8-dihydro-5H-[1,2,4]triazolo[4,3-
a]pyrazine-7-carboxylate

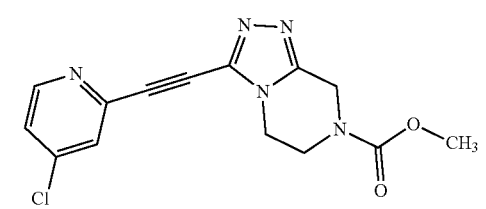 [SMILES: COC(=O)N1CCn2c(C#Cc3cc(Cl)ccn3)nnc2C1]

methyl 3-[2-(4-chloro-2-pyridyl)ethynyl]-
6,8-dihydro-5H-[1,2,4]triazolo[4,3-
a]pyrazine-7-carboxylate

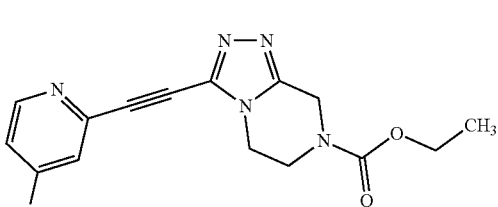

ethyl 3-[2-(4-chloro-2-pyridyl)ethynyl]-6,8-
dihydro-5H-[1,2,4]triazolo[4,3-a]pyrazine-
7-carboxylate

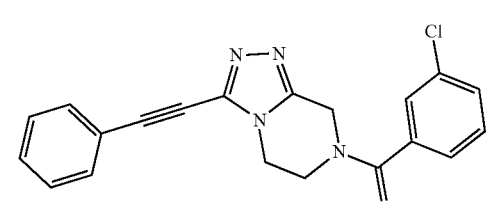

(3-chlorophenyl)-[3-(2-phenylethynyl)-6,8-
dihydro-5H-[1,2,4]triazolo[4,3-a]pyrazin-7-
yl]methanone -continued

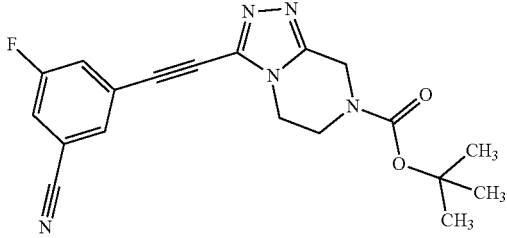 [SMILES: CC(C)(C)OC(=O)N1CCn2c(C#Cc3cc(F)cc(C#N)c3)nnc2C1]

tert-butyl 3-[2-(3-cyano-5-fluoro-
phenyl)ethynyl]-6,8-dihydro-5H-
[1,2,4]triazolo[4,3-a]pyrazine-7-
carboxylate

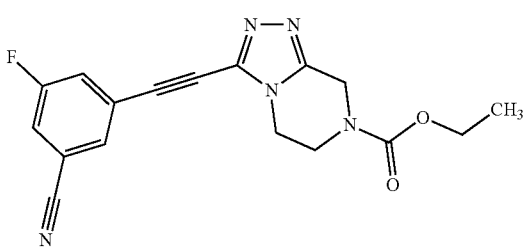 [SMILES: CCOC(=O)N1CCn2c(C#Cc3cc(F)cc(C#N)c3)nnc2C1]

ethyl 3-[2-(3-cyano-5-fluoro-
phenyl)ethynyl]-6,8-dihydro-5H-
[1,2,4]triazolo[4,3-a]pyrazine-7-carboxylate

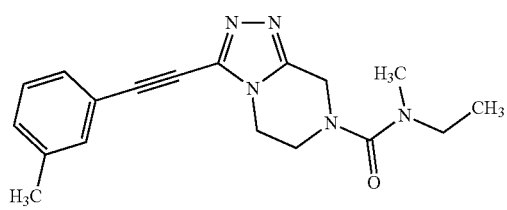 [SMILES: CCN(C)C(=O)N1CCn2c(C#Cc3cccc(C)c3)nnc2C1]

N-ethyl-N-methyl-3-[2-(m-tolyl)ethynyl]-
6,8-dihydro-5H-[1,2,4]triazolo[4,3-
a]pyrazine-7-carboxamide

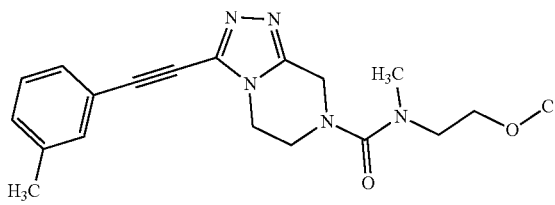

N-(2-methoxyethyl)-N-methyl-3-[2-(m-
tolyl)ethynyl]-6,8-dihydro-5H-
[1,2,4]triazolo[4,3-a]pyrazine-7-
carboxamide

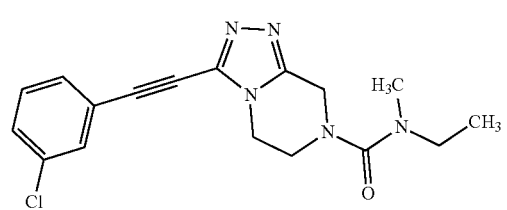

3-[2-(3-chlorophenyl)ethynyl]-N-ethyl-N-
methyl-6,8-dihydro-5H-[1,2,4]triazolo[4,3-
a]pyrazine-7-carboxamide -continued

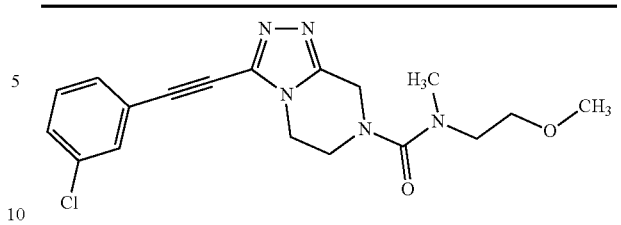

3-[2-(3-chlorophenyl)ethynyl]-N-(2-
methoxyethyl)-N-methyl-6,8-dihydro-5H-
[1,2,4]triazolo[4,3-a]pyrazine-7-
carboxamide

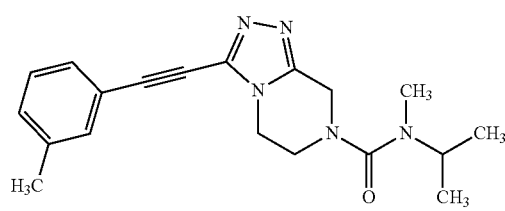 [SMILES: Cc1cccc(C#Cc2nnc3n2CCN(C(=O)N(C)C(C)C)C3)c1]

N-isopropyl-N-methyl-3-[2-(m-
tolyl)ethynyl]-6,8-dihydro-5H-
[1,2,4]triazolo[4,3-a]pyrazine-7-
carboxamide

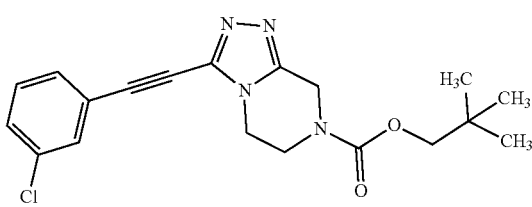 [SMILES: CC(C)(C)COC(=O)N1CCn2c(C#Cc3cccc(Cl)c3)nnc2C1]

2,2-dimethylpropyl 3-[2-(3-chlorophenyl)ethynyl]-
6,8-dihydro-5H-[1,2,4]triazolo[4,3-a]pyrazine-7-
carboxylate

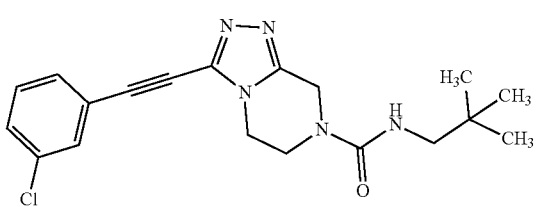 [SMILES: CC(C)(C)CNC(=O)N1CCn2c(C#Cc3cccc(Cl)c3)nnc2C1]

3-[2-(3-chlorophenyl)ethynyl]-N-(2,2-
dimethylpropyl)-6,8-dihydro-5H-[1,2,4]triazolo[4,3-
a]pyrazine-7-carboxamide

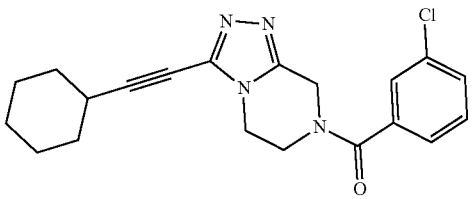 [SMILES: O=C(c1cccc(Cl)c1)N1CCn2c(C#CC3CCCCC3)nnc2C1]

(3-chlorophenyl)-[3-(2-cyclohexylethynyl)-6,8-
dihydro-5H-[1,2,4]triazolo[4,3-a]pyrazin-7-
yl]methanone

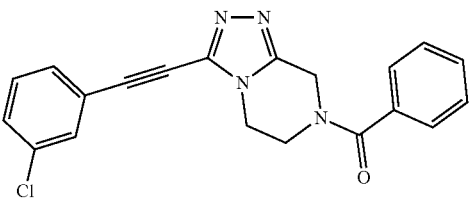 [SMILES: O=C(c1ccccc1)N1CCn2c(C#Cc3cccc(Cl)c3)nnc2C1]

[3-[2-(3-chlorophenyl)ethynyl]-6,8-dihydro-5H-
[1,2,4]triazolo[4,3-a]pyrazin-7-yl]-phenyl-
methanone

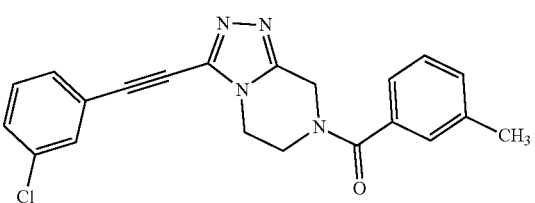 [SMILES: Cc1cccc(C(=O)N2CCn3c(C#Cc4cccc(Cl)c4)nnc3C2)c1]

[3-[2-(3-chlorophenyl)ethynyl]-6,8-dihydro-5H-
[1,2,4]triazolo[4,3-a]pyrazin-7-yl]-(m-
tolyl)methanone

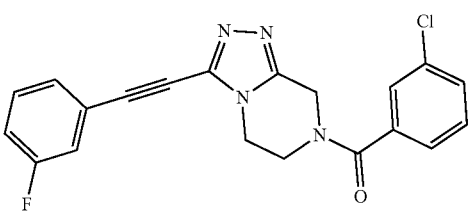 [SMILES: O=C(c1cccc(Cl)c1)N1CCn2c(C#Cc3cccc(F)c3)nnc2C1]

(3-chlorophenyl)-[3-[2-(3-fluorophenyl)ethynyl]-6,8-
dihydro-5H-[1,2,4]triazolo[4,3-a]pyrazin-7-
yl]methanone

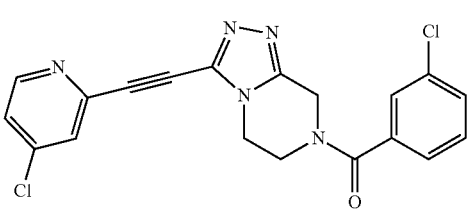 [SMILES: O=C(c1cccc(Cl)c1)N1CCn2c(C#Cc3cc(Cl)ccn3)nnc2C1]

(3-chlorophenyl)-[3-[2-(4-chloro-2-pyridyl)ethynyl]-
6,8-dihydro-5H-[1,2,4]triazolo[4,3-a]pyrazin-7-
yl]methanone

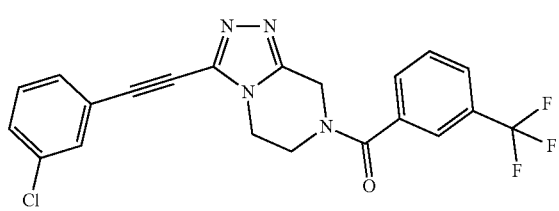 [SMILES: O=C(c1cccc(C(F)(F)F)c1)N1CCn2c(C#Cc3cccc(Cl)c3)nnc2C1]

[3-[2-(3-chlorophenyl)ethynyl]-6,8-dihydro-5H-
[1,2,4]triazolo[4,3-a]pyrazin-7-yl]-[3-
(trifluoromethyl)phenyl]methanone

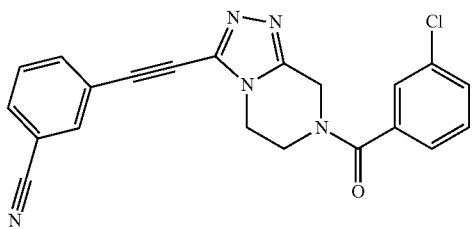 [SMILES: N#Cc1cccc(C#Cc2nnc3n2CCN(C(=O)c2cccc(Cl)c2)C3)c1]

3-[2-[7-(3-chlorobenzoyl)-6,8-dihydro-5H-
[1,2,4]triazolo[4,3-a]pyrazin-3-yl]ethynyl]benzonitrile

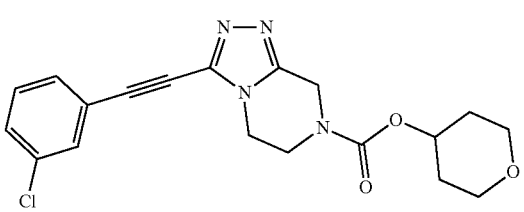 [SMILES: O=C(OC1CCOCC1)N1CCn2c(C#Cc3cccc(Cl)c3)nnc2C1]

tetrahydropyran-4-yl 3-[2-(3-chlorophenyl)ethynyl]-
6,8-dihydro-5H-[1,2,4]triazolo[4,3-a]pyrazine-7-
carboxylate

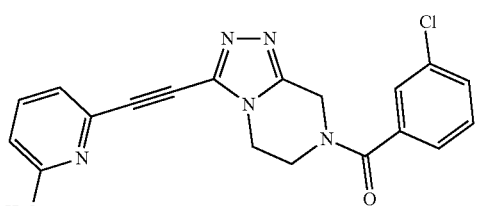

(3-chlorophenyl)-[3-[2-(6-methyl-2-pyridyl)ethynyl]-
6,8-dihydro-5H-[1,2,4]triazolo[4,3-a]pyrazin-7-
yl]methanone

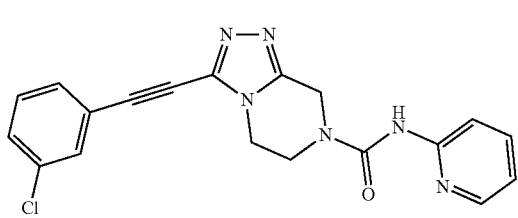 [SMILES: O=C(Nc1ccccn1)N1CCn2c(C#Cc3cccc(Cl)c3)nnc2C1]

3-[2-(3-chlorophenyl)ethynyl]-N-(2-pyridyl)-6,8-
dihydro-5H-[1,2,4]triazolo[4,3-a]pyrazine-7-
carboxamide

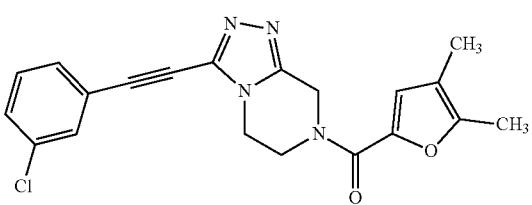 [SMILES: Cc1cc(C(=O)N2CCn3c(C#Cc4cccc(Cl)c4)nnc3C2)oc1C]

[3-[2-(3-chlorophenyl)ethynyl]-6,8-dihydro-5H-
[1,2,4]triazolo[4,3-a]pyrazin-7-yl]-(4,5-dimethyl-2-
furyl)methanone

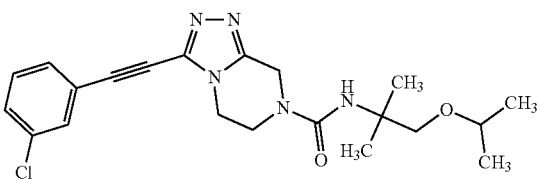 [SMILES: CC(C)OCC(C)(C)NC(=O)N1CCn2c(C#Cc3cccc(Cl)c3)nnc2C1]

3-[2-(3-chlorophenyl)ethynyl]-N-(2-isopropoxy-1,1-
dimethyl-ethyl)-6,8-dihydro-5H-[1,2,4]triazolo[4,3-
a]pyrazine-7-carboxamide

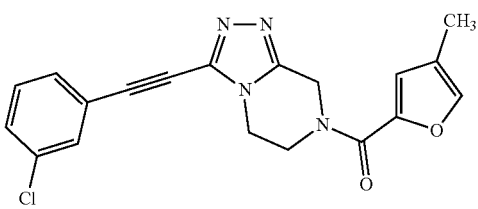 [SMILES: Cc1coc(C(=O)N2CCn3c(C#Cc4cccc(Cl)c4)nnc3C2)c1]

[3-[2-(3-chlorophenyl)ethynyl]-6,8-dihydro-5H-
[1,2,4]triazolo[4,3-a]pyrazin-7-yl]-(4-methyl-2-
furyl)methanone

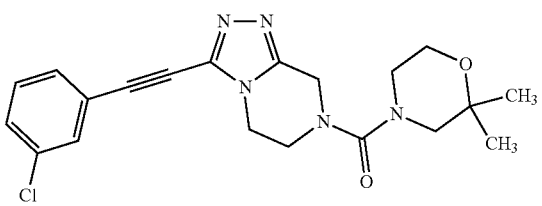 [SMILES: CC1(C)CN(C(=O)N2CCn3c(C#Cc4cccc(Cl)c4)nnc3C2)CCO1]

[3-[2-(3-chlorophenyl)ethynyl]-6,8-dihydro-5H-
[1,2,4]triazolo[4,3-a]pyrazin-7-yl]-(2,2-
dimethylmorpholin-4-yl)methanone

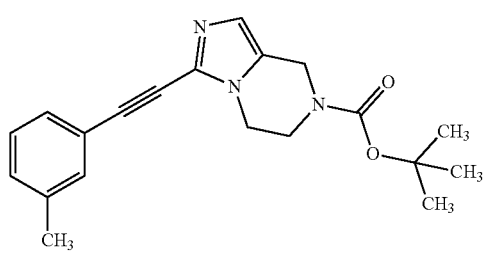 [SMILES: Cc1cccc(C#Cc2ncc3n2CCN(C(=O)OC(C)(C)C)C3)c1]

tert-butyl 3-[2-(m-tolyl)ethynyl]-6,8-dihydro-5H-
imidazo[1,5-a]pyrazine-7-carboxylate

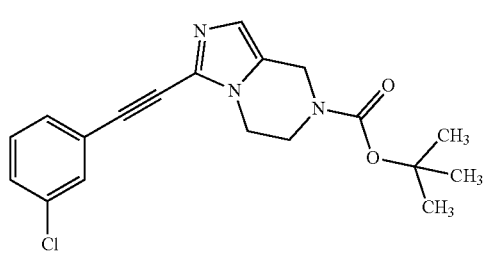 [SMILES: CC(C)(C)OC(=O)N1CCn2c(cnc2C#Cc2cccc(Cl)c2)C1]

tert-butyl 3-[2-(3-chlorophenyl)ethynyl]-6,8-
dihydro-5H-imidazo[1,5-a]pyrazine-7-carboxylate

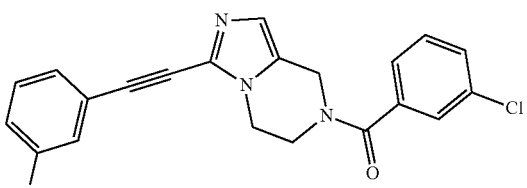

(3-chlorophenyl)-[3-[2-(3-chlorophenyl)ethynyl]-6,8-
dihydro-5H-imidazo[1,5-a]pyrazin-7-yl]methanone

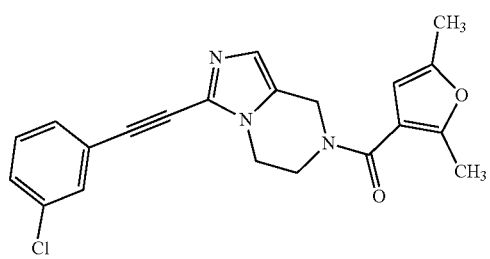 [SMILES: Cc1cc(C(=O)N2CCn3c(cnc3C#Cc3cccc(Cl)c3)C2)c(C)o1]

[3-[2-(3-chlorophenyl)ethynyl]-6,8-dihydro-5H-
imidazo[1,5-a]pyrazin-7-yl]-(2,5-dimethyl-3-
furyl)methanone

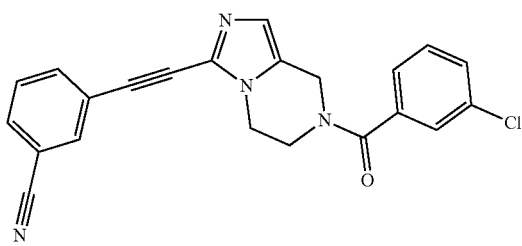 [SMILES: N#Cc1cccc(C#Cc2ncc3n2CCN(C(=O)c2cccc(Cl)c2)C3)c1]

3-[2-[7-(3-chlorobenzoyl)-6,8-dihydro-5H-
imidazo[1,5-a]pyrazin-3-yl]ethynyl]benzonitrile

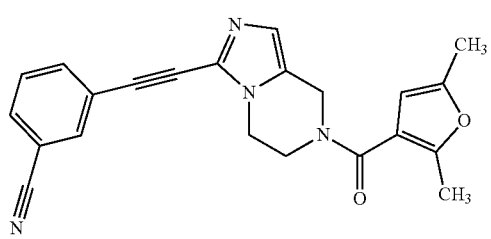 [SMILES: Cc1cc(C(=O)N2CCn3c(cnc3C#Cc3cccc(C#N)c3)C2)c(C)o1]

3-[2-[7-(2,5-dimethylfuran-3-carbonyl)-6,8-dihydro-
5H-imidazo[1,5-a]pyrazin-3-yl]ethynyl]benzonitrile

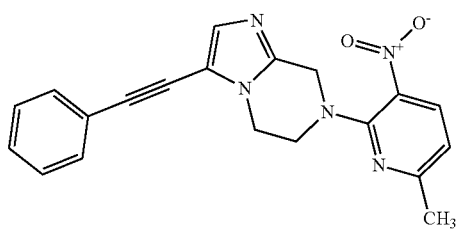 [SMILES: Cc1ccc([N+](=O)[O-])c(N2CCn3c(C#Cc4ccccc4)cnc3C2)n1]

7-(6-methyl-3-nitro-2-pyridyl)-3-(2-phenylethynyl)-
6,8-dihydro-5H-imidazo[1,2-a]pyrazine

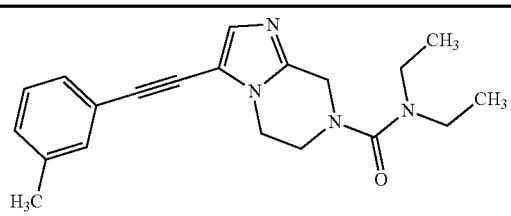

N,N-diethyl-3-[2-(m-tolyl)ethynyl]-6,8-dihydro-5H-
imidazo[1,2-a]pyrazine-7-carboxamide

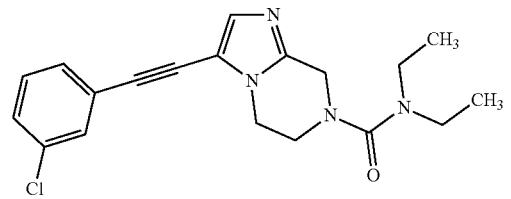 [SMILES: CCN(CC)C(=O)N1CCn2c(C#Cc3cccc(Cl)c3)cnc2C1]

3-[2-(3-chlorophenyl)ethynyl]-N,N-diethyl-6,8-
dihydro-5H-imidazo[1,2-a]pyrazine-7-carboxamide

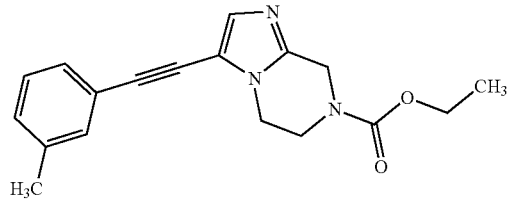 [SMILES: CCOC(=O)N1CCn2c(C#Cc3cccc(C)c3)cnc2C1]

ethyl 3-[2-(m-tolyl)ethynyl]-6,8-dihydro-5H-
imidazo[1,2-a]pyrazine-7-carboxylate

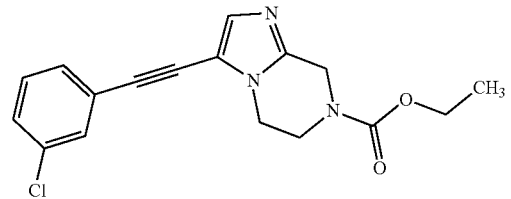 [SMILES: CCOC(=O)N1CCn2c(C#Cc3cccc(Cl)c3)cnc2C1]

ethyl 3-[2-(3-chlorophenyl)ethynyl]-6,8-dihydro-5H-
imidazo[1,2-a]pyrazine-7-carboxylate

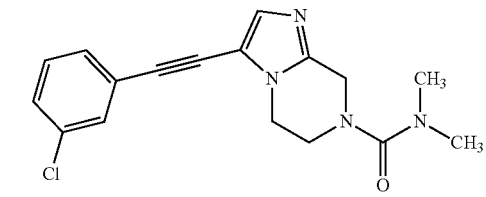 [SMILES: CN(C)C(=O)N1CCn2c(C#Cc3cccc(Cl)c3)cnc2C1]

3-[2-(3-chlorophenyl)ethynyl]-N,N-dimethyl-6,8-
dihydro-5H-imidazo[1,2-a]pyrazine-7-carboxamide

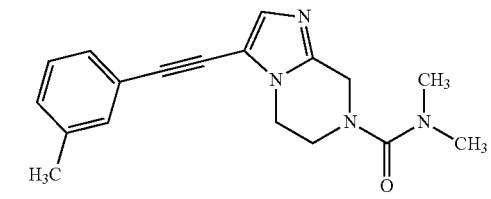 [SMILES: Cc1cccc(C#Cc2cnc3n2CCN(C(=O)N(C)C)C3)c1]

N,N-dimethyl-3-[2-(m-tolyl)ethynyl]-6,8-dihydro-5H-
imidazo[1,2-a]pyrazine-7-carboxamide

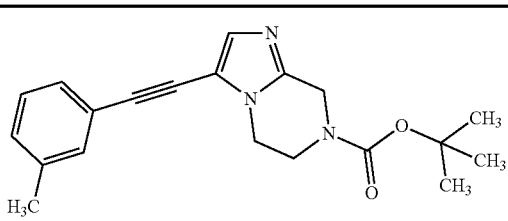

tert-butyl 3-[2-(m-tolyl)ethynyl]-6,8-dihydro-5H-
imidazo[1,2-a]pyrazine-7-carboxylate

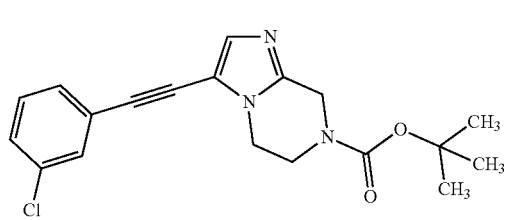 [SMILES: CC(C)(C)OC(=O)N1CCn2c(C#Cc3cccc(Cl)c3)cnc2C1]

tert-butyl 3-[2-(3-chlorophenyl)ethynyl]-6,8-dihydro-
5H-imidazo[1,2-a]pyrazine-7-carboxylate

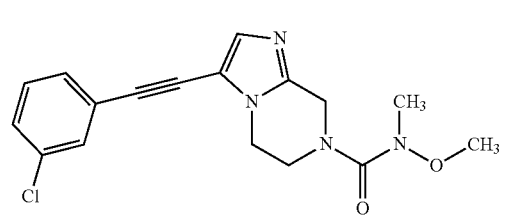 [SMILES: CON(C)C(=O)N1CCn2c(C#Cc3cccc(Cl)c3)cnc2C1]

3-[2-(3-chlorophenyl)ethynyl]-N-methoxy-N-
methyl-6,8-dihydro-5H-imidazo[1,2-a]pyrazine-7-
carboxamide

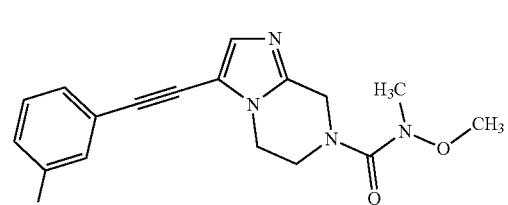

N-methoxy-N-methyl-3-[2-(m-tolyl)ethynyl]-6,8-
dihydro-5H-imidazo[1,2-a]pyrazine-7-carboxamide

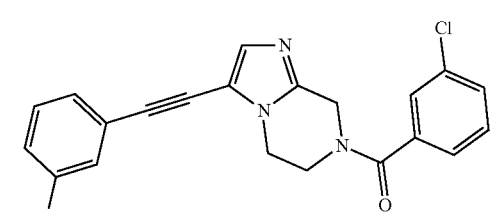

(3-chlorophenyl)-[3-[2-(3-chlorophenyl)ethynyl]-
6,8-dihydro-5H-imidazo[1,2-a]pyrazin-7-
yl]methanone

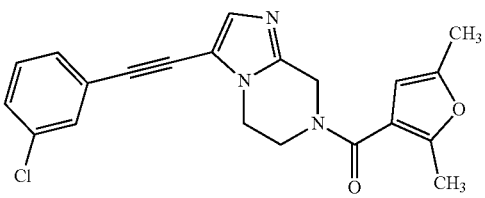 [SMILES: Cc1cc(C(=O)N2CCn3c(C#Cc4cccc(Cl)c4)cnc3C2)c(C)o1]

[3-[2-(3-chlorophenyl)ethynyl]-6,8-dihydro-5H-imidazo[1,2-a]pyrazin-7-yl]-(2,5-dimethyl-3-furyl)methanone

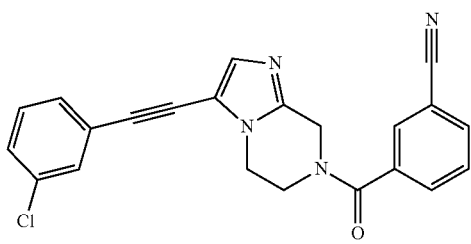 [SMILES: N#Cc1cccc(C(=O)N2CCn3c(C#Cc4cccc(Cl)c4)cnc3C2)c1]

3-[3-[2-(3-chlorophenyl)ethynyl]-6,8-dihydro-5H-imidazo[1,2-a]pyrazine-7-carbonyl]benzonitrile

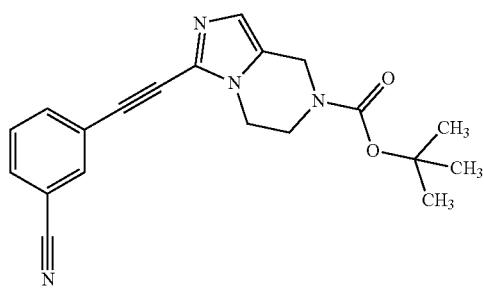 [SMILES: CC(C)(C)OC(=O)N1CCn2c(cnc2C#Cc2cccc(C#N)c2)C1]

tert-butyl 3-[2-(3-cyanophenyl)ethynyl]-6,8-dihydro-5H-imidazo[1,2-a]pyrazine-7-carboxylate

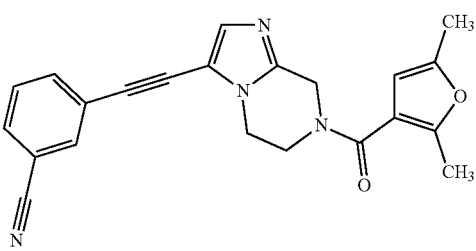 [SMILES: Cc1cc(C(=O)N2CCn3c(C#Cc4cccc(C#N)c4)cnc3C2)c(C)o1]

3-[2-[7-(2,5-dimethylfuran-3-carbonyl)-6,8-dihydro-5H-imidazo[1,2-a]pyrazin-3-yl]ethynyl]benzonitrile

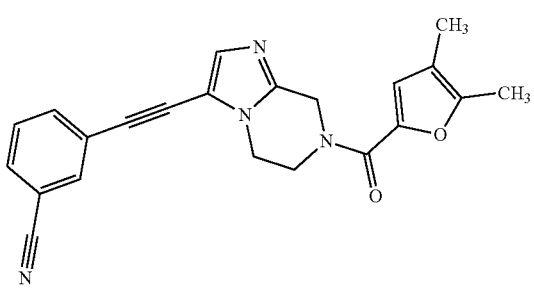 [SMILES: Cc1cc(C(=O)N2CCn3c(C#Cc4cccc(C#N)c4)cnc3C2)oc1C]

3-[2-[7-(4,5-dimethylfuran-2-carbonyl)-6,8-dihydro-5H-imidazo[1,2-a]pyrazin-3-yl]ethynyl]benzonitrile

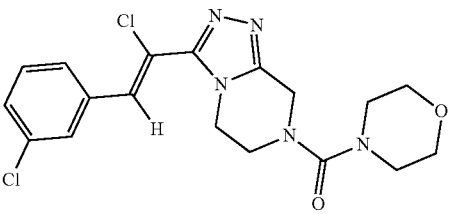 [SMILES: O=C(N1CCOCC1)N1CCn2c(nnc2/C(Cl)=C/c2cccc(Cl)c2)C1]

[3-[(Z)-1-chloro-2-(3-chlorophenyl)vinyl]-6,8-dihydro-5H-[1,2,4]triazolo[4,3-a]pyrazin-7-yl]-morpholino-methanone In a further embodiment of the invention, a pharmaceutical composition is preferably provided comprising a compound of Formula I,

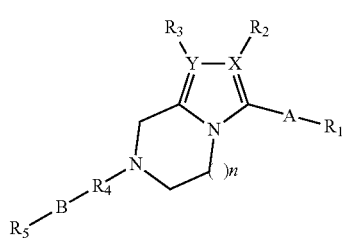

(I)

or an enantiomer, diastereomer, N-oxide, or a pharmaceutically acceptable salt thereof, and a pharmaceutically acceptable carrier, wherein n, $R_1$ through $R_6$, A, and B have the meanings ascribed to them above; and, in a more specific embodiment,
a compound of Formula IA:

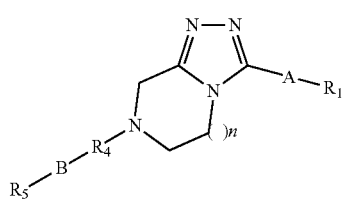

IA or an enantiomer, diastereomer, N-oxide, or a pharmaceutically acceptable salt thereof, for use in the treatment and/or prevention of a neurological disorder, psychotic disorder, pain or a psychiatric disorder associated with glutamate dysfunction is preferably provided.

In an embodiment of the invention, a compound according to Formula I or IA is used in the treatment and/or prevention of a neurological disorder, psychotic disorder, or a psychiatric disorder associated with glutamate dysfunction including without any limitation for mGlu$_5$ positive allosteric modulators: Rett's syndrome, Phelan-McDermid syndrome, psychosis, schizophrenia, autism cognitive disorders, tuberous sclerosis, cognition disorders, Alzheimer's dementia, and for mGlu$_5$ negative allosteric modulators: addiction, major depressive disorder, anxiety, epilepsy, Fragile X syndrome, gastroesophageal reflux disease (GERD), substance abuse and dependence, Parkinson's disease and L-Dopa induced dyskinesia, urinary incontinence, irritable bowel syndrome (IBS) and pain.

Preferably the neurological disorder, psychotic disorder, or psychiatric disorder associated with glutamate dysfunction is schizophrenia, schizoaffective disorder, substance induced psychotic disorder, age-associated learning and memory impairments or losses, post stroke dementia, deficits in concentration, mild cognitive impairment, cognitive dysfunction in Alzheimer's disease, cognitive dysfunction of schizophrenia, cognitive decline, dementia or cognitive impairment.

More preferably, the disorder is Fragile-X syndrome, Rett syndrome, Phelan-McDermid syndrome, or tuberous sclerosis.

DETAILED DESCRIPTION OF THE INVENTION

Terms and Definitions Used

Except where stated otherwise, the following definitions apply throughout the present specification and claims. These definitions apply regardless of whether a term is used by itself or in combination with other terms. For example, the definition of "alkyl" applies not only to alkyl groups per se, but also to the alkyl portions of alkoxy, alkylamino, alkylthio or alkylcarbonyl groups etc. Furthermore, all ranges described for a chemical group, for example "from 1 to 13 carbon atoms" or "$C_1$-$C_6$ alkyl" include all combinations and sub-combinations of ranges and specific numbers of carbon atoms therein.

"Alkyl" means a straight chain or branched chain aliphatic hydrocarbon group having from 1 to 20 carbon atoms in the chain. Preferred alkyl groups have from 1 to 12 carbon atoms in the chain. More preferred alkyl groups have from 1 to 6 carbon atoms in the chain. "Lower alkyl" means an alkyl group having about 1 to about 6 carbon atoms in the chain which may be straight or branched. Examples of suitable alkyl groups include methyl, ethyl, n-propyl, isopropyl, sec-butyl, n-butyl, and t-butyl.

"Alkenyl" means a straight chain or branched chain aliphatic hydrocarbon group having at least one carbon-carbon double bond and having from 2 to 15 carbon atoms in the chain.

Preferred alkenyl groups have from 2 to 12 carbon atoms in the chain. More preferred alkenyl groups have from 2 to 6 carbon atoms in the chain. "Lower alkenyl" means an alkenyl group having 2 to about 6 carbon atoms in the chain, which may be straight or branched. Examples of suitable alkenyl groups include ethenyl, propenyl, isopropenyl, n-butenyl, 1-hexenyl and 3-methylbut-2-enyl.

"Alkynyl" means a straight chain or branched chain aliphatic hydrocarbon group having at least one carbon-carbon triple bond and having from 2 to 15 carbon atoms in the chain.

Preferred alkynyl groups have from 2 to 12 carbon atoms in the chain. More preferred alkynyl groups have from 2 to 6 carbon atoms in the chain. "Lower alkynyl" means an alkynyl group having 2 to about 6 carbon atoms in the chain, which may be straight or branched. Examples of suitable alkynyl groups include ethynyl, propynyl and 2-butynyl.

"Mono-, bi-, or tricyclic heterocyclic" means an aromatic or non-aromatic saturated mono- bi- or tricyclic ring system having from 2 to 14 ring carbon atoms and containing from 1 to 5 ring atoms selected from N, O and S, alone or in combination. Bi- and tricyclic heterocyclic groups are fused at 2 or 4 points or joined at one point via a bond or a heteroatom linker (O, S, NH, or N($C_1$-$C_6$ alkyl). The "mono- bi- or tricyclic heterocyclic" can be optionally substituted on the ring by replacing an available hydrogen on the ring by one or more substituents which may be the same or different. The nitrogen or sulphur atom of the heterocyclic can be optionally oxidized to the corresponding N-oxide, S-oxide or S-dioxide. Examples of suitable heterocyclics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl and benzoisoxazolyl, aziridinyl, piperidinyl, pyrrolidinyl, piperazinyl, tetrahydropyranyl, tetrahydrofuranyl, tetrahydrothiophenyl, morpholinyl and thiomorpholinyl.

Heterocyclics with aromatic characteristics may be referred to as heteroaryls or heteroaromatics. Examples of suitable heteroaromatics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisoxazolyl, tetrahydroquinolinyl, tetrahydroisoquinolinyl, 3-phenylpyridine, 3-cyclohexylpyridine, 3-(pyridin-3-yl) morpholine, 3-phenylisoxazole and 2-(piperidin-1-yl)pyrimidine.

"Mono-, bi- or tricyclic aryl" means an aromatic monocyclic, bicyclic or tricyclic ring system comprising 6 to 14 carbon atoms. Bi- and tricyclic aryl groups are fused at 2 or 4 points or joined at one point via a bond or a heteroatom linker (O, S, NH, or N($C_1$-$C_6$ alkyl) (e.g., biphenyl, 1-phenylnapthyl). The aryl group can be optionally substituted on the ring with one or more substituents, preferably 1 to 6 substituents, which may be the same or different. Examples of suitable aryl groups include phenyl and naphthyl.

"Cycloalkyl" means a monocyclic or bicyclic carbon ring system having from 3 to 14 carbon atoms, preferably from 3 to 6 carbon atoms. The cycloalkyl can be optionally substituted on the ring by replacing an available hydrogen on the ring by one or more substituents which may be the same or different. Examples of suitable monocyclic cycloalkyls include cyclopropyl, cyclopentyl, cyclohexyl and cycloheptyl. Examples of suitable multicyclic cycloalkyls include 1-decalinyl, norbornyl and adamantyl.

"Cycloalkenyl" has a meaning corresponding to that of cycloalkyl, but with one or two double bonds within the ring (e.g., cyclohexenyl, cyclohexadiene).

"Amines" are derivatives of ammonia, wherein one or more hydrogen atoms have been replaced by a substituent such as an alkyl or aryl group. These may respectively be called alkylamines and arylamines; amines in which both types of substituent are attached to one nitrogen atom may be called alkylarylamines.

Amines can be further organized into four sub-categories. Primary amines arise when one of the three hydrogen atoms in ammonia is replaced by an alkyl or aromatic group (an N-alkylamino or N-arylamino respectively). Examples of suitable primary alkyl amines include methylamine or ethanolamine, or aniline (phenylamine) as an example of an aromatic amine. Secondary amines have two organic substituents (independently alkyl or aryl groups) bound to the nitrogen atom together with one hydrogen (or no hydrogen if one of the substituent bonds is double). Examples of suitable secondary amines include dimethylamine and methylethanolamine, while an example of an aromatic amine would be diphenylamine. Such compounds may also be referred to as "N,N-dialkylamino", "N,N-diarylamino" or "N,N-alkylarylamino" groups depending on the nature of the substituents. A secondary amine substituted by an alkoxy group, as defined herein, would be termed an "N-alkyl-N-alkoxyamino" compound for example. In tertiary amines, all three hydrogen atoms are replaced by organic substituents, such as trimethylamine. The final sub-category is cyclic amines which are either secondary or tertiary amines. Examples of suitable cyclic amines include the 3-member ring aziridine and the six-membered ring piperidine. N-methylpiperidine and N-phenylpiperidine are suitable examples of cyclic tertiary amines.

"Amides" are compounds with a nitrogen atom attached to a carbonyl group, thus having the structure R—CO—NR'R", with groups R' and R" being independently selected from alkyl or aromatic groups as defined herein. For example, when R' is hydrogen and R" is a 3-pyridyl group, the resulting amide has a 3-pyridylamino substituent. Alternatively, when R' is hydrogen and R" is a cyclopentyl group, the resulting amide has a cyclopentylamino substituent.

"Halogen", "halide" or "halo" means fluorine, chlorine, bromine or iodine. Preferred halogens are fluorine, chlorine or bromine, and most preferred are fluorine and chlorine.

The term "acyl", whether used alone, or within a term such as "acylamino", denotes a radical provided by the residue after removal of hydroxyl from an organic acid. The term "acylamino" refers to an amino radical substituted with an acyl group. An example of an "acylamino" radical is $CH_3C(=O)$—NH— where the amine may be further substituted with alkyl, aryl or aralkyl groups.

An asterisk may be used in subgeneric-formulas or groups to indicate the bond which is connected to a parent or core molecule as defined herein.

The term "treatment" and the like as used herein encompasses eliminating or alleviating symptoms and/or markers of mGluR5-mediated diseases or disorders or and keeping them from worsening (stabilization) and more generally bringing about a desired physiological or pharmacological effect. The term "prevention" and the like as used herein encompasses inhibiting or retarding the manifestation of symptoms of such diseases or disorders or reducing (or increasing as the case may be) or eliminating abnormal values in markers therefor.

Stereochemistry

Unless specifically indicated, throughout the specification and claims, a given chemical formula or name shall encompass tautomers and all stereo, optical and geometrical isomers (e.g. enantiomers, diastereomers, +/−, R/S, E/Z isomers etc.) racemic mixtures and racemates thereof. This includes mixtures in different proportions of the separate enantiomers, mixtures of diastereomers, or mixtures of any of the foregoing forms where such isomers and enantiomers exist, as well as salts, including pharmaceutically acceptable salts and solvates thereof such as hydrates, solvates of the free compounds or solvates of a salt of the compound.

Derivatives of Compounds of the Invention

The invention further encompasses salts, solvates, hydrates, N-oxides, produgs and active metabolites of the compounds of formula I.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals such as aluminium, calcium, lithium, magnesium, potassium, sodium, zinc and the like (see Pharmaceutical salts, Berge, S. M. et al., *J. Pharm. Sci.*, (1977), Vol. 66, pp. 1-19).

Pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoro acetate salts), also comprise a part of the invention.

Typically, a pharmaceutically acceptable salt of a compound of formula I may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I and the resulting mixture evaporated to dryness (lyophilized) to obtain the acid addition salt as a solid. Alternatively, a compound of formula I may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of the compounds of formula I may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the invention.

Also included are both total and partial salts, i.e., salts with 1, 2 or 3, preferably 2, equivalents of base per mole of acid of formula I or salts with 1, 2 or 3 equivalents, preferably 1 equivalent, of acid per mole of base of formula I.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of said acidic compounds are prepared by contacting the free acid form with a sufficient amount of the desired base to produce the salt in the conventional manner.

The free acid form may be regenerated by contacting the salt form with an acid and isolating the free acid.

Compounds of the invention may have both a basic and an acidic center and may therefore be in the form of zwitterions or internal salts.

Typically, a pharmaceutically acceptable salt of a compound of formula I may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I and the resulting mixture evaporated to dryness (lyophilized) to obtain the acid addition salt as a solid. Alternatively, a compound of formula I may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the compound of formula I may form solvates (e.g., hydrates) and the invention also includes all such solvates. The meaning of the word "solvates" is well known to those skilled in the art as a compound formed by interaction of a solvent and a solute (i.e., solvation). Techniques for the preparation of solvates are well established in the art (see, for example, Brittain. *Polymorphism in Pharmaceutical solids*. Marcel Decker, New York, 1999).

The invention also encompasses N-oxides of the compounds of formula I. The term "N-oxide" means that for heterocycles containing an otherwise unsubstituted $sp^2$ N atom, the N atom may bear a covalently bound O atom, i.e., —N→O. Examples of such N-oxide substituted heterocycles include pyridyl N-oxides, pyrimidyl N-oxides, pyrazinyl N-oxides and pyrazolyl N-oxides.

The invention also encompasses prodrugs of the compounds of formula I, i.e., compounds which release an active parent drug according to formula I in vivo when administered to a mammalian subject. A prodrug is a pharmacologically active or more typically an inactive compound that is converted into a pharmacologically active agent by a metabolic transformation. Prodrugs of a compound of formula I are prepared by modifying functional groups present in the compound of formula I in such a way that the modifications may be cleaved in vivo to release the parent compound. In vivo, a prodrug readily undergoes chemical changes under physiological conditions (e.g., are acted on by naturally occurring enzyme(s)) resulting in liberation of the pharmacologically active agent. Prodrugs include compounds of formula I wherein a hydroxy, amino, or carboxy group of a formula I compound is bonded to any group that may be cleaved in vivo to regenerate the free hydroxyl, amino or carboxy group, respectively. Examples of prodrugs include esters (e.g., acetate, formate, and benzoate derivatives) of compounds of formula I or any other derivative which upon being brought to the physiological pH or through enzyme action is converted to the active parent drug. Conventional procedures for the selection and preparation of suitable prodrug derivatives are described in the art (see, for example, Bundgaard. *Design of Prodrugs*. Elsevier, 1985). Prodrugs may be administered in the same manner as and in effective amounts analogous to the active ingredient to which they convert, or they may be delivered in a reservoir form, e.g., a transdermal patch or other reservoir which is adapted to permit (by provision of an enzyme or other appropriate reagent) conversion of a prodrug to the active ingredient slowly over time, and delivery of the active ingredient to the patient.

The invention also encompasses metabolites. A "metabolite" of a compound disclosed herein is a derivative of a compound which is formed when the compound is metabolized. The term "active metabolite" refers to a biologically active derivative of a compound which is formed when the compound is metabolized. The term "metabolized" refers to the sum of the processes by which a particular substance is changed in the living body. In brief, all compounds present in the body are manipulated by enzymes within the body in order to derive energy and/or to remove them from the body. Specific enzymes produce specific structural alterations to the compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996), pages 11-17.

Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Pharmaceutical Compositions Comprising a Compound of Formula I, IA, IB or IC

While it is possible that a compound I may be administered as the bulk substance, it is preferable to present the active ingredient in a pharmaceutical formulation, e.g., wherein the agent is in admixture with a pharmaceutically acceptable carrier selected with regard to the intended route of administration and standard pharmaceutical practice.

Accordingly, the invention further provides a pharmaceutical composition comprising a compound of formula I or a solvate, hydrate, isomer (e.g., enantiomer, diastereomer, etc.), N-oxide or pharmaceutically acceptable salt thereof in admixture with a pharmaceutically acceptable carrier. The term "carrier" refers to a diluent, excipient, and/or vehicle with which an active compound is administered.

A compound of formula I may be used in combination with other therapies and/or active agents. Accordingly, the invention provides, in a further aspect, a pharmaceutical composition comprising a compound of formula I or a solvate, hydrate, isomer (e.g., enantiomer, diastereomer, etc.), N-oxide or pharmaceutically acceptable salt thereof, a second active agent, and a pharmaceutically acceptable carrier.

The pharmaceutical compositions may comprise as, in addition to, the carrier any suitable binder, lubricant, suspending agent, coating agent and/or solubilizing agent.

Preservatives, stabilizers, dyes and flavoring agents also may be provided in the pharmaceutical composition. Antioxidants and suspending agents may be also used.

The compounds of the invention may be reduced to fine particulate form (e.g., milled using known milling procedures such as wet milling) to obtain a particle size appropriate for tablet formation and for other formulation types. Finely divided (nanoparticulate) preparations of the compounds of the invention may be prepared by processes known in the art, for example see WO02/00196, incorporated by reference herein.

Routes of Administration and Unit Dosage Forms

The routes for administration include oral (e.g., as a tablet, capsule, or as an ingestible solution), topical, mucosal (e.g., as a nasal spray or aerosol for inhalation), nasal, parenteral (e.g., by an injectable form), gastrointestinal, intraspinal, intraperitoneal, intramuscular, intravenous, intrauterine, intraocular, intradermal, intracranial, intrathecal, intratracheal, intravaginal, intracerebroventricular, intracerebral, subcutaneous, ophthalmic (including intravitreal or intracameral), transdermal, rectal, buccal, epidural and sublingual. The compositions of the invention may be especially formulated for any of those administration routes. In preferred embodiments, the pharmaceutical compositions of the invention are formulated in a form that is suitable for oral delivery.

There may be different composition/formulation requirements depending on the different delivery systems. It is to be understood that not all of the compounds need to be administered by the same route. Likewise, if the composition comprises more than one active component, then those components may be administered by different routes. By way of example, the pharmaceutical composition of the invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile. For example, the compound of Formula I may be coated with an enteric coating layer.

The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

When appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavoring or coloring agents, or they can be injected parenterally, for example intravenously, intramuscularly or subcutaneously.

For buccal or sublingual administration, the compositions may be administered in the form of tablets or lozenges, which can be formulated in a conventional manner.

When the composition of the invention is to be administered parenterally, such administration includes one or more of: intravenously, intraarterially, intraperitoneally, intrathecally, intraventricularly, intraurethrally, intrasternally, intracranially, intramuscularly or subcutaneously administering the agent; and/or by using infusion techniques.

Pharmaceutical compositions of the invention can be administered parenterally, e.g., by infusion or injection. Pharmaceutical compositions suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, sodium acetate, sodium lactate, sodium citrate or acsorbic acid. In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminium monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound of formula I with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the aldosterone receptor antagonists and desired excipients for subsequent preparation of sterile solutions.

The compounds according to the invention may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary with an added preservative.

The compositions for injection may be in the form of suspensions, solutions, or emulsions, in oily or aqueous vehicles, and may contain formulatory agents such as suspending, stabilizing, solubilizing and/or dispersing agents. Alternatively, the active ingredient may be in sterile powder form for reconstitution with a suitable vehicle, e.g., sterile, pyrogen-free water, before use.

The compounds of the invention can be administered (e.g., orally or topically) in the form of tablets, capsules, ovules, elixirs, solutions or suspensions, which may contain flavoring or coloring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavoring and coloring agents. Solid compositions such as tablets, capsules, lozenges, pastilles, pills, boluses, powder, pastes, granules, bullets or premix preparations may also be used. Solid and liquid compositions for oral use may be prepared according to methods well-known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The compositions may be administered orally, in the form of rapid or controlled release tablets, microparticles, mini tablets, capsules, sachets, and oral solutions or suspensions, or powders for the preparation thereof. In addition to the new solid-state forms of pantoprazole of the invention as the active substance, oral preparations may optionally include various standard pharmaceutical carriers and excipients, such as binders, fillers, buffers, lubricants, glidants, dyes, disintegrants, odorants, sweeteners, surfactants, mold release agents, antiadhesive agents and coatings. Some excipients may have multiple roles in the compositions, e.g., act as both binders and disintegrants.

Examples of pharmaceutically acceptable disintegrants for oral compositions include starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral compositions include acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include lactose, anhydrolactose, lactose mono-hydrate, sucrose, dextrose, mannitol, sorbitol, starch, cellulose (particularly microcrystalline cellulose), dihydro- or anhydro-calcium phosphate, calcium carbonate and calcium sulphate.

Examples of pharmaceutically acceptable lubricants useful in the compositions of the invention include magnesium stearate, talc, polyethylene glycol, polymers of ethylene oxide, sodium lauryl sulphate, magnesium lauryl sulphate, sodium oleate, sodium stearyl fumarate, and colloidal silicon dioxide.

Examples of suitable pharmaceutically acceptable odorants for the oral compositions include synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include synthetic and natural dyes such as titanium dioxide, beta-carotene and extracts of grapefruit peel.

Examples of useful pharmaceutically acceptable coatings for the oral compositions, typically used to facilitate swallowing, modify the release properties, improve the appearance, and/or mask the taste of the compositions include hydroxypropylmethylcellulose, hydroxypropylcelluloseandacrylate-methacrylatecopolymers.

Examples of pharmaceutically acceptable sweeteners for the oral compositions include aspartame, saccharin, saccharin sodium, sodium cyclamate, xylitol, mannitol, sorbitol, lactose and sucrose.

Examples of pharmaceutically acceptable buffers include citric acid, sodium citrate, sodium bicarbonate, dibasic sodium phosphate, magnesium oxide, calcium carbonate and magnesium hydroxide.

Examples of pharmaceutically acceptable surfactants include sodium lauryl sulphate and polysorbates.

Solid compositions of a similar type may also be employed as fillers in gelatin capsules.

Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

The compounds of the invention may also, for example, be formulated as suppositories e.g., containing conventional suppository bases for use in human or veterinary medicine or as pessaries e.g., containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the agent of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colorants, and odorants.

Examples of pharmaceutically acceptable polymers suitable for such topical compositions include acrylic polymers; cellulose derivatives, such as carboxymethylcellulose sodium, methylcellulose or hydroxypropylcellulose; natural polymers, such as alginates, tragacanth, pectin, xanthan and cytosan.

Examples of suitable pharmaceutically acceptable oils which are so useful include mineral oils, silicone oils, fatty acids, alcohols, and glycols.

Examples of suitable pharmaceutically acceptable liquid carriers include water, alcohols or glycols such as ethanol, isopropanol, propylene glycol, hexylene glycol, glycerol and polyethylene glycol, or mixtures thereof in which the pseudopolymorph is dissolved or dispersed, optionally with the addition of non-toxic anionic, cationic or non-ionic surfactants, and inorganic or organic buffers.

Examples of pharmaceutically acceptable preservatives include sodium benzoate, ascorbic acid, esters of p-hydroxybenzoic acid and various antibacterial and antifungal agents such as solvents, for example ethanol, propylene glycol, benzyl alcohol, chlorobutanol, quaternary ammonium salts, and parabens (such as methyl paraben, ethyl paraben and propyl paraben).

Examples of pharmaceutically acceptable stabilizers and antioxidants include ethylenediaminetetraacetic acid (EDTA), thiourea, tocopherol and butyl hydroxyanisole.

Examples of pharmaceutically acceptable moisturizers include glycerine, sorbitol, urea and polyethylene glycol.

Examples of pharmaceutically acceptable emollients include mineral oils, isopropyl myristate, and isopropyl palmitate.

The compounds may also be dermally or transdermally administered, for example, by use of a skin patch.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride.

As indicated, the compounds of the invention can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material. For topical administration, for example, the composition will generally contain from 0.01-10%, more preferably 0.01-1% of the active material.

The active agents can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage form of the invention may be administered according to a dosage and administration regimen defined by routine testing in the light of the guidelines given above in order to obtain optimal activity while minimizing toxicity or side effects for a particular patient. However, such fine tuning of the therapeutic regimen is routine in the light of the guidelines given herein.

The dosage of the active agents of the invention may vary according to a variety of factors such as underlying disease conditions, the individual's condition, weight, gender and age, and the mode of administration. An effective amount for treating a disorder can easily be determined by empirical methods known to those of ordinary skill in the art, for example by establishing a matrix of dosages and frequencies of administration and comparing a group of experimental units or subjects at each point in the matrix. The exact amount to be administered to a patient will vary depending on the state and severity of the disorder and the physical condition of the patient. A measurable amelioration of any symptom or parameter can be determined by a person skilled in the art or reported by the patient to the physician.

The amount of the agent to be administered can range between about 0.01 and about 25 mg/kg/day, preferably between about 0.1 and about 10 mg/kg/day and most preferably between 0.2 and about 5 mg/kg/day. It will be understood that the pharmaceutical formulations of the invention need not necessarily contain the entire amount of the agent that is effective in treating the disorder, as such effective amounts can be reached by administration of a plurality of doses of such pharmaceutical formulations. In general, an "effective amount" refers to the amount of a pharmaceutical composition administered to improve, inhibit, or ameliorate a disease or disorder or condition of a subject, or a symptom of a disease or disorder, in a clinically relevant manner. Any clinically relevant improvement in the subject is considered sufficient to achieve treatment. Preferably, an amount sufficient to treat is an amount that prevents the occurrence or one or more symptoms of the infection or is an amount that reduces the severity of, or the length of time during which a subject suffers from, or develops, one or more symptoms of the infection relative to a control subject that is not treated with a composition of the invention).

In a preferred embodiment of the invention, the compounds according to formula I are formulated in capsules or tablets, preferably containing 10 to 200 mg of the compounds of the invention, and are preferably administered to a patient at a total daily dose of 10 to 300 mg, preferably 20 to 150 mg and most preferably about 50 mg.

A pharmaceutical composition for parenteral administration contains from about 0.01% to about 100% by weight of the active agents of the invention, based upon 100% weight of total pharmaceutical composition.

Generally, transdermal dosage forms contain from about 0.01% to about 100% by weight of the active agents versus 100% total weight of the dosage form.

The pharmaceutical composition or unit dosage form may be administered in a single daily dose, or the total daily dosage may be administered in divided doses. In addition, co-administration or sequential administration of another compound for the treatment of the disorder may be desirable. To this purpose, the combined active principles are formulated into a simple dosage unit.

For combination treatment where the compounds are in separate dosage formulations, the compounds can be administered concurrently, or each can be administered at staggered intervals. For example, the compound of the invention may be administered in the morning and the antimuscarinic compound may be administered in the evening, or vice versa.

Additional compounds may be administered at specific intervals too. The order of administration will depend upon a variety of factors including age, weight, gender and medical condition of the patient; the severity and aetiology of the disorders to be treated, the route of administration, the renal and hepatic function of the patient, the treatment history of the patient, and the responsiveness of the patient. Determination of the order of administration may be fine-tuned and such fine-tuning is routine in the light of the guidelines given herein.

Synthesis

Compounds of formula I, and enantiomers, diastereomers, N-oxides, and pharmaceutically acceptable salts thereof, may be prepared by the general methods outlined hereinafter, said methods constituting a further aspect of the invention.

The compounds of this invention can be prepared by employing reactions as shown in the following schemes, in addition to other standard manipulations that are known in the literature, exemplified in the experimental section or clear to one skilled in the art. The starting materials which are not described herein are either commercially available or may be prepared by employing reactions described in the literature or are clear to one skilled in the art. The following examples are provided so that the invention might be more fully understood, are illustrative only, and should not be construed as limiting.

It will be appreciated by those skilled in the art that it may be desirable to use protected derivatives of intermediates used in the preparation of the compounds according to formula I.

Protection and deprotection of functional groups may be performed by methods known in the art (see, for example, Green and Wuts *Protective Groups in Organic Synthesis*. John Wiley and Sons, New York, 1999).

The abbreviation PG describes a "protecting group" which is introduced to a reactive group before a certain manipulation is carried out, and which is later removed. Examples of PG's for protecting a reactive group include: acetyl-, trifluoracetyl-, benzoyl-, ethoxycarbonyl-, N-tert-butoxycarbonyl-(BOC), N-benzyloxycarbonyl-(Cbz), benzyl-, methoxybenzyl-, 2,4-dimethoxybenzyl- and for amino groups additionally the phthalyl-group for amino-alkylamino or imino groups; N-methoxymethyl-(MOM), N-benzyloxymethyl-(BOM), N-(trimethylsilyl)ethoxymethyl-(SEM), N-tert-butyl-dimethylsiloxymethyl-, N-tert-butyl-dimethylsilyl-(TBDMS), N-triisopropylsilyl-(TIPS), N-benzyl-, N-4-methoxybenzyl (PMB), N-triphenylmethyl-(Tr), N-tert-butoxycarbonyl-(BOC), N-benzyloxycarbonyl-(Cbz) or N-trimethylsilylethylsulfonyl-(SES) for amide groups; methoxy-, benzyloxy-, trimethylsilyl-(TMS), acetyl-, benzoyl-, tert-butyl-, trityl-, benzyl-, or tetrahydropyranyl (THP) groups for hydroxy groups; or trimethylsilyl- (TMS), methyl-ethyl-, tert-butyl-, benzyl-, or tetrahydropyranyl (THP) groups for carboxyl groups.

The compounds of the invention are generally prepared according to the following scheme, wherein groups R, A, B and n are as previously defined herein:

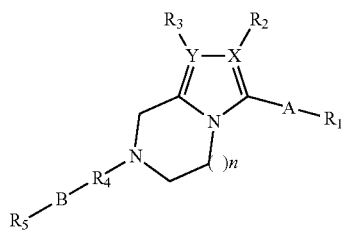

Scheme 1.

In some embodiments, the final product may be further modified, for example by manipulation of substituents. These manipulations may include, but are not limited to, reduction, oxidation, alkylation, acylation, and hydrolysis reactions which are commonly known to those skilled in the art. In some embodiments, the order of carrying out the foregoing reaction schemes may be varied in order to facilitate the reaction or to avoid unwanted reaction products. The following examples are provided so that the invention might be more fully understood. These examples are illustrative only and should not be constructed as limiting the invention in any way.

represents a leaving group such as halogen, mesylate, tosylate, alkylsulphonate, triflate or other without limitation. This last derivatization procedure can be carried out using standard methods such us e.g. Buchwald reactions, acylation reactions, reaction with alkyl/arylisocyanates, alkyl/aryl-chloroformate, chloroformamides, activated carbonates or ureas, reductive amination, alkylation or any kind of N-derivatization reaction useful to the aim of forming compounds according to formula IA, IB or IC and very well known to people skilled in the art.

This last reaction can be carried out also by the previous formation of suitable intermediates e.g. a chlorosulphonyl or chlorocarbonyl 1-imidazolylcarbonyl N-derivatives of intermediate 4.

Alternatively, compounds of the invention can be prepared again according to Scheme 1 by direct derivatization of compounds 1 similarly to what described above to afford compounds 5, which on turn can be converted into compounds IA, IB or IC by the same alkynylation procedures just described for compounds 3.

The syntheses of other compounds not currently described in this general description are well documented inside the experimental part of this invention which follows.

The free bases of compounds according to formula I, their diastereomers or enantiomers can be converted to the corresponding pharmaceutically acceptable salts under standard conditions well known in the art. For example, the free base is dissolved in a suitable organic solvent, such as methanol, treated with, for example one equivalent of maleic or oxalic

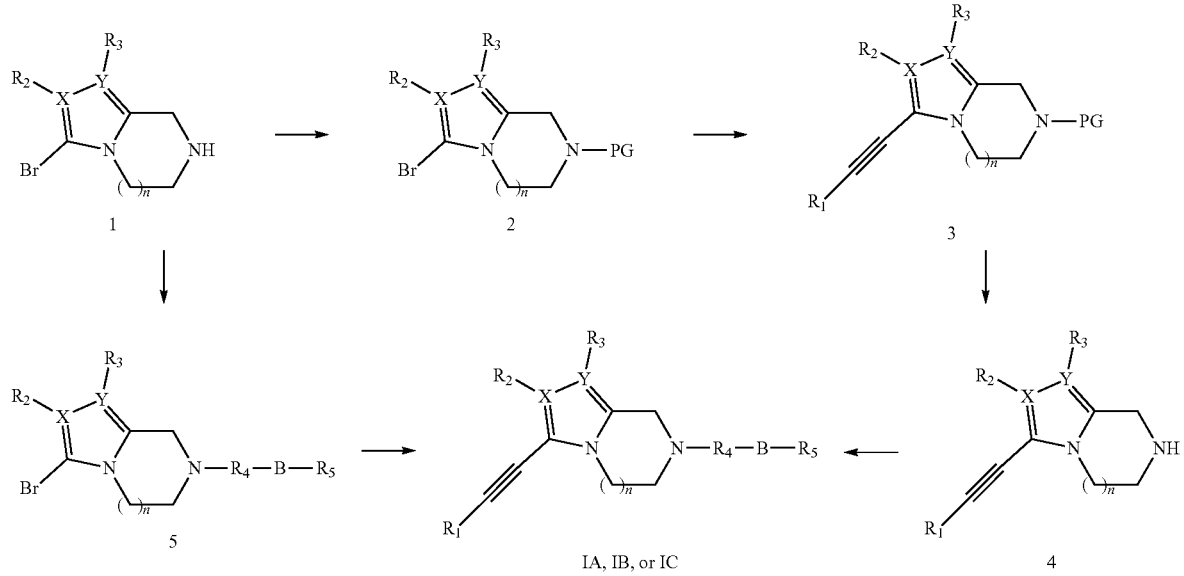

As shown in Scheme 1 commercially available starting material 1 can be easily converted into a N-protected 3-bromo-5,6,7,8-tetrahydro-[1,2,4]triazolo[4,3-a]pyrazine (2) by using consolidated methodologies well known to people skilled in the art. On turn 2 is reacted using Sonogashira or Sonogashira-Heck coupling methodologies with the opportune mono substituted alkynyl derivative to obtain compounds 3. In the next step N-protected compounds 3 are then de-protected with known methodologies to afford compounds 4, which are reacted with a $R_5$—B—$R_4$-LG intermediate directly to obtain compounds IA, IB or IC. LG acid, one or two equivalents of hydrochloric acid or methanesulphonic acid, and then concentrated under vacuum to provide the corresponding pharmaceutically acceptable salt. The residue can then be purified by recrystallization from a suitable organic solvent or organic solvent mixture, such as methanol/diethyl ether.

The N-oxides of compounds according to formula I can be synthesized by simple oxidation procedures well known to those skilled in the art.

Preparation of Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:
AcOH acetic acid
MeCN acetonitrile
Aq. aqueous
BOC tert-butyloxycarbonyl
conc. concentrated
DCM dichloromethane
DCE 1,2-dichloroethane
DIPEA N,N-diisopropylethylamine
DMF N,N-dimethylformamide
DMSO dimethyl sulfoxide
EI electron ionisation
ESI electrospray ionisation
EtOAc ethyl acetate
EtOH ethanol
HCl hydrochloric acid
HCOOH formic acid
MeOH methanol
MS mass spectrometry
MW molecular weight
NaOH sodium hydroxide
NH$_4$OH ammonium hydroxide (30% ammonia in water)
PE petroleum ether
R$_f$ retention value (from thin layer chromatography)
RT or r.t. room temperature
R$_t$ retention time (from HPLC)
THF tetrahydrofurane
TEA triethylamine
TFA trifluoracetic acid
UPLC ultra high-performance liquid chromatography
UPLC-MS UPLC coupled with mass spectrometry The following examples illustrate some of the compounds of general formula I as described above. These examples are illustrative only and are not intended to limit the scope of the invention. The reagents and starting materials are readily available to those skilled in the art.

Example 1 tert-Butyl 3-[2-(3-chlorophenyl)ethynyl]-6,8-dihydro-5H-[1,2,4]triazolo[4,3-a]pyrazine-7-carboxylate A mixture of tert-butyl 3-bromo-6,8-dihydro-5H-[1,2,4]triazolo[4,3-a]pyrazine-7-carboxylate (1.65 mmol, 500 mg), 1-chloro-3-ethynyl-benzene (3.3 mmol, 450.5 mg, 0.406 mL), Pd tetrakis (0.083 mmol, 95.3 mg) and sodium acetate (3.3 mmol, 448.9 mg) in DMF anhydrous (10 mL) was stirred at 120° C. in a MW Biotage Robot 8 oven for 10 minutes, cooled to r.t., poured into water and extracted with EtOAc. The combined organic layers were washed with brine and dried over Na$_2$SO$_4$. The solvent was removed in vacuo and the crude residue was purified via automated flash chromatography (Biotage Isolera, SNAP25 cartridge) eluted with Petroleum ether/EtOAc gradient from 30% to 100% of EtOAc.

The title product (280 mg, 47% yield) was isolated as a pale yellow solid.

Alternative Preparation:

To a solution of tert-butyl 3-bromo-6,8-dihydro-5H-[1,2,4]triazolo[4,3-a]pyrazine-7-carboxylate (3 g, 9.90 mmol) in DMF anhydrous (15 mL) in a microwave vial, 1-chloro-3-ethynylbenzene (1.622 g, 11.88 mmol, 1.2 eq., 1.462 mL) was added, followed by bis(triphenylphosphine)palladium (II) dichloride (0.278 g, 0.396 mmol, 0.04 eq.), copper(I) iodide (0.057 g, 0.297 mmol, 0.03 eq.) and TEA (1.302 g, 12.87 mmol, 1.30 eq., 1.80 mL).

The microwave vial was flushed with nitrogen, sealed and heated at 110° C. under MW irradiation for 11 min in a Biotage Initiator Robot8® apparatus. Then 0.02 eq. of palladium catalyst and 0.02 eq. of copper iodide were added, and the solution was heated under microwave irradiation for further 6 min. After cooling at room temperature, water and EtOAc were added, the two phases were separated, the organic layer was washed with water and brine, dried over Na$_2$SO$_4$, filtered and evaporated. The crude residue was purified by means of a Biotage Isolera® One flash chromatography apparatus, cartridge type SNAP50, using a gradient from petroleum ether: EtAcO from 3:7 to 0:1 affording 1.4 g of a yellow powder containing triphenylphosphine oxide besides to wished product as detected by LC-MS. So, the sample was re-purified by the same apparatus on a reverse phase column chromatography (SNAP60) using a gradient NH$_4$HCO$_3$ buffer: MeCN from 2:8 to 1:1 recovering after evaporation of the collected fractions 1.175 g of the title compound.

UPLC-MS [M+H]$^+$=359.58, 361.61, 362.63
$^1$H NMR (400 MHz, DMSO-d$_6$) δ ppm 1.45 (s, 9H), 3.82 (t, 2H), 4.14 (t, 2H), 4.74 (s, 2H), 7.49-7.56 (m, 1H), 7.61 (ddd, 1H), 7.66 (dt, 1H), 7.81 (t, 1H)

Example 2

{3-[(3-Chlorophenyl)ethynyl]-5,6-dihydro[1,2,4]triazolo[4,3-a]pyrazin-7(8H)-yl}(4-methylfuran-2-yl)methanone 3-[2-(3-Chlorophenyl)ethynyl]-5,6,7,8-tetrahydro-[1,2,4]triazolo[4,3-a]pyrazine (Compound 2a)

To an ice bath cooled solution of the final compound of Example 1 (1.170 g, 3.26 mmol) in CHCl$_3$ (50 mL) was added trifluoroacetic acid (7.436 g, 5.02 mL, 65.22 mmol) and the resulting mixture was stirred at reflux for 30 min. After cooling at room temperature, chloroform and excess TFA were removed under reduced pressure. An aqueous potassium carbonate saturated solution and DCM were added; the two phases were separated, and the aqueous layer was extracted with DCM. The combined organic phases were washed with brine, dried over Na$_2$SO$_4$, filtered and evaporated to dryness in vacuo to afford 840 mg of the title compound as a light brown powder, which was used in the next step without any further purification.

{3-[(3-Chlorophenyl)ethynyl]-5,6-dihydro[1,2,4]triazolo[4,3-a]pyrazin-7(8H)-yl}(4-methylfuran-2-yl)methanone A solution of 4-methylfuran-2-carbonyl chloride (45 mg, 0.311 mmol), 3-[2-(3-chlorophenyl)ethynyl]-5,6,7,8-tetrahydro-[1,2,4]triazolo[4,3-a]pyrazine (60 mg, 0.232 mmol) and DIPEA (59.95 mg, 0.464 mmol, 2 equiv., 0.081 mL) in chloroform ethanol-free (3 mL), was stirred for 3 hours. The reaction mixture was washed with water. The organic layer was washed again with brine, dried over Na$_2$SO$_4$ and the solvent was evaporated to give a crude which was purified twice via automated flash chromatography coupled with mass detection (Biotage Isolera-Dalton®) with a SNAP10 Cartridge, eluting firstly with a gradient EtOAc:MeOH from 10:0 to 9:1, secondly with a SNAP12 RP cartridge eluting with a gradient H₂O/ACN from 8:2 to 7:3 to give 17 mg of the tile compound (Yield: 20%).

UPLC-MS [M+H]⁺=367.20

¹H NMR (400 MHz, DMSO-d₆) δ ppm 8.75 (brd, 1H), 7.82 (t, 1H), 7.58-7.71 (m, 4H), 7.49-7.56 (m, 1H), 7.07 (s, 1H), 5.06 (brs, 2H), 4.10-4.34 (m, 4H), 2.05 (d, 3H), 1.21-1.37 (m, 14H)

According to the same method disclosed above the following compounds were prepared from Compound 2a by acylating/aroylating with the proper acyl/aroyl chloride:

Example 3

[3-[2-(3-Chlorophenyl)ethynyl]-6,8-dihydro-5H-[1,2,4]triazolo[4,3-a]pyrazin-7-yl]-(4,5-dimethyl-2-furyl)methanone From Compound 2a and 4,5-dimethyl-2-furoyl chloride.
UPLC-MS [M+H]⁺=381.25

¹H NMR (400 MHz, CDCl₃) δ ppm 7.57-7.62 (m, 1H), 7.42-7.53 (m, 2H), 7.32-7.40 (m, 1H), 7.00 (s, 1H), 5.32 (s, 2H), 4.14-4.30 (m, 4H), 2.32 (s, 3H), 2.01 (s, 3H)

Example 4

[3-[2-(3-Chlorophenyl)ethynyl]-6,8-dihydro-5H-[1,2,4]triazolo[4,3-a]pyrazin-7-yl]-[3-(trifluoromethyl)phenyl]methanone From Compound 2a and 3-trifluoromethylbenzoyl chloride.
UPLC-MS [M+H]⁺=431.21

¹H NMR (400 MHz, CDCl₃) δ ppm 7.74-7.86 (m, 2H), 7.60-7.72 (m, 2H), 7.57 (t, 1H), 7.48 (dt, 1H), 7.41-7.46 (m, 1H), 5.01 (d, 2H), 4.00-4.33 (m, 4H)

Example 5

[3-[2-(3-Chlorophenyl)ethynyl]-6,8-dihydro-5H-[1,2,4]triazolo[4,3-a]pyrazin-7-yl]-(m-tolyl)methanone From Compound 2a and 3-methylbenzoyl chloride.
UPLC-MS [M+H]⁺=377.11

¹H NMR (400 MHz, DMSO-d₆) δ ppm 7.81 (t, 1H), 7.66 (dt, 1H), 7.61 (ddd, 1H), 7.49-7.56 (m, 1H), 7.26-7.42 (m, 4H), 4.92 (s, 2H), 4.22 (t, 2H), 3.69-4.06 (m, 2H), 2.37 (s, 3H)

Example 6

[3-[2-(3-Chlorophenyl)ethynyl]-6,8-dihydro-5H-[1,2,4]triazolo[4,3-a]pyrazin-7-yl]-phenyl-methanone From Compound 2a and benzoyl chloride.
UPLC-MS [M+H]⁺=363.15

¹H NMR (400 MHz, DMSO-d₆) δ ppm 7.81 (t, 1H), 7.66 (dt, 1H), 7.59-7.64 (m, 1H), 7.44-7.58 (m, 6H), 4.93 (s, 2H), 4.23 (t, 2H), 3.58-4.13 (m, 2H)

Example 7

[3-[2-(3-Chlorophenyl)ethynyl]-6,8-dihydro-5H-[1,2,4]triazolo[4,3-a]pyrazin-7-yl]-(2-furyl)methanone From Compound 2a and 2-furoyl chloride.
UPLC-MS [M+H]⁺=353.35, 355.38, 356.36

¹H NMR (400 MHz, DMSO-d₆) δ ppm 4.18 (d, 2H), 4.23-4.33 (m, 2H), 5.09 (br. s., 2H), 6.70 (dd, 1.8 Hz, 1H), 7.20 (d, 1H), 7.54 (t, 1H), 7.61 (dd, 1H), 7.67 (dt, 1H), 7.82 (t, 1H), 7.93 (d, 1H)

Example 8

(3-Chlorophenyl)-[3-[2-(3-chlorophenyl)ethynyl]-6,8-dihydro-5H-[1,2,4]triazolo[4,3-a]pyrazin-7-yl]methanone From Compound 2a and 3-chlorobenzoyl chloride.
UPLC-MS [M+H]⁺=397.09, 399.07, 400.06

¹H NMR (400 MHz, DMSO-d₆) δ ppm 7.81 (t, 1H), 7.45-7.70 (m, 8H), 4.94 (s, 2H), 4.21 (t, 2H), 3.58-4.11 (m, 2H)

According to the same method disclosed above for the compound of Example 2 the following compounds were prepared from Compound 2a by reacting with the proper chloroformamide or chloroformate or isocyanate or reactive carbonate or other acylating reagents:

Example 9

[3-[2-(3-Chlorophenyl)ethynyl]-6,8-dihydro-5H-[1,2,4]triazolo[4,3-a]pyrazin-7-yl]-morpholinomethanone From Compound 2a and 4-morpholinecarbonyl chloride. Obtained as a white solid.
UPLC-MS [M+H]⁺=372.57, 374.52, 375.54

¹H NMR (400 MHz, DMSO-d₆) δ ppm 3.21-3.28 (m, 4H), 3.56-3.63 (m, 4H), 3.66 (t, 2H), 4.18 (t, 2H), 4.57 (s, 2H), 7.53 (t, 1H), 7.61 (ddd, 1.0 Hz, 1H), 7.66 (dt, 1H), 7.81 (t, 1H)

Example 10

[3-[(Z)-1-Chloro-2-(3-chlorophenyl)vinyl]-6,8-dihydro-5H-[1,2,4]triazolo[4,3-a]pyrazin-7-yl]-morpholino-methanone From Compound 2a and 4-morpholinecarbonyl chloride. Obtained as a by-product of the compound of Example 9.
UPLC-MS [M+H]⁺=408.40, 410.43, 411.37

¹H NMR (400 MHz, DMSO-d₆) δ ppm 3.26 (t, 4H), 3.57-3.68 (m, 6H), 4.18 (t, 2H), 4.58 (s, 2H), 7.33 (s, 1H), 7.51-7.58 (m, 2H), 7.79-7.85 (m, 1H), 7.92-7.96 (m, 1H)

Example 11

[3-[2-(3-Chlorophenyl)ethynyl]-6,8-dihydro-5H-[1,2,4]triazolo[4,3-a]pyrazin-7-yl]-(1-piperidyl)methanone From Compound 2a and 4-piperidinecarbonyl chloride. Obtained as a white solid.
UPLC-MS [M+H]⁺=370.61, 372.57, 373.58

¹H NMR (400 MHz, DMSO-d₆) δ ppm 1.44-1.62 (m, 6H), 3.19-3.27 (m, 4H), 3.61 (t, 2H), 4.17 (t, 2H), 4.52 (s, 2H), 7.53 (t, 1H), 7.61 (ddd, 1H), 7.66 (dt, 1H), 7.81 (t, 1H)

Example 12

[3-[2-(3-Chlorophenyl)ethynyl]-6,8-dihydro-5H-[1,2,4]triazolo[4,3-a]pyrazin-7-yl]-pyrrolidin-1-yl-methanone From Compound 2a and 1-pyrrolidinecarbonyl chloride. Obtained as a white solid.
UPLC-MS [M+H]$^+$=356.54, 358.57, 359.58
$^1$H NMR (400 MHz, DMSO-d$_6$) δ ppm 1.73-1.85 (m, 4H), 3.32-3.40 (m, 4H), 3.68 (t, 2H), 4.16 (t, 2H), 4.56 (s, 2H), 7.53 (t, 1H), 7.61 (ddd, 1H), 7.66 (dt, 1H), 7.81 (t, 1H)

Example 13

3-[2-(3-Chlorophenyl)ethynyl]-N-(2,2-dimethylpropyl)-6,8-dihydro-5H-[1,2,4]triazolo[4,3-a]pyrazine-7-carboxamide From Compound 2a and 1-isocyanato-2,2-dimethyl-propane. Obtained as a white solid.
UPLC-MS [M+H]$^+$=372.15, 374.13, 375.13
$^1$H NMR (400 MHz, DMSO-d$_6$) δ ppm 7.79-7.86 (m, 1H), 7.66 (dt, 1H), 7.58-7.63 (m, 1H), 7.48-7.56 (m, 1H), 6.78 (t, 1H), 4.79 (s, 2H), 4.11 (t, 2H), 3.85 (t, 2H) 2.93 (d, 2H), 0.83 (s, 9H)

Example 14

2,2-Dimethylpropyl 3-[2-(3-chlorophenyl)ethynyl]-6,8-dihydro-5H-[1,2,4]triazolo[4,3-a]pyrazine-7-carboxylate From Compound 2a and 2,2-dimethylpropyl carbonochloridate. Obtained as a white solid.
UPLC-MS [M+H]$^+$=373.14, 375.13
$^1$H NMR (400 MHz, DMSO-d$_6$) δ ppm 7.81 (t, 1H), 7.66 (dt, 1H), 7.58-7.63 (m, 1H), 7.50-7.57 (m, 1H), 4.81 (s, 2H), 4.18 (t, 2H), 3.90 (t, 2H) 3.79 (s, 2H), 0.95 (s, 9H)

Example 15

3-[2-(3-Chlorophenyl)ethynyl]-N,N-diethyl-6,8-dihydro-5H-[1,2,4]triazolo[4,3-a]pyrazine-7-carboxamide From Compound 2a and diethylaminocarbonyl chloride. Obtained as a white solid.
UPLC-MS [M+H]$^+$=358.57, 360.60, 361.61
$^1$H NMR (400 MHz, DMSO-d$_6$) δ ppm 1.09 (t, 6H), 3.22 (q, 4H), 3.60 (t, 2H), 4.16 (t, 2H), 4.48 (s, 2H), 7.53 (t, 1H), 7.61 (ddd, 1H), 7.66 (dt, 1H), 7.81 (t, 1H)

Example 16

3-[2-(3-Chlorophenyl)ethynyl]-N,N-dimethyl-6,8-dihydro-5H-[1,2,4]triazolo[4,3-a]pyrazine-7-carboxamide From Compound 2a and dimethylaminocarbonyl chloride. Obtained as a white solid.
UPLC-MS [M+H]$^+$=330.57, 332.53, 333.55
$^1$H NMR (400 MHz, DMSO-d$_6$) δ ppm 2.84 (s, 6H), 3.62 (t, 2H) 4.17 (t, 2H), 4.51 (s, 2H), 7.53 (t, 1H), 7.61 (ddd, 1H), 7.66 (dt, 1H), 7.81 (t, 1H)

Example 17

Methyl 3-[2-(3-chlorophenyl)ethynyl]-6,8-dihydro-5H-[1,2,4]triazolo[4,3-a]pyrazine-7-carboxylate From Compound 2a and methyl chloroformate, to obtain the compound of example 17 as a yellowish solid.
UPLC-MS [M+H]$^+$=317.3, 319.3, 320.4
$^1$H NMR (400 MHz, DMSO-d$_6$) δ ppm 3.69 (s, 3H) 3.87 (t, 2H), 4.16 (t, 2H), 4.79 (s, 2H), 7.53 (t, 1H), 7.61 (ddd, 1H), 7.66 (dt, 1H), 7.81 (t, 1H)

Example 18

[3-[2-(3-Chlorophenyl)ethynyl]-6,8-dihydro-5H-[1,2,4]triazolo[4,3-a]pyrazin-7-yl]-(2,2-dimethylmorpholin-4-yl)methanone From Compound 2a and 2,2-dimethylmorpholine-4-carbonyl chloride.

Example 19

Tetrahydropyran-4-yl 3-[2-(3-chlorophenyl)ethynyl]-6,8-dihydro-5H-[1,2,4]triazolo[4,3-a]pyrazine-7-carboxylate From Compound 2a and (2,5-dioxopyrrolidin-1-yl)tetrahydropyran-4-yl carbonate (US 2016/0250276). Obtained as a white solid.
UPLC-MS [M+H]$^+$=387.28, 389.26, 390.25
$^1$H NMR (400 MHz, DMSO-d$_6$) δ ppm 7.81 (t, 1H), 7.59-7.70 (m, 2H), 7.50-7.57 (m, 1H), 4.76-4.89 (m, 3H), 4.17 (t, 2H), 3.89 (t, 2H), 3.76-3.84 (m, 2H), 3.49 (ddd, 2H), 1.82-1.95 (m, 2H), 1.60 (dtd, 2H).

Example 20

3-[2-(3-Chlorophenyl)ethynyl]-N-(2-isopropoxy-1,1-dimethyl-ethyl)-6,8-dihydro-5H-[1,2,4]triazolo[4,3-a]pyrazine-7-carboxamide White solid from Compound 2a and (2,5-dioxopyrrolidin-1-yl) N-(2-isopropoxy-1,1-dimethyl-ethyl)carbamate which on turn was prepared as following:

To a stirred solution of bis-(2,5-dioxopyrrolidin-1-yl) carbonate (0.99 mmol, 253.8 mg) in dry MeCN (5 mL) at room temperature was added 1-isopropoxy-2-methyl-propan-2-amine (0.76 mmol, 100 mg) and the resulting mixture was stirred in the same condition for 2 hours. LC/MS showed a complete conversion so that the mixture was concentrated under reduced pressure and the residue diluted with aqueous NaHCO$_3$ and extracted with EtOAc. The combined extracts were washed with brine and dried over Na$_2$SO$_4$. Evaporation of the solvent provided 2,5-dioxopyrrolidin-1-yl) N-(2-isopropoxy-1,1-dimethyl-ethyl)carbamate 200 mg as a white solid that was used without further purification.

Example 20 Analytical Data

UPLC-MS [M+H]$^+$=416.18, 418.16, 419.15
$^1$H NMR (400 MHz, DMSO-d$_6$) δ ppm 7.79-7.83 (m, 1H), 7.59-7.68 (m, 2H), 7.53 (dd, 1H), 6.14 (s, 1H), 4.72 (s, 2H), 4.10 (t, 2H), 3.81 (t, 2H), 3.47 (spt, 1H), 3.42 (s, 2H), 1.23 (s, 6H), 1.03 (d, 6H)

Example 21

3-[2-(3-Chlorophenyl)ethynyl]-N-(2-pyridyl)-6,8-dihydro-5H-[1,2,4]triazolo[4,3-a]pyrazine-7-carboxamide From Compound 2a and (2,5-dioxopyrrolidin-1-yl) N-(2-pyridyl)carbamate (US 20070049618 page 110). Obtained as a white solid.

UPLC-MS [M+H]$^+$=379.27, 381.25, 382.24

$^1$H NMR (400 MHz, DMSO-d$_6$) δ ppm 9.63 (s, 1H), 8.28 (dt, 1H), 7.82 (t, 1H), 7.77-7.81 (m, 1H), 7.69-7.76 (m, 1H), 7.67 (dt, 1H), 7.58-7.64 (m, 1H), 7.50-7.57 (m, 1H), 7.02 (ddd, 1H), 4.92 (s, 2H), 4.16-4.25 (m, 2H), 4.01 (t, 2H)

Example 22

3-[2-(3-Chlorophenyl)ethynyl]-N-(2-methoxyethyl)-N-methyl-6,8-dihydro-5H-[1,2,4]triazolo[4,3-a]pyrazine-7-carboxamide From Compound 2a and N-(2-Methoxyethyl)-N,3-dimethylimidazol-3-ium-1-carboxamide iodide (purchased). Obtained as a brownish oil.

UPLC-MS [M+H]$^+$=374.0, 376.06, 377.12

$^1$H NMR (400 MHz, DMSO-d$_6$) δ ppm 2.90 (s, 3H), 3.25 (s, 3H), 3.36 (t, 2H), 3.49 (t, 2H), 3.62 (t, 2H), 4.16 (t, 2H), 4.50 (s, 2H), 7.53 (t, 1H), 7.61 (ddd, 1H), 7.66 (dt, 1H), 7.81 (t, 1H)

Example 23

3-[2-(3-Chlorophenyl)ethynyl]-N-ethyl-N-methyl-6,8-dihydro-5H-[1,2,4]triazolo[4,3-a]pyrazine-7-carboxamide From Compound 2a and 1-[ethyl(methyl)carbamoyl]-3-methyl-H-imidazol-3-ium iodide.

Obtained as a yellowish solid.

UPLC-MS [M+H]$^+$=344.11, 346.12, 347.22

$^1$H NMR (400 MHz, DMSO-d$_6$) δ ppm 1.09 (t, 3H), 2.84 (s, 3H), 3.21 (q, 2H), 3.61 (dd, 2H), 4.17 (dd, 2H), 4.49 (s, 2H), 7.53 (dd, 1H), 7.61 (ddd, 1H), 7.66 (ddd, 1H), 7.81 (dd, 1H)

Example 24

3-[2-(3-Chlorophenyl)ethynyl]-N-methoxy-N-methyl-6,8-dihydro-5H-[1,2,4]triazolo[4,3-a]pyrazine-7-carboxamide From Compound 2a and N-methoxy-N-methylcarbamoyl chloride. The product is recovered as a yellowish solid.

UPLC-MS [M+H]$^+$=346.38, 348.41, 349.42

$^1$H NMR (400 MHz, DMSO-d$_6$) δ ppm 2.94 (s, 3H), 3.63 (s, 3H), 3.85 (t, 2H), 4.18 (t, 2H), 4.76 (s, 2H), 7.53 (t, 1H), 7.61 (ddd, 1H), 7.67 (dt, 1H), 7.82 (t, 1H)

Example 25

Ethyl 3-[2-(3-chlorophenyl)ethynyl]-6,8-dihydro-5H-[1,2,4]triazolo[4,3-a]pyrazine-7-carboxylate From Compound 2a and ethyl chloroformate. The product is recovered as a yellowish solid.

UPLC-MS [M+H]$^+$=331.4, 333.4, 334.4

$^1$H NMR (400 MHz, DMSO-d$_6$) δ ppm 1.24 (t, 3H), 3.87 (t, 2H), 4.12 (t, 2H), 4.16 (dd, 2H), 4.79 (s, 2H), 7.53 (t, 1H), 7.59-7.64 (m, 1H), 7.66 (dt, 1H), 7.81 (t, 1H)

Example 26

(3-Chlorophenyl)-[3-[2-(6-methyl-2-pyridyl)ethynyl]-6,8-dihydro-5H-[1,2,4]triazolo[4,3-a]pyrazin-7-yl]methanone

3-Bromo-6,8-dihydro-5H-[1,2,4]triazolo[4,3-a]pyrazin-7-yl)-(3-chlorophenyl)methanone (Compound 26a)

To a solution of 3-bromo-5,6,7,8-tetrahydro-[1,2,4]triazolo[4,3-a]pyrazine hydrochloride (4.18 mmol, 1 g) in CH$_2$C2 (30 mL) cooled at 0° C., TEA (12.53 mmol, 1.268 g, 1.61 mL) was added followed by 3-chlorobenzoyl chloride (6.26 mmol, 0.80 mL, 1.096 g) and the mixture was stirred at room temperature for 3 h. Then water was added, the two phases were separated, the organic layer was washed with water and brine, dried over Na$_2$SO$_4$, filtered and evaporated.

The crude residue was purified by means of a Biotage Isolera One, cartridge type SNAP50, using a gradient from EtOAc 100% to EtOAc:MeOH 8:2. 1.320 g of the title compound (yellow oil) was collected.

(3-Chlorophenyl)-[3-[2-(6-methyl-2-pyridyl)ethynyl]-6,8-dihydro-5H-[1,2,4]triazolo[4,3-a]pyrazin-7-yl]methanone To a solution of Compound 26a (150 mg, 0.44 mmol) in DMF (1 mL) in a MW vial was added 2-ethynyl-6-methyl-pyridine (0.88 mmol, 102.9 mg)) followed by sodium acetate 3H$_2$O (0.88 mmol, 119.5 mg) and tetrakis(triphenylphosphine)palladium (0.022 mmol, 25.38 mg) and the mixture was heated under MW irradiation in Biotage Initiator 8® microwave oven at 120° C. for 15 min. Then water was added, the two phases were separated, the organic layer was washed with water and brine, dried over Na$_2$SO$_4$, filtered and evaporated. The crude residue was purified by means of a Biotage Isolera Four (coupled with Dalton MS detector), cartridge type SNAP25 (collect all mode) using a gradient from EtAcO 100% to EtAcO:MeOH 8:2. 20 mg of the tile compound (brown oil) were collected along with impurities. The sample was then re-purified on a reverse phase column chromatography, cartridge type SNAP12, using a gradient from NH$_4$HCO$_3$ buffer:MeCN 85:15 to NH$_4$HCO$_3$ buffer:MeCN 1:1. 9 mg of the wished compound (white powder) were collected.

UPLC-MS [M+H]$^+$=378.28, 380.17, 381.34

$^1$H NMR (400 MHz, DMSO-d$_6$) δ ppm 7.62-7.71 (m, 1H), 7.45-7.55 (m, 3H), 7.43 (t, 1H), 7.31-7.39 (m, 1H), 7.23 (d, 1H), 5.02 (br. s., 2H), 4.23-4.37 (m, 2H), 3.94-4.21 (m, 2H), 2.62 (s, 3H)

Using the above methodology reported for Example 26 and replacing 2-ethynyl-6-methyl-pyridine with the proper alkyne the following compounds were prepared:

Example 27

3-[2-[7-(3-Chlorobenzoyl)-6,8-dihydro-5H-[1,2,4]triazolo[4,3-a]pyrazin-3-yl]ethynyl]benzonitrile From Compound 26a and 3-ethynylbenzonitrile. Obtained as a white solid.

UPLC-MS [M+H]$^+$=388.18, 390.25, 391.06

$^1$H NMR (400 MHz, DMSO-d$_6$) δ ppm 7.88 (t, 1H), 7.83 (dt, 1H), 7.75 (dt, 1H), 7.55-7.63 (m, 1H), 7.48-7.55 (m, 2H), 7.45 (t, 1H), 7.35-7.40 (m, 1H), 5.04 (s, 2H), 3.96-4.31 (m, 4H)

Example 28

(3-Chlorophenyl)-[3-[2-(4-chloro-2-pyridyl)ethynyl]-6,8-dihydro-5H-[1,2,4]triazolo[4,3-a]pyrazin-7-yl]methanone From Compound 26a and 4-chloro-2-ethynylpyridine using bis(triphenylphosphine)palladium(II) dichloride instead of tetrakis(triphenylphosphine)palladium. The product was recovered as a dark powder.

UPLC-MS [M+H]$^+$=398.21, 400.19, 401.10

$^1$H NMR (400 MHz, CDCl$_3$) δ ppm 8.58 (d, 1H), 7.66 (d, 1H), 7.32-7.57 (m, 6H), 5.04 (s, 2H), 4.22-4.36 (m, 2H), 4.12 (s, 1H)

Example 29

(3-Chlorophenyl)-[3-[2-(3-fluorophenyl)ethynyl]-6,8-dihydro-5H-[1,2,4]triazolo[4,3-a]pyrazin-7-yl]methanone From Compound 26a and 1-ethynyl-3-fluorobenzene. Obtained as a white solid

Example 30

(3-Chlorophenyl)-[3-(2-cyclohexylethynyl)-6,8-dihydro-5H-[1,2,4]triazolo[4,3-a]pyrazin-7-yl]methanone From Compound 26a and cyclohexylacetylene. Recovered as a yellow light oil.

UPLC-MS [M+H]$^+$=369.18, 371.25

$^1$H NMR (400 MHz, DMSO-d$_6$) δ ppm 7.43-7.63 (m, 4H), 4.58-5.09 (m, 2H), 3.96-4.14 (m, 2H), 3.59-3.95 (m, 2H), 2.75-2.87 (m, 1H) 1.26-1.93 (m, 10H)

Example 31

(3-Chlorophenyl)-[3-(2-phenylethynyl)-6,8-dihydro-5H-[1,2,4]triazolo[4,3-a]pyrazin-7-yl]methanone From Compound 26a and phenylacetylene. Recovered as a yellow oil.

UPLC-MS [M+H]$^+$=363.15, 365.13

$^1$H NMR (400 MHz, CDCl$_3$) δ ppm 7.32-7.64 (m, 9H), 5.02 (d, 2H), 4.03-4.26 (m, 4H)

Example 32 tert-Butyl 3-[2-(m-tolyl)ethynyl]-6,8-dihydro-5H-[1,2,4]triazolo[4,3-a]pyrazine-7-carbo-xylate Using the methodology reported above for Example 1 and replacing 1-chloro-3-ethynylbenzene with 3-tolylacetylene the title compound was prepared and obtained as a white solid.

UPLC-MS [M+H]$^+$=339.64

$^1$H NMR (400 MHz, DMSO-d$_6$) δ ppm 1.45 (s, 9H), 2.36 (s, 3H), 3.82 (t, 2H), 4.11 (t, 2H), 4.73 (s, 2H), 7.31-7.42 (m, 2H), 7.47 (d, 1H), 7.51 (s, 1H)

Example 33

[3-[2-(m-Tolyl)ethynyl]-6,8-dihydro-5H-[1,2,4]triazolo[4,3-a]pyrazin-7-yl]-(1-piperidyl)methanone hydrochloride 3-[2-(m-Tolyl)ethynyl]-5,6,7,8-tetrahydro-[1,2,4]triazolo[4,3-a]pyrazine (Compound 33a)

A solution of the compound of example 32 (187 mg, 0.553 mmol) in 4.4 M HCl in isopropanol (5.03 mL, 22.1 mmol) was stirred at r.t. for 2 h. afterwards, it was evaporated to dryness in vacuo affording 170 mg of the title compound as a white solid used in the next step without further purification.

[3-[2-(m-Tolyl)ethynyl]-6,8-dihydro-5H-[1,2,4]triazolo[4,3-a]pyrazin-7-yl]-(1-piperidyl)methanone To a suspension of Compound 33a (50 mg, 0.21 mmol) was added TEA (87.5 µL, 0.63 mmol) under stirring followed by 1-piperidinecarbonyl chloride. The solution was kept under stirring for 16 h. Then the crude obtained by solvent evaporation was purified by automated flash chromatography (Biotage Isolera One®) using a gradient from EtOAc 100% to EtOAc: MeOH 8:2 giving 32 mg of a gummy solid.

UPLC-MS [M+H]$^+$=359.59

$^1$H NMR (400 MHz, DMSO-d$_6$) δ ppm 1.39-1.61 (m, 6H), 2.35 (s, 3H), 3.06-3.26 (m, 4H), 3.60 (t, 2H), 4.14 (t, 2H), 4.50 (s, 2H), 7.34 (d, 1H), 7.38 (t, 1H), 7.47 (d, 1H), 7.49-7.52 (m, 1H)

Following the synthesis method drawn for the compound of Example 33 and replacing 1-piperidinecarbonyl chloride with the proper acylating reagent the compounds below were prepared:

Example 34

2-Furyl-[3-[2-(m-tolyl)ethynyl]-6,8-dihydro-5H-[1,2,4]triazolo[4,3-a]pyrazin-7-yl]methanone From Compound 33a and 2-furoyl chloride. Recovered as a white solid.

UPLC-MS [M+H]$^+$=333.46

$^1$H NMR (400 MHz, DMSO-d$_6$) δ ppm 2.35 (s, 3H), 4.16 (br. s., 2H), 4.23 (d, 2H), 5.07 (br. s., 2H), 6.69 (dd, 1H), 7.19 (dd, 1H), 7.32-7.36 (m, 1H), 7.39 (t, 1H), 7.47 (d, 1H), 7.51 (s, 1H), 7.92 (dd, 1H)

Example 35

N,N-Diethyl-3-[2-(m-tolyl)ethynyl]-6,8-dihydro-5H-[1,2,4]triazolo[4,3-a]pyrazine-7-carboxamide From Compound 33a and diethylaminocarbonyl chloride. Recovered as a white solid.
UPLC-MS [M+H]$^+$=338.55
$^1$H NMR (400 MHz, DMSO-d$_6$) δ ppm 1.08 (t, 6H), 2.35 (s, 3H), 3.21 (q, 4H), 3.58 (t, 2H), 4.13 (t, 2H), 4.45 (s, 2H), 7.34 (d, 1H), 7.38 (t, 1H), 7.47 (d, 1H), 7.50 (s, 1H)

Example 36

N,N-Dimethyl-3-[2-(m-tolyl)ethynyl]-6,8-dihydro-5H-[1,2,4]triazolo[4,3-a]pyrazine-7-carboxamide From Compound 33a and dimethylaminocarbonyl chloride. The product was recovered as a gummy solid.
UPLC-MS [M+H]$^+$=310.49
$^1$H NMR (400 MHz, DMSO-d$_6$) δ ppm 2.36 (s, 3H), 2.84 (s, 6H), 3.62 (t, 2H), 4.15 (t, 2H), 4.50 (s, 2H), 7.35 (d, 1H), 7.39 (t, 1H), 7.48 (d, 1H), 7.52 (s, 1H)

Example 37

N-Methoxy-N-methyl-3-[2-(m-tolyl)ethynyl]-6,8-dihydro-5H-[1,2,4]triazolo[4,3-a]pyrazine-7-carboxamide From Compound 33a and N-methoxy-N-methylcarbamoyl chloride. The product was recovered as a gummy solid.
UPLC-MS [M+H]$^+$=326.51
$^1$H NMR (400 MHz, DMSO-d$_6$) δ ppm 2.36 (s, 3H), 2.94 (s, 3H), 3.62 (s, 3H), 3.85 (t, 2H), 4.15 (t, 2H), 4.75 (s, 2H), 7.35 (d, 1H), 7.39 (t, 1H), 7.48 (d, 1H), 7.51 (s, 1H)

Example 38

N-Isopropyl-N-methyl-3-[2-(m-tolyl)ethynyl]-6,8-dihydro-5H-[1,2,4]triazolo[4,3-a]pyrazine-7-carboxamide From Compound 33a and N-isopropyl-N,3-dimethyl-imidazol-3-ium-1-carboxamide iodide.
The product was recovered as a pale yellow solid.
UPLC-MS [M+H]$^+$=338.43
$^1$H NMR (400 MHz, CDCl$_3$) δ ppm 1.19 (d, 6H), 2.38 (s, 3H), 2.79 (s, 3H), 3.68 (t, 2H), 4.04-4.17 (m, 1H), 4.20 (t, 2H), 4.65 (s, 2H), 7.19-7.33 (m, 2H), 7.35-7.43 (m, 2H)

Example 39

N-(2-Methoxyethyl)-N-methyl-3-[2-(m-tolyl)ethynyl]-6,8-dihydro-5H-[1,2,4]triazolo[4,3-a]pyrazine-7-carboxamide From Compound 33a and N-(2-Methoxyethyl)-N,3-dimethylimidazol-3-ium-1-carboxamide iodide (purchased). The product was recovered as a yellow oil.
UPLC-MS [M+H]$^+$=354.26
$^1$H NMR (400 MHz, DMSO-d$_6$) δ ppm 2.36 (s, 3H), 2.90 (s, 3H), 3.25 (s, 3H), 3.34-3.39 (m, 2H), 3.46-3.52 (m, 2H), 3.62 (s, 2H), 4.14 (t, 2H), 4.49 (s, 2H), 7.32-7.36 (m, 1H), 7.39 (t, 1H), 7.47 (d, 1H), 7.51 (s, 1H)

Example 40

N-Ethyl-N-methyl-3-[2-(m-tolyl)ethynyl]-6,8-dihydro-5H-[1,2,4]triazolo[4,3-a]pyrazine-7-carboxamide From Compound 33a and 1-[ethyl(methyl)carbamoyl]-3-methyl-H-imidazol-3-ium iodide. The product, a negative allosteric modulator, was recovered as a yellowish solid.
UPLC-MS [M+H]$^+$=324.28
$^1$H NMR (400 MHz, DMSO-d$_6$) δ ppm 1.09 (t, 3H), 2.36 (s, 3H), 2.84 (s, 3H), 3.21 (q, 2H), 3.61 (t, 2H), 4.14 (t, 2H), 4.48 (s, 2H) 7.31-7.37 (m, 1H), 7.39 (t, 1H), 7.47 (d, 1H), 7.51 (s, 1H)

Example 41

1-Piperidyl 3-[2-(m-tolyl)ethynyl]-6,8-dihydro-5H-[1,2,4]triazolo[4,3-a]pyrazine-7-carboxylate To a solution of compound 33a (140 mg, 0.588 mmol) in DCM (15 mL) and DIPEA (206 μl, 1.18 mmol) was added dropwise at r.t a solution of triphosgene (69.8 mg, 0.235 mmol) in 5 mL of DCM. After 5 min. a solution of 1-hydroxypiperidine (89.2 mg, 0.882 mmol) and DIPEA (103 μl, 0.59 mmol) were added. After stirring overnight at r.t. the reaction mixture was diluted with DCM, the organic layer separated, dried over sodium sulphate and evaporated to dryness.

Purification by automated flash chromatography with a Biotage Isolera, FLASH 12+ column, using a gradient from PE:EtOAc 2:8 to EtOAc 100% afforded 13 mg of a white gummy solid, which was repurified on a SNAP 12 RP column with a gradient from NH$_4$HCO$_3$ buffer:ACN 6:4 to NH$_4$HCO$_3$ buffer:ACN 1:1. 6 mg of the title compound was obtained as a gummy solid.
UPLC-MS [M+H]$^+$=366.79
$^1$H NMR (400 MHz, CDCl$_3$) δ ppm 1.28 (s, 1H), 1.65 (br. s., 1H), 1.74-1.88 (m, 4H), 2.39 (s, 3H), 2.70 (br. s., 2H), 3.46 (br. s., 2H), 3.97 (t, 2H), 4.14 (t, 2H), 4.91 (s, 2H), 7.20-7.36 (m, 2H), 7.36-7.46 (m, 2H)

Example 42

Morpholino-[3-[2-(m-tolyl)ethynyl]-6,8-dihydro-5H-[1,2,4]triazolo[4,3-a]pyrazin-7-yl]methanone From Compound 33a and 1-morpholinocarbonyl chloride with the product recovered as a white solid.
UPLC-MS [M+H]$^+$=352.48
$^1$H NMR (400 MHz, DMSO-d$_6$) δ ppm 2.35 (s, 3H), 3.25 (t, 4H), 3.59 (t, 4H), 3.65 (t, 2H), 4.15 (t, 2H), 4.55 (s, 2H), 7.34 (d, 1H), 7.38 (t, 1H), 7.46 (d, 1H), 7.49-7.52 (m, 1H)

Example 43

(3-Chlorophenyl)-[3-[2-(m-tolyl)ethynyl]-6,8-dihydro-5H-[1,2,4]triazolo[4,3-a]pyrazin-7-yl]methanone From Compound 33a and benzoyl chloride with the product recovered as a beige solid.
UPLC-MS [M+H]$^+$=377.43
$^1$H NMR (400 MHz, DMSO-d$_6$) δ ppm 2.36 (s, 3H), 3.68-4.00 (m, 2H), 4.19 (t, 2H), 4.61-5.33 (m, 2H), 7.33-7.42 (m, 2H), 7.45-7.57 (m, 4H), 7.57-7.64 (m, 2H)

Example 44

[3-[2-(m-Tolyl)ethynyl]-6,8-dihydro-5H-[1,2,4]triazolo[4,3-a]pyrazin-7-yl]-pyrrolidin-1-yl-methanone From Compound 33a and 1-pyrrolidinecarbonyl chloride, with the product recovered as a gummy solid.
UPLC-MS [M+H]$^+$=336.52
$^1$H NMR (400 MHz, DMSO-d$_6$) δ ppm 1.74-1.81 (m, 4H), 2.34 (s, 4H), 3.21-3.46 (m, 2H), 3.66 (t, 3H), 4.12 (t, 2H), 4.52 (s, 2H), 7.33 (d, 1H), 7.37 (t, 1H), 7.46 (d, 1H), 7.49 (s, 1H)

Example 45

Ethyl 3-[2-(m-tolyl)ethynyl]-6,8-dihydro-5H-[1,2,4]triazolo[4,3-a]pyrazine-7-carbo-xylate From Compound 33a and ethyl chloroformate, with the product recovered as a white solid
UPLC-MS [M+H]$^+$=311.58
$^1$H NMR (400 MHz, DMSO-d$_6$) δ ppm 1.24 (t, 3H), 2.36 (s, 3H), 3.86 (t, 2H), 4.06-4.20 (m, 4H), 4.78 (s, 2H), 7.35 (d, 1H), 7.39 (t, 1H), 7.47 (d, 1H), 7.51 (s, 1H)

Example 46

Methyl 3-[2-(m-tolyl)ethynyl]-6,8-dihydro-5H-[1,2,4]triazolo[4,3-a]pyrazine-7-carboxylate From Compound 33a and methyl chloroformate with the product recovered as a white solid.
UPLC-MS [M+H]$^+$=297.61
$^1$H NMR (400 MHz, DMSO-d$_6$) δ ppm 2.36 (s, 3H), 3.69 (s, 3H), 3.86 (t, 2H), 4.13 (t, 2H), 4.78 (s, 2H), 7.35 (d, 1H), 7.39 (t, 1H), 7.47 (d, 1H), 7.51 (s, 1H)

Example 47 tert-Butyl 3-[2-(3-cyano-5-fluoro-phenyl)ethynyl]-6,8-dihydro-5H-[1,2,4]triazolo[4,3-a]pyrazine-7-carboxylate Prepared using the methodology reported above for Example 1 and replacing 1-chloro-3-ethynylbenzene with 3-cyano-5-fluorophenylacetylene.
UPLC-MS [M+H]$^+$=368.35
$^1$H NMR (400 MHz, CDCl$_3$) δ ppm 1.53 (s, 9H), 3.89-4.00 (m, 2H), 4.09-4.16 (m, 2H), 4.90 (s, 2H), 7.45 (ddd, 1H), 7.51-7.56 (m, 1H), 7.66-7.69 (m, 1H)

Example 48 tert-Butyl 3-[2-(4-chloro-2-pyridyl)ethynyl]-6,8-dihydro-5H-[1,2,4]triazolo[4,3-a]pyrazine-7-carboxylate Prepared using the methodology reported above for Example 1 and replacing 1-chloro-3-ethynylbenzene with 4-chloro-2-ethynylpyridine. The product was recovered as a beige solid.
UPLC-MS [M+H]$^+$=360.38
$^1$H NMR (400 MHz, CDCl$_3$) δ ppm 1.53 (s, 9H) 3.92 (t, 2H), 4.17 (t, 2H), 4.90 (s, 2H), 7.39 (dd, 1H), 7.61-7.69 (m, 1H), 8.57 (d, 1H)

Example 49 tert-Butyl 3-[2-(1-hydroxycyclohexyl)ethynyl]-6,8-dihydro-5H-[1,2,4]triazolo[4,3-a]pyrazine-7-carboxylate Prepared using the methodology reported above for Example 1 and replacing 1-chloro-3-ethynylbenzene with 1-acetylencyclohexanol. The product was recovered as a yellowish solid.
UPLC-MS [M+H]$^+$=347.62
$^1$H NMR (400 MHz, DMSO-d$_6$) δ ppm 1.26 (dd, 1H), 1.39-1.62 (m, 5H), 1.44 (s, 9H), 1.63-1.74 (m, 2H), 1.85-1.95 (m, 2H), 3.80 (t, 2H), 3.98 (t, 2H), 4.68 (br. s., 2H), 5.72 (s, 1H)

Example 50 tert-Butyl 3-(2-phenylethynyl)-6,8-dihydro-5H-[1,2,4]triazolo[4,3-a]pyrazine-7-carboxylate Prepared using the methodology reported above for Example 1 and replacing 1-chloro-3-ethynylbenzene with phenylacetylene.
UPLC-MS [M+H]$^+$=325.43

Example 51 tert-Butyl 3-[2-(6-methyl-2-pyridyl)ethynyl]-6,8-dihydro-5H-[1,2,4]triazolo[4,3-a]pyrazine-7-carboxylate Prepared using the methodology reported above for Example 1 and replacing 1-chloro-3-ethynylbenzene with 6-methyl-2-pyridylacetylene.
UPLC-MS [M+H]$^+$=340.58

The following compounds were prepared by acid cleavage of the tert-butoxycarbonyl group of the compounds of example 47-48 and 50-51 as described above with trifluoroacetic acid or using HCl in EtOAc or i-PrOH and subsequent acylation with ethyl or methyl chloroformate or N,N-diethylcarbamoyl chloride or arylating with 2-chloro-6-methylpyridine by the standard procedure.

Example 52

Ethyl 3-[2-(3-cyano-5-fluoro-phenyl)ethynyl]-6,8-dihydro-5H-[1,2,4]triazolo[4,3-a]pyrazine-7-carboxylate This compound can be prepared from 3-fluoro-5-[2-(5,6,7,8-tetrahydro-[1,2,4]triazolo[4,3-a]pyrazin-3-yl)ethynyl]benzonitrile and ethyl chloroformate.
UPLC-MS [M+H]$^+$=340.45

Example 53

Ethyl 3-[2-(4-chloro-2-pyridyl)ethynyl]-6,8-dihydro-5H-[1,2,4]triazolo[4,3-a]pyrazine-7-carboxylate From 3-[(4-chloropyridin-2-yl)ethynyl]-5,6,7,8-tetrahydro[1,2,4]triazolo[4,3-a]pyrazine and ethyl chloroformate. The product was recovered as a yellowish oil.
UPLC-MS [M+H]$^+$=332.33, 320.07, 321.08
$^1$H NMR (400 MHz, CDCl$_3$) δ ppm 1.33 (t, 3H), 3.97 (t, 2H), 4.19 (t, 2H), 4.25 (q, 2H), 4.95 (s, 2H), 7.39 (dd, 1H), 7.66 (d, 1H), 8.57 (d, 1H)

Example 54

Methyl 3-[2-(4-chloro-2-pyridyl)ethynyl]-6,8-dihydro-5H-[1,2,4]triazolo[4,3-a]pyrazine-7-carboxylate From 3-[(4-chloropyridin-2-yl)ethynyl]-5,6,7,8-tetrahydro[1,2,4]triazolo[4,3-a]pyrazine and methyl chloroformate. The product was recovered as a beige solid.
UPLC-MS [M+H]$^+$=318.05, 334.35, 335.36
$^1$H NMR (400 MHz, CDCl$_3$) δ ppm 3.83 (s, 3H), 3.98 (d, 2H), 4.16-4.23 (m, 2H), 4.95 (s, 2H), 7.39 (dd, 1H), 7.66 (d, 1H), 8.58 (d, 1H)

Example 55

Methyl 3-[2-(6-methyl-2-pyridyl)ethynyl]-6,8-dihydro-5H-[1,2,4]triazolo[4,3-a]pyrazine-7-carboxylate From 3-[(6-methylpyridin-2-yl)ethynyl]-5,6,7,8-tetrahydro[1,2,4]triazolo[4,3-a]pyrazine and methyl chloroformate. The product was recovered as a brownish solid.
UPLC-MS [M+H]$^+$=298.38
$^1$H NMR (400 MHz, DMSO-d6) δ ppm 2.52 (s, 3H), 3.69 (s, 3H), 3.87 (t, 2H), 4.15 (t, 2H), 4.79 (s, 2H), 7.39 (d, 1H), 7.60 (d, 1H), 7.78-7.85 (m, 1H)

Example 56

Ethyl 3-[2-(6-methyl-2-pyridyl)ethynyl]-6,8-dihydro-5H-[1,2,4]triazolo[4,3-a]pyrazine-7-carboxylate From 3-[(6-methylpyridin-2-yl)ethynyl]-5,6,7,8-tetrahydro[1,2,4]triazolo[4,3-a]pyrazine and ethyl chloroformate. The product was recovered as a brownish solid.
UPLC-MS [M+H]$^+$=312.38
$^1$H NMR (400 MHz, DMSO-d6) δ ppm 1.24 (t, 3H), 2.52 (s, 3H), 3.87 (t, 2H), 4.08-4.19 (m, 4H), 4.79 (s, 2H), 7.39 (d, 1H), 7.60 (d, 1H), 7.82 (t, 1H)

Example 57

N,N-Diethyl-3-[2-(6-methyl-2-pyridyl)ethynyl]-6,8-dihydro-5H-[1,2,4]triazolo[4,3-a]pyrazine-7-carboxamide From 3-[(6-methylpyridin-2-yl)ethynyl]-5,6,7,8-tetrahydro[1,2,4]triazolo[4,3-a]pyrazine and diethylaminocarbonyl chloride. The product was recovered as a yellowish solid.
UPLC-MS [M+H]$^+$=339.42
$^1$H NMR (400 MHz, DMSO-d6) δ ppm 1.09 (t, 6H), 2.52 (s, 3H), 3.22 (q, 4H), 3.60 (t, 2H), 4.16 (t, 2H), 4.48 (s, 2H), 7.39 (d, 1H), 7.60 (d, 1H), 7.82 (t, 1H)

Example 58

7-(6-Methyl-3-nitro-2-pyridyl)-3-(2-phenylethynyl)-6,8-dihydro-5H-[1,2,4]triazolo[4,3-a]pyrazine Obtained by reacting 3-(phenylethynyl)-5,6,7,8-tetrahydro[1,2,4]triazolo[4,3-a]pyrazine and 2-chloro-6-methyl-3-nitropyridine.
UPLC-MS [M+H]$^+$=361.18
$^1$H NMR (400 MHz, CDCl$_3$) δ ppm 2.56 (s, 3H), 3.92 (t, 2H), 4.36 (t, 2H), 4.88 (s, 2H), 6.85 (d, 1H), 7.39-7.50 (m, 3H), 7.60-7.65 (m, 2H), 8.24 (d, 1H)

Example 59 tert-Butyl 3-[(3-cyanophenyl)ethynyl]-5,6-dihydroimidazo[1,5-a]pyrazine-7(8H)-carboxylate To a solution of tert-butyl 3-bromo-6,8-dihydro-5H-imidazo[1,5-a]pyrazine-7-carboxylate (0.662 mmol, 200 mg) in dry DMF (1 mL) in a microwave vial 3-ethynylbenzonitrile (0.993 mmol, 126.23 mg) was added followed by sodium acetate 3H$_2$O (1.324 mmol, 180.14 mg) and tetrakis(triphenylphosphine)palladium (0.033 mmol, 38.24 mg), the vial was sealed, flushed with nitrogen and the mixture was heated under MW irradiation at 120° C. for 15 min. Then water was added, the two phases were separated, the organic layer was washed with water and brine, dried over Na$_2$SO$_4$, filtered and evaporated. The crude residue was purified by means of a Biotage Isolera One, cartridge type SNAP25, using a gradient from Petroleum ether:EtOAc 1:1 to Petroleum ether:EtOAc 2:8. 105 mg of the title compound (dark oil) were collected.
HPLC-MS [M+H]$^+$=349.4

Example 60

3-({7-[(2,5-Dimethylfuran-3-yl)carbonyl]-5,6,7,8-tetrahydroimidazo[1,5-a]pyrazin-3-yl}ethynyl)benzonitrile 3-[2-(5,6,7,8-tetrahydroimidazo[1,5-a]pyrazin-3-yl)ethynyl]benzonitrile (Compound 60a)

To an ice bath cooled solution of the compound of Example 59131953_I52907 in CHCl$_3$ (5 mL), trifluoroacetic acid (6.028 mmol, 687.3 mg, 0.464 mL) was added and the resulting mixture was stirred at 60° C. for 30 min. After cooling at room temperature, chloroform and excess TFA were removed under reduced pressure. Sodium bicarbonate saturated solution and DCM were added, the two phases were separated, and the aqueous layer was extracted with DCM. The combined organic phases were washed with brine, dried over Na2SO4, filtered and evaporated. 50 mg of the title compound (brownish oil) were collected and used in the next step without any further purification.
HPLC-MS [M+H]$^+$=249.3

3-({7-[(2,5-Dimethylfuran-3-yl)carbonyl]-5,6,7,8-tetrahydroimidazo[1,5-a]pyrazin-3-yl}ethynyl)benzonitrile To an ice bath cooled solution of Compound 60a in chloroform ethanol free (5 mL), TEA (0.031 g, 0.302 mmol, 3.00 equiv., 0.0422 mL) was added, followed by 2,5-dimethylfuran-3-carbonyl chloride (0.121 mmol, 0.016 mL, 0.019 g) and the mixture was stirred at r.t. for 1 h. The reaction was quenched with water, the two phases were separated, the organic layer was washed with brine, dried over Na$_2$SO$_4$, filtered and evaporated. The crude residue was purified by means of a Biotage Isolera One, cartridge type SNAP10, using a gradient from Petroleum ether:EtOAc 6:4 to EtOAc 100%. 31 mg of the title compound (light yellow powder) were collected.
UPLC-MS [M+H]$^+$=371.4
$^1$H NMR (400 MHz, CDCl$_3$) δ ppm 7.83 (t, 1H), 7.78 (dt, 1H), 7.64-7.71 (m, 1H), 7.47-7.56 (m, 1H), 6.98 (s, 1H), 5.98 (s, 1H), 4.88 (s, 2H), 4.17-4.26 (m, 2H), 4.03-4.13 (m, 2H), 2.40 (s, 3H), 2.30 (t, 3H)

Example 61

3-{[7-(3-Chlorobenzoyl)-5,6,7,8-tetrahydroimidazo[1,5-a]pyrazin-3-yl]ethynyl}benzonitrile Prepared from Compound 60a and benzoyl chloride following the method reported above for the Compound of Example 60. Light yellow powder
UPLC-MS [M+H]$^+$=387.8
$^1$H NMR (400 MHz, CDCl$_3$) δ ppm 7.82-7.88 (m, 1H), 7.76-7.81 (m, 1H), 7.65-7.71 (m, 1H), 7.47-7.57 (m, 3H), 7.41-7.46 (m, 1H), 7.33-7.39 (m, 1H), 6.98 (br d, 1H), 4.63-5.09 (m, 2H), 3.72-4.38 (m, 4H)

Example 62 tert-Butyl 3-[(3-chlorophenyl)ethynyl]-5,6-dihydroimidazo[1,5-a]pyrazine-7(8H)-carboxylate Prepared following the method reported above for the Compound of Example 59 replacing 3-chlorophenylacetylene for 3-ethynylbenzonitrile. The product was recovered as a dark oil.
UPLC-MS [M+H]$^+$=358.02, 359.99, 361.08
$^1$H NMR (400 MHz, CHLOROFORM-d) δ ppm 1.53 (s, 9H), 3.88 (t, 2H), 4.14 (t, 2H), 4.70 (s, 2H), 6.97 (s, 1H), 7.32 (t, 1H), 7.36-7.40 (m, 1H), 7.45 (dt, 1H), 7.55 (t, 1H)
After BOC deprotection of the Compound of Example 62 (see compound 60a for synthesis method), the resulting intermediate 3-[2-(3-chlorophenyl)ethynyl]-5,6,7,8-tetrahydroimidazo[1,5-a]pyrazine was reacted with the indicated reagents as reported for the compound of Example 60 and gave rise to the following compounds:

Example 63

{3-[(3-Chlorophenyl)ethynyl]-5,6-dihydroimidazo[1,5-a]pyrazin-7(8H)-yl}(2,5-dimethylfuran-3-yl)methanone From 3-[2-(3-chlorophenyl)ethynyl]-5,6,7,8-tetrahydroimidazo[1,5-a]pyrazine and 2,5-dimethylfuran-3-carbonyl chloride. The product was recovered as a pale yellow powder.

Example 64

(3-Chlorophenyl){3-[(3-chlorophenyl)ethynyl]-5,6-dihydroimidazo[1,5-a]pyrazin-7(8H)-yl}methanone From 3-[2-(3-chlorophenyl)ethynyl]-5,6,7,8-tetrahydroimidazo[1,5-a]pyrazine and 3-chlorobenzoyl chloride. Obtained as a light yellow powder.

Example 65

Ethyl 3-[(3-chlorophenyl)ethynyl]-5,6-dihydroimidazo[1,5-a]pyrazine-7(8H)-carboxylate From 3-[2-(3-chlorophenyl)ethynyl]-5,6,7,8-tetrahydroimidazo[1,5-a]pyrazine and ethyl chloroformate.

Example 66 tert-Butyl 3-[(3-cyanophenyl)ethynyl]-5,6-dihydroimidazo[1,2-a]pyrazine-7(8H)-carboxylate Prepared following the method reported above for the Compound of Example 59 replacing tert-butyl 3-bromo-6,8-dihydro-5H-imidazo[1,2-a]pyrazine-7-carboxylate for tert-butyl 3-bromo-6,8-dihydro-5H-imidazo[1,5-a]pyrazine-7-carboxylate.

After BOC deprotection of the Compound of Example 66 (see compound 60a for synthesis method), the resulting intermediate 3-[2-(5,6,7,8-tetrahydroimidazo[1,2-a]pyrazin-3-yl)ethynyl]benzonitrile was reacted as reported for the compound of Example 60 with the indicated reagents and gave rise to the following compounds:

Example 67

3-{[7-(3-Chlorobenzoyl)-5,6,7,8-tetrahydroimidazo[1,2-a]pyrazin-3-yl]ethynyl}benzonitrile From 3-[2-(5,6,7,8-tetrahydroimidazo[1,2-a]pyrazin-3-yl)ethynyl]benzonitrile and 3-chlorobenzoyl chloride.

Example 68

3-({7-[(4,5-Dimethylfuran-2-yl)carbonyl]-5,6,7,8-tetrahydroimidazo[1,2-a]pyrazin-3-yl}ethynyl)benzonitrile From 3-[2-(5,6,7,8-tetrahydroimidazo[1,2-a]pyrazin-3-yl)ethynyl]benzonitrile and 4,5-dimethylfuran-2-carbonyl chloride.

Example 69

3-({7-[(2,5-Dimethylfuran-3-yl)carbonyl]-5,6,7,8-tetrahydroimidazo[1,2-a]pyrazin-3-yl}ethynyl)benzonitrile From 3-[2-(5,6,7,8-tetrahydroimidazo[1,2-a]pyrazin-3-yl)ethynyl]benzonitrile and 2,5-dimethylfuran-3-carbonyl chloride.

Example 70 tert-Butyl 3-[(3-chlorophenyl)ethynyl]-5,6-dihydroimidazo[1,2-a]pyrazine-7(8H)-carboxylate Prepared following the method reported above for the Compound of Example 59 replacing tert-butyl 3-bromo-6,8-dihydro-5H-imidazo[1,2-a]pyrazine-7-carboxylate for tert-butyl 3-bromo-6,8-dihydro-5H-imidazo[1,5-a]pyrazine-7-carboxylate and using 3-chlorophenyl acetylene instead of 3-ethynylbenzonitrile.

After BOC deprotection of the Compound of Example 70 (see compound 60a for the synthesis method), the resulting intermediate 3-[2-(3-chlorophenyl)ethynyl]-5,6,7,8-tetrahydroimidazo[1,2-a]pyrazine was reacted as reported for the compound of Example 60 with the indicated reagents and gave rise to the following compounds:

Example 71

3-({3-[(3-Chlorophenyl)ethynyl]-5,6-dihydroimidazo[1,2-a]pyrazin-7(8H)-yl}carbonyl)benzonitrile From 3-[2-(3-chlorophenyl)ethynyl]-5,6,7,8-tetrahydroimidazo[1,2-a]pyrazine and 3-cyanobenzoyl chloride.

Example 72

{3-[(3-Chlorophenyl)ethynyl]-5,6-dihydroimidazo[1,2-a]pyrazin-7(8H)-yl}(2,5-dimethylfuran-3-yl)methanone From 3-[2-(3-chlorophenyl)ethynyl]-5,6,7,8-tetrahydroimidazo[1,2-a]pyrazine and 2,5-dimethylfuran-3-carbonyl chloride.

Example 73

(3-Chlorophenyl){3-[(3-chlorophenyl)ethynyl]-5,6-dihydroimidazo[1,2-a]pyrazin-7(8H)-yl}methanone The compound was prepared by another method but its preparation from 3-[2-(3-chlorophenyl)ethynyl]-5,6,7,8-tetrahydroimidazo[1,2-a]pyrazine and 3-chlorobenzoyl chloride is anticipated to be preferred.

Example 74

3-[(3-Chlorophenyl)ethynyl]-N-methoxy-N-methyl-5,6-dihydroimidazo[1,2-a]pyrazine-7(8H)-carboxamide The compound was prepared by another method but its preparation from 3-[2-(3-chlorophenyl)ethynyl]-5,6,7,8-tetrahydroimidazo[1,2-a]pyrazine and N-methoxy-N-methylcarbamoyl chloride is anticipated to be preferred.

Example 75

3-[(3-Chlorophenyl)ethynyl]-N,N-dimethyl-5,6-dihydroimidazo[1,2-a]pyrazine-7(8H)-carboxamide The compound was prepared by another method but its preparation from 3-[2-(3-chlorophenyl)ethynyl]-5,6,7,8-tetrahydroimidazo[1,2-a]pyrazine and N,N-dimethylcarbamoyl chloride is anticipated to be preferred.

Example 76

3-[(3-Chlorophenyl)ethynyl]-N,N-diethyl-5,6-dihydroimidazo[1,2-a]pyrazine-7(8H)-carboxamide The compound was prepared by another method but its preparation from 3-[2-(3-chlorophenyl)ethynyl]-5,6,7,8-tetrahydroimidazo[1,2-a]pyrazine and N,N-diethylcarbamoyl chloride is anticipated to be preferred.

Example 77

Ethyl 3-[(3-chlorophenyl)ethynyl]-5,6-dihydroimidazo[1,2-a]pyrazine-7(8H)-carboxylate The compound was prepared by another method but its preparation from 3-[2-(3-chlorophenyl)ethynyl]-5,6,7,8-tetrahydroimidazo[1,2-a]pyrazine and ethyl chloroformate is anticipated to be preferred.

Example 78 tert-Butyl 3-[(3-methylphenyl)ethynyl]-5,6-dihydroimidazo[1,2-a]pyrazine-7(8H)-carboxylate Prepared following the method reported above for the Compound of Example 59 replacing tert-butyl 3-bromo-6,8-dihydro-5H-imidazo[1,2-a]pyrazine-7-carboxylate for tert-butyl 3-bromo-6,8-dihydro-5H-imidazo[1,5-a]pyrazine-7-carboxylate and using 3-methylphenyl acetylene instead of 3-ethynylbenzonitrile.

After BOC deprotection of the Compound of Example 78 (see compound 60a for the synthesis method), the resulting intermediate 3-[2-(m-tolyl)ethynyl]-5,6,7,8-tetrahydroimidazo[1,2-a]pyrazine reacted as reported for the compound of Example 60 with the indicated reagents and gave rise to the following compounds:

Example 79

N-Methoxy-N-methyl-3-[(3-methylphenyl)ethynyl]-5,6-dihydroimidazo[1,2-a]pyrazine-7(8H)-carboxamide The compound was prepared by another method but its preparation from 3-[2-(m-tolyl)ethynyl]-5,6,7,8-tetrahydroimidazo[1,2-a]pyrazine and N-methoxy-N-methylcarbamoyl chloride is anticipated to be preferred.

Example 80

N,N-Dimethyl-3-[(3-methylphenyl)ethynyl]-5,6-dihydroimidazo[1,2-a]pyrazine-7(8H)-carboxamide The compound was prepared by another method but its preparation from 3-[2-(m-tolyl)ethynyl]-5,6,7,8-tetrahydroimidazo[1,2-a]pyrazine and N,N-dimethylcarbamoyl chloride is anticipated to be preferred.

Example 81

Ethyl 3-[(3-methylphenyl)ethynyl]-5,6-dihydroimidazo[1,2-a]pyrazine-7(8H)-carboxylate The compound was prepared by another method but its preparation from 3-[2-(m-tolyl)ethynyl]-5,6,7,8-tetrahydroimidazo[1,2-a]pyrazine and ethyl chloroformate is anticipated to be preferred.

Example 82

N,N-diethyl-3-[(3-methylphenyl)ethynyl]-5,6-dihydroimidazo[1,2-a]pyrazine-7(8H)-carboxamide The compound was prepared by another method but its preparation from 3-[2-(m-tolyl)ethynyl]-5,6,7,8-tetrahydroimidazo[1,2-a]pyrazine and N,N-diethylcarbamoyl chloride is anticipated to be preferred.

Example 83

Biological Assay

Cell lines stably transfected were generated using inducible expression vectors encoding human mGlu$_5$ receptor using the Tetracycline-Regulated Expression system (T-REx™ system, Invitrogen, Life Technologies). Human mGluR$_5$ open reading frame (ORF), comprehensive of the stop codon, were cloned into the pcDNA4/TO/myc-His™ A vector, carrying the TetO2. The insertion site was HindIII-PstI for mGluR$_5$ receptors. The obtained constructs were then transfected into the T-REx CHO™ cell line using the FuGENE protocol (Roche); the CHO T-REx™ cell line stably expresses the Tet repressor (from the pcDNA6/TR plasmid) under the selection of blasticidin, 10 µg/ml. Stable clones were obtained selecting with zeocin 1 mg/ml and maintaining in ULTRA CHO medium (LONZA) supplemented with dialyzed FBS, zeocin, blasticidin, at 37° C., in an atmosphere of 5% $CO_2$. The expression of h-mGluR$_5$ receptors was de-repressed with 1 μg/ml tetracycline for 18 h before binding experimentation, while the expression of h-mGluR$_5$ receptors was derepressed respectively with 3 ng/ml and 10 ng/ml tetracycline for 18 h before calcium fluorescence experimentation.

Example 84

Radioligand Binding Assay at Native mGluR5 and mGluR5 Receptor Subtypes

Affinity at transmembrane glutamate metabotropic mGluR$_5$ receptor subtypes was evaluated according to the methods of Anderson (Anderson et al., *J Pharmacol. Exp. Ther.*, (2002), Vol. 303(3), pp. 1044-51), with some modifications. Cloned mGluR$_5$ was obtained by re-suspending CHO T-REx h-mGluR$_5$ cells (50 μg/well) in 20 mM HEPES, 2 mM MgCl$_2$, 2 mM CaCl$_2$, pH 7.4, that then were incubated in a final volume of 1 ml for 60 min at 25° C. with 4 nM [$^3$H]MPEP in the absence or presence of competing drugs. Non-specific binding was determined in the presence of 10 μM MPEP. The incubation was stopped by addition of cold Tris buffer pH 7.4 and rapid filtration through 0.2% polyethyleneimine pretreated Filtermat 1204-401 (Perkin Elmer) filters. The filters were then washed with cold buffer and the radioactivity retained on the filters was counted by liquid scintillation spectrometry (Betaplate 1204 BS-Wallac). The affinity (Ki) of the compounds of the instant invention for mGlu$_5$ receptor is between 0.1 and 1000 nM. For instance, Compound of Example 8 has a Ki of 33.75 nM and Compound of Example 40 has a Ki of 32 nM.

Example 85

Determination of Functional Activity at mGlu5 receptor as Calcium Fluorescence Measurements Cells were seeded into black-walled, clear-bottom, 96-well plates at a density of 80000 cell/well, in RPMI (without Phenol Red, without L-glutamine; Gibco LifeTechnologies, CA) supplemented with 10% dialyzed FBS. Following 18-h incubation with tetracycline, the cells were loaded with 2 mM $Ca^{2+}$- sensitive fluorescent dye Fluo-4/AM (Molecular Probes) in Hanks' balanced saline solution (HBSS, Gibco LifeTechnologies, CA) with 20 μM Hepes (Sigma) and 2.5 mM probenecid (Sigma), for 1 h at 37° C. The cells were washed three times with HBSS to remove extracellular dye. Fluorescence signals were measured by using the fluorescence microplate reader Flexstation III (Molecular Devices) at sampling intervals of 1.5 s for 60 s.

The antagonist potency was determined using the EC$_{80}$ of the quisqualate used as agonist and the potentiation of mGlu$_5$ activation was determined using the EC$_{20}$ of the agonist (quisqualate or glutamate). The compounds were applied 10 minutes before the application of the agonist. For binding and calcium assay studies, the compounds were dissolved in DMSO or demineralized water according to their solubility. All the reported doses were those of the corresponding salts or bases. The compounds of the instant invention showed positive or negative allosteric modulation activity. For instance, Compound of Example 8 showed positive allosteric activity an EC$_{50}$ of 294.5 nM. For instance, Compound of Example 40 has a negative allosteric modulation activity IC$_{50}$=60.9 nM.

Statistical Analysis.

The inhibition curves of the tested compounds at native and cloned mGluR$_1$ and mGluR$_5$ subtypes were determined by nonlinear regression analysis using software Prism 4.0 (Graphpad, San Diego, Calif.). The IC$_{50}$ values and pseudo-Hill slope coefficients were estimated by the program. The values for the inhibition constant, K$_i$, were calculated according to the equation K$_i$=IC$_{50}$/(1+[L]/K$_d$), where [L] is the concentration of radioligand and K$_d$ is the equilibrium dissociation constant of the radioligand-receptor complex (Cheng et al., *Biochem. Pharmacol.* (1973), Vol. 22, pp. 3099-3108).

The invention claimed is:

1. A compound selected from the group consisting of:

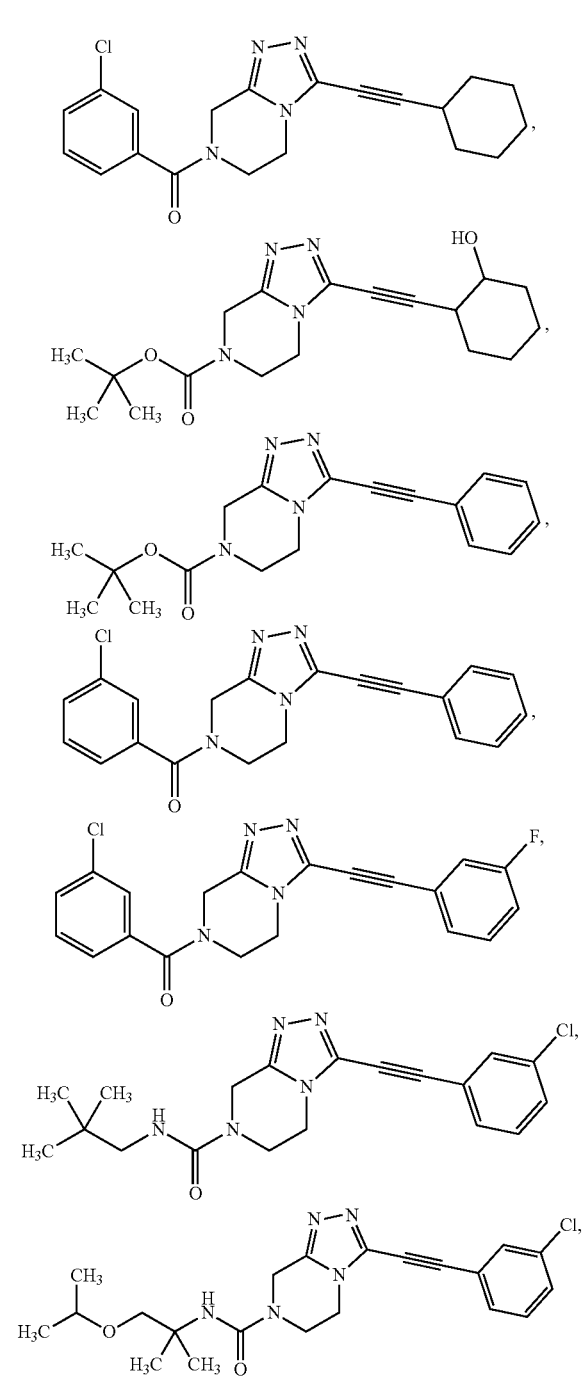

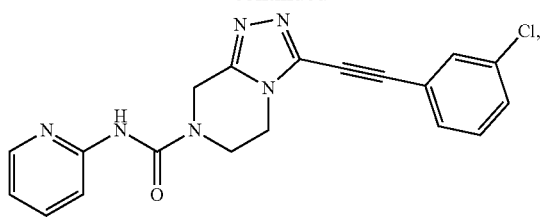
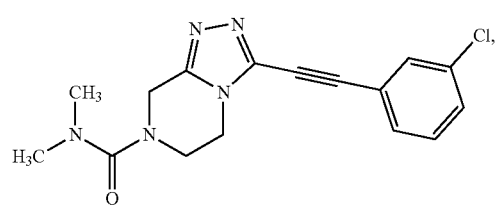
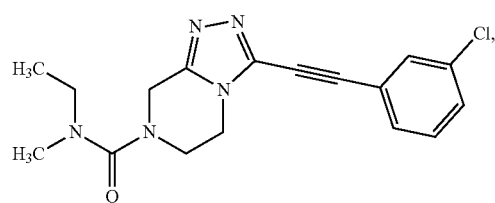
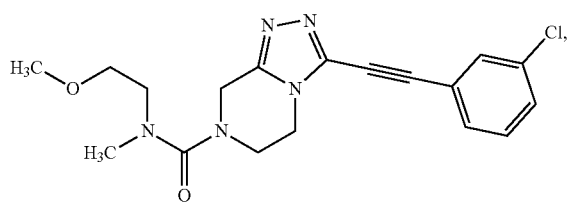
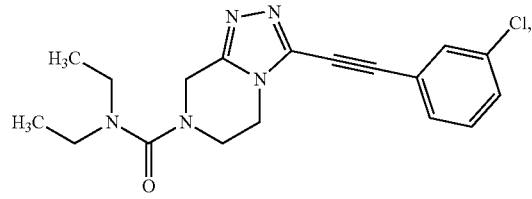
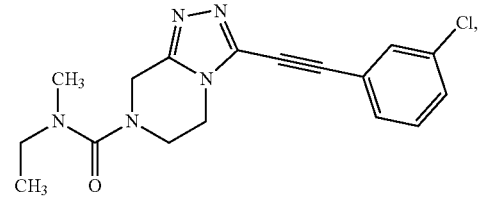
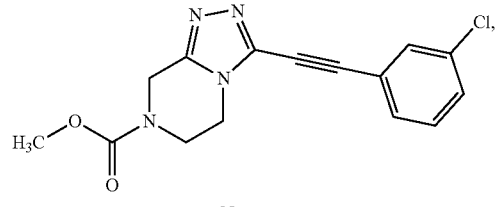
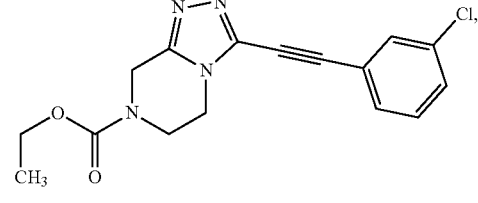
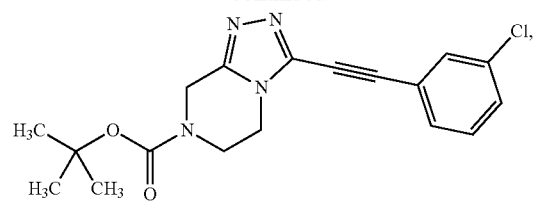
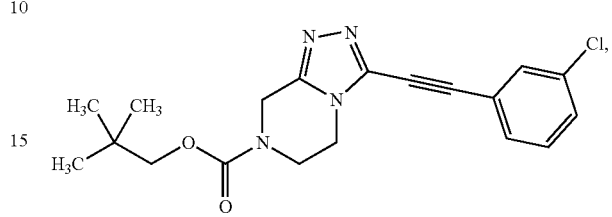
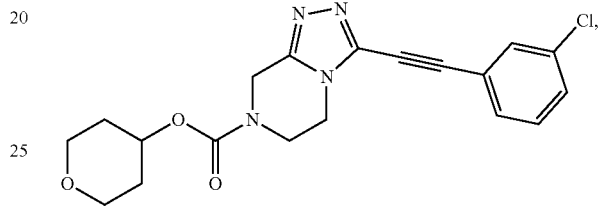
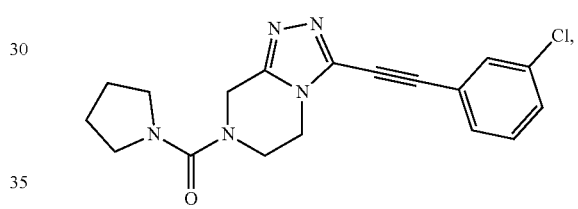
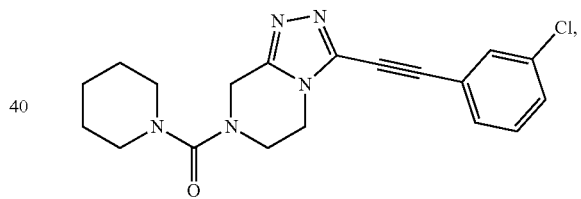
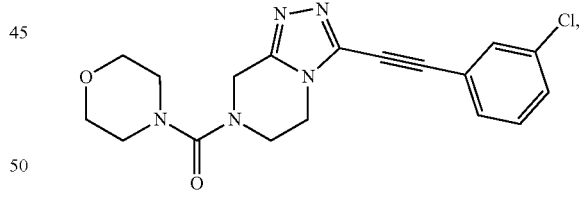
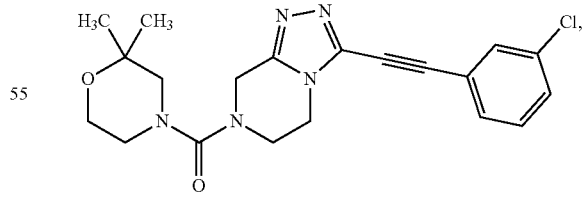
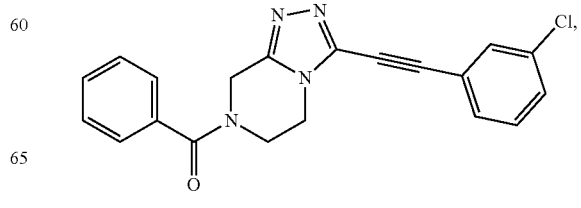

-continued
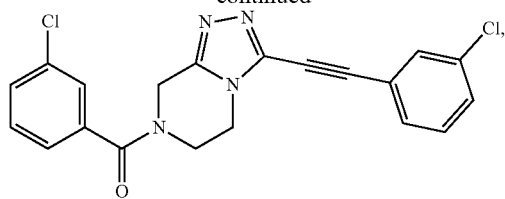
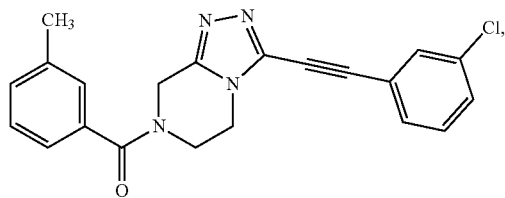
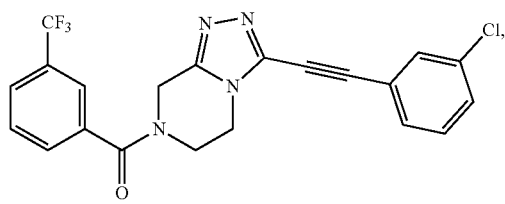
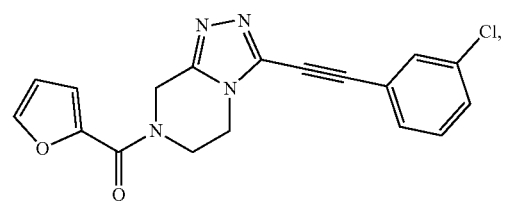
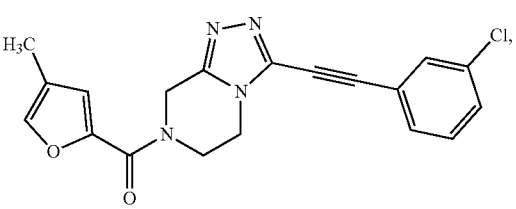
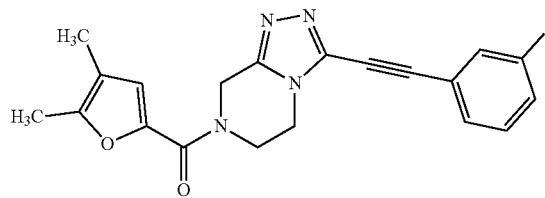
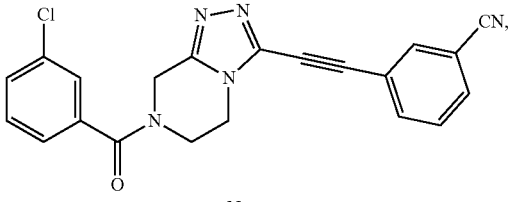
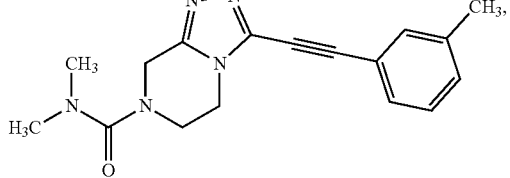
-continued
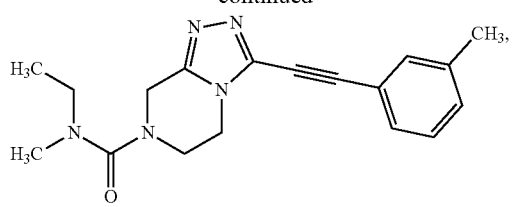
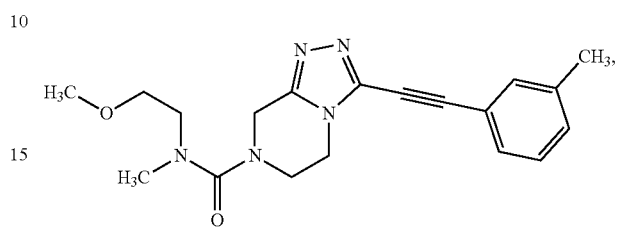
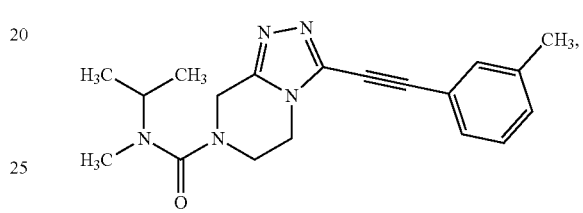
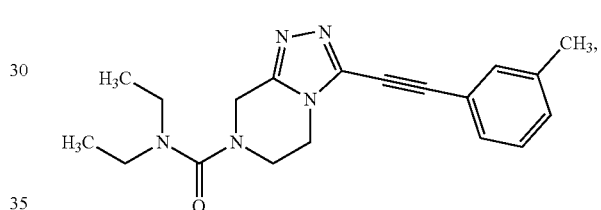
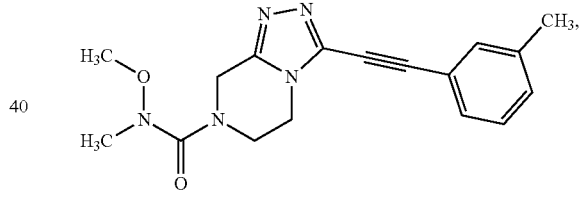
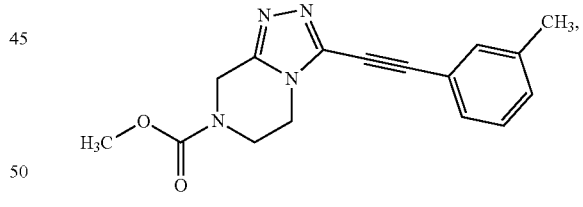
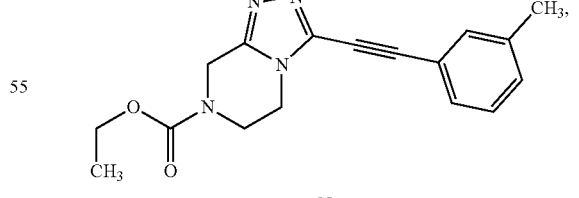
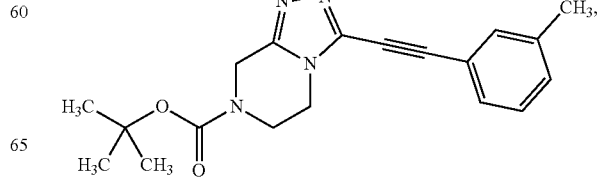

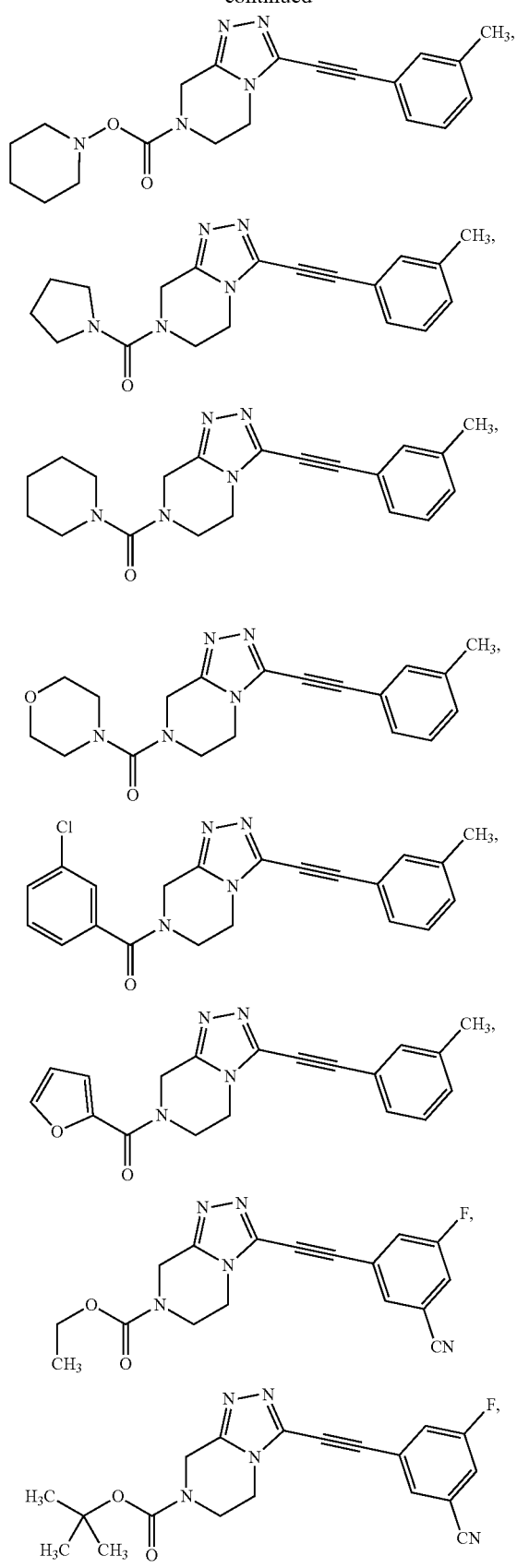
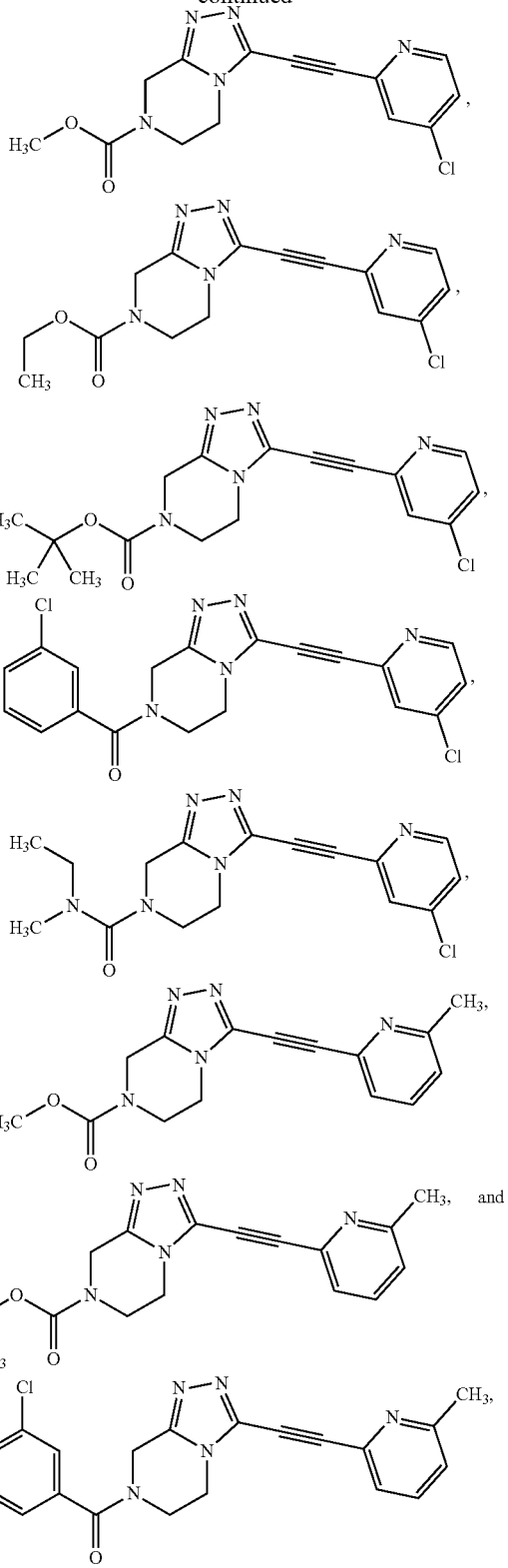
or a pharmaceutically acceptable salt thereof.
2. A pharmaceutical composition comprising a pharmaceutically acceptable carrier or diluent and a compound according to claim 1, or a pharmaceutically acceptable salt thereof.

3. A method for modulating metabotropic glutamate receptor 5 activity in a subject, wherein the method comprises administering to the subject in need thereof an effective amount of a compound according to claim 1, or a pharmaceutically acceptable salt thereof.

4. The method according to claim 3, wherein the subject has a neurological disorder associated with glutamate dysfunction or a psychological disorder associated with glutamate dysfunction selected from the group consisting of cognitive decline, cognitive impairment, dementia, and schizophrenia.

5. The method according to claim 4, wherein the cognitive decline, cognitive impairment, or dementia is selected from the group consisting of addiction, anxiety, epilepsy, fragile X syndrome, irritable bowel syndrome, levodopa-induced dyskinesia, major depressive disorder, pain, Parkinson's disease, substance abuse, substance dependence, and urinary incontinence.

6. The method according to claim 4, wherein the cognitive decline, cognitive impairment, or dementia is selected from the group consisting of Alzheimer's dementia, cognitive decline associated with autism, cognitive impairment associated with autism, Phelan-McDermid syndrome, psychosis, Rett's syndrome, and tuberous sclerosis.

7. A method for modulating metabotropic glutamate receptor 5 activity in a subject, wherein the method comprises administering to the subject in need thereof an effective amount of the pharmaceutical composition according to claim 2.

8. The method according to claim 7, wherein the subject has a neurological disorder associated with glutamate dysfunction or a psychological disorder associated with glutamate dysfunction selected from the group consisting of cognitive decline, cognitive impairment, dementia, and schizophrenia.

9. The method according to claim 8, wherein the cognitive decline, cognitive impairment, or dementia is selected from the group consisting of addiction, anxiety, epilepsy, fragile X syndrome, irritable bowel syndrome, levodopa-induced dyskinesia, major depressive disorder, pain, Parkinson's disease, substance abuse, substance dependence, and urinary incontinence.

10. The method according to claim 8, wherein the cognitive decline, cognitive impairment, or dementia is selected from the group consisting of Alzheimer's dementia, cognitive decline associated with autism, cognitive impairment associated with autism, Phelan-McDermid syndrome, psychosis, Rett's syndrome, and tuberous sclerosis.

11. A compound selected from the group consisting of:

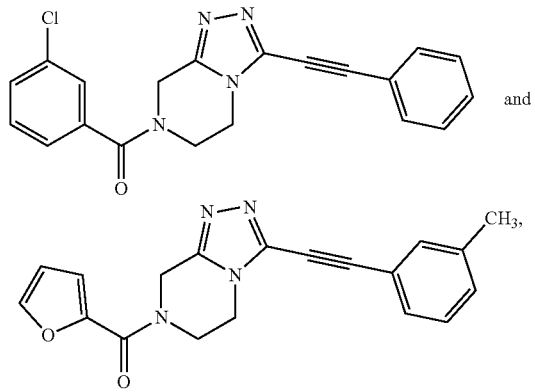

and

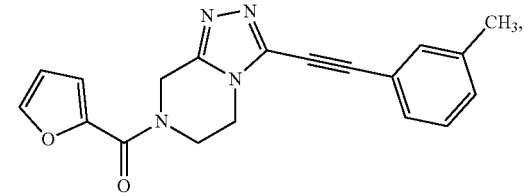

or a pharmaceutically acceptable salt thereof.

* * * * *